US008592645B2

(12) United States Patent
DeKelver et al.

(10) Patent No.: US 8,592,645 B2
(45) Date of Patent: Nov. 26, 2013

(54) ENGINEERED ZINC FINGER PROTEINS TARGETING PLANT GENES INVOLVED IN FATTY ACID BIOSYNTHESIS

(75) Inventors: Russell DeKelver, La Jolla, CA (US); Manju Gupta, Carmel, IN (US); Jeffrey C. Miller, San Leandro, CA (US); Stephen Novak, Westfield, IN (US); Joseph F. Petolino, Zionsville, IN (US)

(73) Assignees: Dow AgroSciences LLC, Indianapolis, IN (US); Sangamo BioSciences, Inc., Richmond, CA (US)

( * ) Notice: Subject to any disclaimer, the term of this patent is extended or adjusted under 35 U.S.C. 154(b) by 294 days.

(21) Appl. No.: 12/925,491

(22) Filed: Oct. 22, 2010

(65) Prior Publication Data

US 2011/0167521 A1 Jul. 7, 2011

Related U.S. Application Data

(60) Provisional application No. 61/279,528, filed on Oct. 22, 2009.

(51) Int. Cl.
*A01H 5/00* (2006.01)
*C07K 14/00* (2006.01)
*C12N 5/04* (2006.01)
*C12N 15/82* (2006.01)

(52) U.S. Cl.
USPC ........... 800/278; 800/295; 800/298; 800/306; 530/388.21; 435/419; 435/468

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,500,361 A * | 3/1996 | Kinney | 800/264 |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,323,395 B1 | 11/2001 | Rubin-Wilson | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,733,970 B2 | 5/2004 | Choo et al. | |
| 6,746,838 B1 | 6/2004 | Choo et al. | |
| 6,785,613 B2 | 8/2004 | Eisenberg et al. | |
| 6,794,136 B1 | 9/2004 | Eisenberg et al. | |
| 6,866,997 B1 | 3/2005 | Choo et al. | |
| 7,001,768 B2 | 2/2006 | Wolffe | |
| 7,030,215 B2 | 4/2006 | Liu et al. | |
| RE39,229 E | 8/2006 | Choo et al. | |
| 7,220,719 B2 | 5/2007 | Case et al. | |
| 7,235,354 B2 | 6/2007 | Case et al. | |
| 7,262,054 B2 | 8/2007 | Jamieson et al. | |
| 2002/0160940 A1* | 10/2002 | Case et al. | 514/6 |
| 2003/0037355 A1 | 2/2003 | Barbas et al. | |
| 2003/0232410 A1 | 12/2003 | Liljedahl et al. | |
| 2004/0128717 A1 | 7/2004 | Jamieson et al. | |
| 2004/0203064 A1 | 10/2004 | Case et al. | |
| 2004/0204345 A1 | 10/2004 | Case et al. | |
| 2005/0064474 A1 | 3/2005 | Urnov et al. | |
| 2006/0188987 A1 | 8/2006 | Guschan et al. | |
| 2007/0059795 A1 | 3/2007 | Moore et al. | |
| 2007/0118923 A1 | 5/2007 | Barbas et al. | |
| 2007/0134796 A1 | 6/2007 | Holmes et al. | |
| 2008/0131962 A1 | 6/2008 | Miller | |
| 2008/0182332 A1 | 7/2008 | Cai et al. | |
| 2009/0205083 A1 | 8/2009 | Gupta et al. | |
| 2009/0305419 A1 | 12/2009 | Miller | |

FOREIGN PATENT DOCUMENTS

| | | |
|---|---|---|
| GB | 2338237 A | 12/1999 |
| WO | WO 93/10240 A1 | 5/1993 |
| WO | WO 93/11245 A1 | 6/1993 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/53480 A1 | 7/2001 |
| WO | WO 01/60970 A2 | 8/2001 |

(Continued)

OTHER PUBLICATIONS

Warwick et al 2009 Guide to Wild Germplasm of *Brassica* and Allied Crops 3rd Edition.*
Lysak et al. 2005 Genome Research 15: p. 516-525.*
Beerli, et al., "Engineering Polydactyl Zinc-Finger Transcription Factors," *Nature Biotechnology* 20:135-141 (2002).
Bibikova, et al., "Stimulation of Homologous Recombination Through Targeted Cleavage by Chimeric Nucleases," *Mol. Cell. Biol.* 21:289-297 (2001).
Bitinate, et al., "FokI Dimerization Is Required for DNA Cleavage," *PNAS USA* 95:10570-10575 (1998).

(Continued)

*Primary Examiner* — Brent T Page
*Assistant Examiner* — Matthew Keogh
(74) *Attorney, Agent, or Firm* — Pasternak Patent Law; Dahna S. Pasternak

(57) ABSTRACT

The present disclosure relates to engineered zinc finger proteins that target genes in plants involved in fatty acid biosynthesis. Methods of using such zinc finger proteins in modulating gene expression, gene inactivation, and targeted gene modification are also provided.

19 Claims, 18 Drawing Sheets

(56) References Cited

FOREIGN PATENT DOCUMENTS

| WO | WO 01/88197 A2 | 11/2001 |
|---|---|---|
| WO | WO 02/16536 A1 | 2/2002 |
| WO | WO 02/057293 A2 | 7/2002 |
| WO | WO 02/077227 A2 | 10/2002 |
| WO | WO 02/099084 A2 | 12/2002 |
| WO | WO 03/016496 A2 | 2/2003 |
| WO | WO 03/080809 A2 | 10/2003 |
| WO | WO 2005/014791 A2 | 2/2005 |
| WO | WO 2005/084190 A2 | 9/2005 |
| WO | WO 2007/014275 A2 | 1/2007 |

OTHER PUBLICATIONS

Bonaventure, et al., "Disruption of the FATB Gene in *Arabidopsis* Demonstrates an Essential Role of Saturated Fatty Acids in Plant Growth," *The Plant Cell* 15:1020-1033 (2003).

Choo, et al., "Advances in Zinc Finger Engineering," *Curr. Opin. Struct. Biol.* 10:411-416 (2000).

Desjarlais, et al., "Use of a Zinc-Finger Consensus Sequences Framework and Specificity Rules to Design Specific DNA Binding, Proteins" *PNAS* 90: 2256-2260 (1993).

Desjarlais, et al., "Length-Encoded Multiplex Binding Site Determination: Application to Zinc Finger Proteins," *PNAS* 91: 11099-11103 (1994).

Guo, et al., "Directed Evolution of an Enhanced and Highly Efficient FokI Cleavage Domain for Zinc Finger Nucleases," *J Mol Biol* 400:96-107 (2010).

Hu, et al. "Mapping of the Loci Controlling Oleic and Linolenic Acid Contents and Development of FAD2 and FAD3 Allele-Specific Markers in Canola (*Brassica napus* L.)," *Theor Appl Genet* 113:497-507 (2006).

Isalan, et al., "A Rapid, Generally Applicable Method to Engineer Zinc Fingers Illustrated by Targeting the HIV-1 Promoter," *Nat Biotechnol* 19:656-660 (2001).

Kim, et al., "Chimeric Restriction Endonuclease," *PNAS USA* 91:883-887 (1994).

Kim, et al., "Insertion and Deletion Mutants of Foki Restriction Endonuclease," *J. Biol. Chem.* 269:31978-31982 (1994).

Kim, et al., "Hybrid Restriction Enzymes: Zinc Finger Fusions to Fok I Cleavage Domain," *Proc. Natl Acad. Sci. USA* 93:1156-1160 (1996).

Klug, et al., "Zinc Finger Peptides for the Regulation of Gene Expression," *J Mol Biol* 293:215-218 (1999).

Li, et al., "Functional Domains in Fok I Restriction Endonuclease," *PNAS USA* 89:4275-4279 (1992).

Li, et al., "Alteration of the Cleavage Distance of Fok I Restriction Endonuclease by Insertion Mutagenesis," *PNAS USA* 90:2764-2768 (1993).

Liu, et al., "Design of Polydactyl Zinc-Finger Proteins for Unique Addressing Within Complex Genomes," *PNAS* 94: 5525-5530 (1997).

Mensink, et al., "Effect of a Diet Enriched With Monounsaturated or Polyunsaturated Fatty Acids on Levels of Low-Density and High-Density Lipoprotein Cholesterol in Healthy Women and Men,".*New England J. Med* 321:436-441 (1989).

Miller, et al., "Repetitive Zinc-Binding Domains in the Protein Transcription Factor IIIA From *Xenopus* Oocytes," *EMBO J.* 4:1609-1614 (1985).

Moore, et al., "Design of Polyzinc Finger Peptides With Structured Linkers," *PNAS USA* 98:1432-1436 (2001).

Moore, et al., "Improved DNA Binding Specificity From Polyzinc Finger Peptides by Using Strings of Two-Finger Units," *PNAS USA* 98:1437-1441 (2001).

Morinaga, "Interspecific Hybridization in *Brassica* VI. The Cytology of F1 Hybrids of *B. juncea* and *B. nigra*," *Cytologia* 6: 62-67 (1931).

Nagaharu, "Genome Analysis in *Brassica* With Special Reference to the Experimental Formation of *B. napus* and Peculiar Mode of Fertilization," *Japan. J. Bot* 7: 389-452 (1935).

Ohlrogge, et al., "Lipid Biosynthesis," *The Plant Cell* 7:957-970 (1995).

Pabo, et al., "Design and Selection of Novel CYS2-HIS2 Zinc Finger Proteins," *Ann. Rev. Biochem.* 70:313-340 (2001).

Pomerantz, et al., "Analysis of Homeodomain Function by Structure-Based Design of a Transcription Factor," *PNAS* 92: 9752-9756 (1995).

Rhodes, et al., "Zinc Fingers: They Play a Key Part in Regulating the Activity of Genes in Many Species, From Yeast to Humans. Fewer Than 10 Years Ago No On Knew They Existed." *Scientific American* 268:56-65 (1993).

Sanchez, et al., "Regulation of *Arabidopsis thaliana* 4-Coumarate:Coenzyme-A Ligase-1 Expression by Artificial Zinc Finger Chimeras," *Plant Biotechnology Journal* 4:103-114 (2006).

Segal, et al., "Custom DNA-Binding Proteins Come of Age: Polydactyl Zinc-Finger Proteins," *Curr. Opin. Biotechnol.* 12:632-637 (2001).

Smith, et al., "Requirements for Double-Strand Cleavage by Chimeric Restriction Enzymes With Zinc Finger DNA-Recognition Domains," *Nucleic Acids Research* 28:3361-3369 (2000).

Szczepek, et al., "Structure-Based Redesign of the Dimerization Interface Reduces the Toxicity of Zinc-Finger Nucleases," *Nat Biotechnol* 25:786-793 (2007).

Van Eenennaam, et al., "Elevation of Seed Alpha-Tocopherol Levels Using Plant-Based Transcription Factors Targeted to an Endogenous Locus," *Metab Eng* 6:101-108 (2004).

Williams, et al., "Associations of Dietary Fat, Regional Adiposity, and Blood Pressure in Men," *J Am Med Assoc* 257:3251-3256 (1987).

Wu, et al., "A Mutant of *Arabidopsis* Deficient in the Elongation of Palmitic Acid," *Plant Physiology* 106:143-150 (1994).

Zaremba, et al. "Generation of the BFII Restriction Endonuclease From the Fusion of a DNA Recognition Domain to a Non-Specific Nuclease From the Phospholipase D Superfamily," *J Mol Biol* 336:81-92 (2004).

Gupta, et al. "Transcriptional Activation of *Brassica napus* SS-Ketoacyl-ACP Synthase II With an Engineered Zinc Finger Protein Transcription Factor," *Plant Biotechnology Journal* 10:783-791 (2012).

Gupta, et al., "Oil Modification Via Transcriptional Activation of Canola Kasii Using Engineered Zinc Finger Transcriptional Factor," *In Vitro Cellular & Developmental Biology Animal* 48(1): S18-S30, Abstract P-22 (2012).

Pidkowich, et al., "Modulating Seed Beta-Ketoacyl-Acyl Carrier Protein Synthase II Level Converts the Composition of a Temperate Seed Oil to That of a Palm-Like Tropical Oil," *PNAS USA* 104:4742-4747 (2007).

\* cited by examiner

Fatty acid biosynthesis pathway

```
                    1                                                  50
AF244520     (1)   --------------------------------------------------
AF318307     (1)   ATTCTCTCTTCTTCTCTTCACCCATTTCTCGCTTTCTCCTTTGTTCTCTC
Consensus    (1)
                    51                                                100
AF244520     (1)   --------------------------------------------------
AF318307    (51)   ATCTGGGTTCTTCTCAAAGCCTCTTCCTTTTTTTGCCATGGTGGGTGCGT
Consensus   (51)
                    101                                               150
AF244520     (1)   --------------------------------------------------
AF318307   (101)   CTTCCTCTTACGCATCTCCGTTATGTACCTGGTTTGTTGCTGCTTGCATG
Consensus  (101)
                    151                                               200
AF244520     (1)   --------------------------------------------------
AF318307   (151)   TCCGTCTCTCACGGTGGAGGAGATAGCCGTCAGGCTGTTGCTCTTCAATC
Consensus  (151)
                    201                                               250
AF244520     (1)   --------------------------------------------------
AF318307   (201)   TGGTGGGCGGAGTCGGCGAAGGAGGCAGCTTAGCAAATGCTCTGTCGCTT
Consensus  (201)
                    251                                               300
AF244520     (1)   --------------------------------------------------
AF318307   (251)   CTGGATCCGCTAGCATTCAGGCTCTCGTCACTTCTTGTTTGGATTTTGGT
Consensus  (251)
                    301                                               350
AF244520     (1)   --------------------------------------------------
AF318307   (301)   CCTTGTACTCACTACAACAACAACAATGCATTGTCTTCTCTCTTTGGATC
Consensus  (301)
                    351                                               400
AF244520     (1)   -----------------------------------CTCGAGCTGCTACTGCT
AF318307   (351)   GAATAGTGTTTCTTTGAATCGAAACCAGAGGAGATTGAATCG-TGCTGCT
Consensus  (351)                                      T  GA     G T CTGCT
                    401                                               450
AF244520    (18)   AGTTCCGGTGGAGGAGCCATGGCTGTTGCGATGGATATGGAAAAGGAAGC
AF318307   (400)   AGCTCCGGTGGA---GCCATGGCAGT---GATGGAGATGGAAAAGGAAGC
Consensus  (401)   AG TCCGGTGGA   GCCATGGC GT    GATGGA ATGGAAAAGGAAGC
                    451                                               500
AF244520    (68)   CAAGGTTGACAACAAACCTCCTACGGAGCAGCGCCGGGTTGTTGTGACAG
AF318307   (444)   TGCGGTTAACAAGAAACCACCTACGGAGCAGCGTCGAGTTGTAGTGACAG
Consensus  (451)      GGTT ACAA AAACC CCTACGGAGCAGCG CG GTTGT GTGACAG
                    501                                               550
AF244520   (118)   GCATGGGAGTTGAAACATCACTAGGTCATGACCCTGACACCTTTTTATGAG
AF318307   (494)   GCATGGGAGTTGAAACATCATTGGGTCATGACCCACATACCTTCTATGAG
Consensus  (501)   GCATGGGAGTTGAAACATCA T GGTCATGACCC  A ACCTT TATGAG
                    551                                               600
AF244520   (168)   AATCTCCTACAAGGCAACAGTGGTATTAGCCAGATTGAGAATTTTGATTG
AF318307   (544)   AATTTGCTACAAGGCAACAGTGGTATTAGCCAGATTGAAAATTTTGATTG
Consensus  (551)   AAT T CTACAAGGCAACAGTGGTATTAGCCAGATTGA AATTTTGATTG AF244520   (218)   TTCTGCTTTTCCTACGAGAATTGCTGGAGAGATCAAGTCATTCTCGACTG
AF318307   (594)   TTCTGAATTTCCTACGCGAATTGCGGGAGAGATCAAAAGCTTCTCGACTG
Consensus  (601)   TTCTG   TTTCCTACG GAATTGC GGAGAGATCAA   TTCTCGACTG
                    651                                               700
```

FIG. 7A

```
AF244520   (268)  AAGGGTGGGTTGCTCCAAAACTCTCAAAGAGGATGGACAAGTTCATGCTC
AF318307   (644)  AAGGATGGGTTGCTCCAAAACTTTCTAAAAGGATGGACAAATTCATGCTC
Consensus  (651)  AAGG TGGGTTGCTCCAAAACT TC AA AGGATGGACAA TTCATGCTC
                  701                                              750
AF244520   (318)  TATCTTCTCACTGCTGGCAAGAAGGCTTTGGTTGATGGTGGGGTAACCGA
AF318307   (694)  TATCTTCTCACAGCTGGTAAGAAAGCTTTGGCTGATGGTGGGGTTACTGA
Consensus  (701)  TATCTTCTCAC GCTGG AAGAA GCTTTGG TGATGGTGGGGT AC GA
                  751                                              800
AF244520   (368)  AGAAGTCATGGCAGAGTTTGACAAAGCCAAATGCGGAGTCTTGATTGGCT
AF318307   (744)  TGAAGTAATGGCAGAGTTTGACAAAACCAAATGTGGAGTTTTGATTGGCT
Consensus  (751)   GAAGT ATGGCAGAGTTTGACAAA CCAAATG GGAGT TTGATTGGCT
                  801                                              850
AF244520   (418)  CTGCAATGGGAGGCATGAAGGTCTTTCAAGATGCTATTGAAGCTATGAAG
AF318307   (794)  CGGCAATGGGAGGAATGAAGGTCTTTTACGATGCTATTGAAGCTCTGAGA
Consensus  (801)  C GCAATGGGAGG ATGAAGGTCTTT A GATGCTATTGAAGCT TGA
                  851                                              900
AF244520   (468)  ATCTCTTACAAGAAGATGAATCCTTTCTGTGTGCCTTTCGCGACAACCAA
AF318307   (844)  ATCTCTTACAAGAAGATGAATCCTTTTTGTGTACCTTTTGCGACAACAAA
Consensus  (851)  ATCTCTTACAAGAAGATGAATCCTTT TGTGT CCTTT GCGACAAC AA
                  901                                              950
AF244520   (518)  CATGGGTTCTGCTATGCTTGCTTTGGATCTGGGATGGATGGGGCCAAACT
AF318307   (894)  CATGGGTTCTGCTATGCTTGCCATGGATCTGGGATGGATGGGGCCAAACT
Consensus  (901)  CATGGGTTCTGCTATGCTTGC TGGATCTGGGATGGATGGGGCCAAACT
                  951                                              1000
AF244520   (568)  ATTCTATCTCAACTGCTTGTGCAACAAGCAACTTTTGCATTCTCAATTCA
AF318307   (944)  ATTCTATTTCAACTGCTTGTGCCACAAGCAACTTTTGCATTCTGAATTCA
Consensus  (951)  ATTCTAT TCAACTGCTTGTGC ACAAGCAACTTTTGCATTCT AATTCA
                  1001                                             1050
AF244520   (618)  GCAAACCACATTATCAAAGGAGAAGCTGATGTAATGCTCTGTGGTGGCTC
AF318307   (994)  GCAAACCACATTATTAAAGGTGAAGCTGATGTAATGCTCTGTGGTGGCTC
Consensus  (1001) GCAAACCACATTAT AAAGG GAAGCTGATGTAATGCTCTGTGGTGGCTC
                  1051                                             1100
AF244520   (668)  GGATTCAGTTATTATTCCAATAGGGTTGGGAGGTTTTGTTGCATGCCGTG
AF318307   (1044) AGATGCAGTTATTATTCCAATAGGGTTGGGAGGTTTTGTTGCATGCCGGG
Consensus  (1051)  GAT CAGTTATTATTCCAATAGGGTTGGGAGGTTTTGTTGCATGCCG G
                  1101                                             1150
AF244520   (718)  CTCTTTCTCAAAGGAATAATGATCCCACAAAAGCTTCACGCCCTTGGGAT
AF318307   (1094) CTCTTTCACAAAGGAATAATGATCCCACAAAAGCTTCACGTCCTTGGGAT
Consensus  (1101) CTCTTTC CAAAGGAATAATGATCCCACAAAAGCTTCACG CCTTGGGAT
                  1151                                             1200
AF244520   (768)  AGCAACGAGATGGTTTCGTGATGGGAGAGGGAGCTGGAGTTTGCTTTT
AF318307   (1144) ACCAATCGAGATGGTTTCGTGATGGGAGAGGGAGCTGGAGTTCTACTTTT
Consensus  (1151) A CAA CGAGATGGTTTCGTGATGGGAGAGGGAGCTGGAGTT T CTTTT
                  1201                                             1250
AF244520   (818)  GGAAGAGCTTGAACATGCTAAGAAAAGAGGAGCAACAATCTATGCAGAGT
AF318307   (1194) GGAAGAACTCGAGCATGCTAAGAAAAGAGGTGCAACTATCTACGCAGAGT
Consensus  (1201) GGAAGA CT GA CATGCTAAGAAAAGAGG GCAAC ATCTA GCAGAGT
                  1251                                             1300
AF244520   (868)  TCCTTGGTGGGAGTTTCACATGTGATGCCTATCACATGACCGAGCCTCGC
AF318307   (1244) TCCTCGGTGGGAGTTTCACATGTGATGCCTATCACATGACCGAGCCTCAC
Consensus  (1251) TCCT GGTGGGAGTTTCACATGTGATGCCTATCACATGACCGAGCCTC C
                  1301                                             1350
```

FIG. 7B

```
AF244520  (918)  CCTGATGGTGCTGGTGTGATTCTGTGTATTGAGAGAGCATTGGCTGATGC
AF318307  (1294) CCTGATGGGGCTGGTGTTATTCTCTGTATTGAGAGAGCGTTAGCTAGTGC
Consensus (1301) CCTGATGG GCTGGTGT ATTCT TGTATTGAGAGAGC TT GCT  TGC
                 1351                                             1400
AF244520  (968)  TGGGATTTCCAAAGAACAGATAAACTATATAAATGCACATGCAACCTCTA
AF318307  (1344) TGGGATTTCCAAGGAACAAATAAATTACATAAATGCACATGCAACCTCAA
Consensus (1351) TGGGATTTCCAA GAACA ATAAA TA ATAAATGCACATGCAACCTC A
                 1401                                             1450
AF244520  (1018) CACCAGCTGGAGACCTTAAGGAGTACCAAGCCCTTGCTCACTGCTTTGGC
AF318307  (1394) CGCATGCTGGAGATATTAAGGAATACCAAGCCCTTGCTCACTGTTTTGGC
Consensus (1401) C C  GCTGGAGA  TTAAGGA TACCAAGCCCTTGCTCACTG TTTGGC
                 1451                                             1500
AF244520  (1068) CAAAATCCTGAGATAAAAGTTAATTCCACAAAATCTATGATTGGACACTT
AF318307  (1444) CAAAATCCTGAGCTTAAGGTAAATTCCACAAAATCTATGATTGGACACTT
Consensus (1451) CAAAATCCTGAG T AA GT AATTCCACAAAATCTATGATTGGACACTT
                 1501                                             1550
AF244520  (1118) GCTGGGAGCTGCTGGGGCCGTTGAAGCTGTCGCAACTGTGCAGGCCATAA
AF318307  (1494) GCTGGGAGCTGCTGGGGCCGTGGAGGCTGTTGCAACTGTGCAGGCGATAC
Consensus (1501) GCTGGGAGCTGCTGGGGCCGT GA GCTGT GCAACTGTGCAGGC ATA
                 1551                                             1600
AF244520  (1168) GGACCGGATGGGTTCATCCAAATATCAACCTTGAGAGTCCAGACAATGGA
AF318307  (1544) GGACCGGATGGGTTCATCCAAATATCAACCTCGAGAATCCAGACAGTGGA
Consensus (1551) GGACCGGATGGGTTCATCCAAATATCAACCT GAGA TCCAGACA TGGA
                 1601                                             1650
AF244520  (1218) GTGGATACAAATTTGCTGGTGGGTCCTGAGAAGGAGAGATTGGACATTAA
AF318307  (1594) GTGGATACAAAGCTGCTGGTGGGTCCTAAGAAGGAGAGACTGGACATTAA
Consensus (1601) GTGGATACAAA  TGCTGGTGGGTCCT AGAAGGAGAGA TGGACATTAA
                 1651                                             1700
AF244520  (1268) AGCAGCCTTGTCAAATTCATTCGGGTTTGGTGGCCACAACTCCAGCATCA
AF318307  (1644) AGCAGCCTTGTCAAATTCATTCGGGTTTGGTGGTCATAACTCCAGCATCA
Consensus (1651) AGCAGCCTTGTCAAATTCATTCGGGTTTGGTGG CA AACTCCAGCATCA
                 1701                                             1750
AF244520  (1318) TTTTTGCTCCTTACAAGTGAAAGC--ACTCA-TTGCTGTACTCCAAACC
AF318307  (1694) TTTTTGCTCCTTACAAGTGAAAGCGAAAGCAGTTGCTTGTACTCCAAACC
Consensus (1701) TTTTTGCTCCTTACAAGTGAAAGC  A  CA TTGC TGTACTCC
                 1751                                             1800
AF244520  (1365) TGGTTGTGTAACTTGCTGTAAGTGTTTACAAGAACTCCCCATGTTATGTT
AF318307  (1744) TGATTGTATAACTTGCTGTAAG-GT-------------------------
Consensus (1751) TG TTGT TAACTTGCTGTAAG GT
                 1801                                             1850
AF244520  (1415) GTTGCGGGAATCAACACAGTTTGTTAAACTACCAAGAGCTAAGCTAAGTT
AF318307  (1768) --------------------------------------------------
Consensus (1801)
                 1851                                             1900
AF244520  (1465) TCCTTAGGATCAAGATCCGTTTGTGCCAGAGAACTTGGACAAAGAGCAAA
AF318307  (1768) --------------------------------------------------
Consensus (1851)
                 1901                                             1950
AF244520  (1515) CGTAGCAGAGTTTGGATTTAGCTTCCGTGTGATACCTTTTGAGTGGAATC
AF318307  (1768) --------------------------------------------------
Consensus (1901)
                 1951                                             2000
```

FIG. 7C

```
AF244520  (1565)  TTTGTAGCCTTTTCTTTTTTGTAGTGTTTCATTTCTATTTGTTAATCATT
AF318307  (1768)  --------------------------------------------------
Consensus (1951)
                  2001                                            2050
AF244520  (1615)  ACAATCTGAAAATTGCCAAACCAATTCTCCGTTAAATTTAGTAACTCTAC
AF318307  (1768)  --------------------------------------------------
Consensus (2001)
                  2051                   2079
AF244520  (1665)  ACAAAAAAAAAAAAAAAAAAAAAAAAAAA
AF318307  (1768)  -----------------------------
Consensus (2051)
```

FIG. 7D

```
                  1                                                50
Seq ID 3     (1)  --------------------------------------------------
Seq ID 4     (1)  --------------------------------------------------
Seq ID 46    (1)  --------------------------------------------------
Seq ID 47    (1)  --------------------------------------------------
AC189461     (1)  --------------------------------------------------
BH723504     (1)  ACGGCACTTTACGCACCAATATATACCATATGGTAGCCAGTTAAGGGTAC
Consensus    (1)
                  51                                               100
Seq ID 3     (1)  --------------------------------------------------
Seq ID 4     (1)  --------------------------------------------------
Seq ID 46    (1)  --------------------------------------------------
Seq ID 47    (1)  --------------------------------------------------
AC189461     (1)  --------------------------------------------------
BH723504    (51)  GAAGTGATTTTCCCCTTTTCTTATGTATACAGACTCCAATTCCCCAAATT
Consensus   (51)
                  101                                              150
Seq ID 3     (1)  ----------------------------------------GAATTCGCCCTT
Seq ID 4     (1)  ----------------------------------------GAATTCGCCCTT
Seq ID 46    (1)  ----------------------------------------GAATTCGCCCTT
Seq ID 47    (1)  --------------------------------------------------
AC189461     (1)  ----------------------------------------GACATGGATATT
BH723504   (101)  TACTCTGGTCATCGAACATCGATACGTTTGTATGTATGTACGTCTTATCT
Consensus  (101)                                          GAATTCGCCCTT
                  151                                              200
Seq ID 3    (13)  CGCGGA---TCCGAACACTGCGTTTGCTGGCTTTGATGAAA---------
Seq ID 4    (13)  CGCGGA---TCCGAACACTGCGTTTGCTGGCTTTGATGAAA---------
Seq ID 46   (13)  CGCGGA---TCCGAACACTGCGTTTGCTGGCTTTGATGAAAG-------C
Seq ID 47    (1)  --------------------------------------------------
AC189461    (13)  TTCTGAGATTTGGAAGTGTGGATTTGATATAAGCAAAGCAAAGCAAGTGC
BH723504   (151)  CTGTCTC-TGGCTATCTCTGTGTGTTTTGTTGTTAATAACAGGAGG----
Consensus  (151)  CGCGGA   TCCGAACACTGCGTTTGCTGGCTTTGATGAAA
                  201                                              250
Seq ID 3    (51)  -----------ATCTTTTGACGTCTCCACGCACGAGTTTACGCATCCCA
Seq ID 4    (51)  ----ATGTATGTATCTTTTGACGTCTCCACGTACGAGTTTACGCATCCA-
Seq ID 46   (53)  TTGTATGTATGTATCTTTTGACGTCTCCACGTACGAGTTTACGCATCCA-
Seq ID 47    (1)  --------------------------------------------------
AC189461    (63)  TCGCTTGTATGTATCTTTTGACGTCTCCACGCACGAGTTTACGCATCCA-
BH723504   (196)  -TTTTGTTTTGTTTTCTTTGACGTCTCCACGCACGATTTTAAGCCTCCGT
Consensus  (201)          TGTATGTATCTTTTGACGTCTCCACGCACGAGTTTACGCATCCA
                  251                                              300
Seq ID 3    (89)  GACGCCTCGTTAGAGAGAAGAGAGAGATCGAGATCGATTTCCTC--CCTC
Seq ID 4    (96)  GACGCCTCGTTAGAGAGAAGAGAGAGATCGAGATCGAGATCGAGATCGAT
Seq ID 46  (102)  GACGCCTCGTTAGAGAGAAGAGRGAGATCGAGATCGAGATCGAGATCGAT
Seq ID 47    (1)  --------------------------------------------------
AC189461   (112)  GACGCCTCGTTAGAGAGAAGAGAGAGATCGAGATCGAT-TCCTC--CCTC
BH723504   (245)  TACGCTCTGCACGCCTCCTGAAAGAGAGAGAGAGAGATCGAA-TCATC
Consensus  (251)  GACGCCTCGTTAGAGAGAAGAGAGAGATCGAGATCGAGATCGA  TC TC
                  301                                              350
```

FIG. 8A

```
Seq ID  3   (137) TTAAACCTCTCTCTCTCTCGTGAATCTCATTTCCCTTTGCCGCT-AGATT
Seq ID  4   (146) TTCCTCC-CTCTCTCTCTCGTGAATCTCATTTCCCCTTACCGCT-AGATT
Seq ID 46   (152) TTCCTCC-CTCTCTCTCTCGTGAATCTCATTTCCCCTTACCGCTA-GATT
Seq ID 47     (1) --------------------------------------------------
AC189461    (159) TTAAACCTCTCTCTCTCTCGTGAATCTCATTTCCCCTTACCGCT-AGATT
BH723504    (294) TTAATTA--AACTCTCTCGTGAA--T------C-----CGCT-AGATT
Consensus   (301) TTAATCC CTCTCTCTCTCGTGAATCTCATTTCCCCTTACCGCT AGATT
                  351                                               400
Seq ID  3   (186) CTCTCTTCACCCTTTTCTCGCCCTTCCTTCCT-CTCCTCATTACTTTTTT
Seq ID  4   (194) CTCTCTTCACCCTTTTCTCGCCCTTCCTTC----TCCTCATTATTTTTT
Seq ID 46   (200) CTCTCTTCACCCTTTTCTCGCCCTTCCTTC----TCCTCATTATTTTTT
Seq ID 47     (1) --------------------------------------------------
AC189461    (208) CTCTCTTCACCCTTTTCTCGCCCTTCCTTCCTTCTCCTCATTACTTTTTT
BH723504    (327) CTCTCTTCACCGTTTTCTCGCCTCTCCTCT-----CCTCTCCATTTTGTT
Consensus   (351) CTCTCTTCACCCTTTTCTCGCCCTTCCTTC    TCCTCATTATTTTTT
                  401                                               450
Seq ID  3   (235) GTCGTCTTCTGCTCTCTCTC-TCTCTC-AGCACTC-----TTCGCCATG
Seq ID  4   (240) GTCGTCTTCTGCTCTCTCACAGCACTC-TTCTCT-----TTAGCTATG
Seq ID 46   (246) GTCGTCTTCTGCTCTCTCWCAKCWCTC-WKCWCTC-----TTMGCYATG
Seq ID 47     (1) -------------------ACTC-AGCACTC-----TTCGCCATG
AC189461    (258) GTCGTCTTCTGCTCTCTCTC-TCTCTC-AGCACTCTTCGCTTTAGCTATG
BH723504    (372) -T--TCTTCTTCTTCGTCTTCTCTTCTTGCCAT--------GCCATG
Consensus   (401) GTCGTCTTCTGCTCTCTCTC TC CTC AGCACTC       TT GCCATG
                  451                                               500
Seq ID  3   (277) GTGGGTGCTGCTGCGTCTTC---CTGTTACGCATCTCCGCTATGCACCTG
Seq ID  4   (282) GTGGGTGGTGCTGCGTCTTCTTCCTGTTACGCATCTCCGCTATGCACCTG
Seq ID 46   (289) GTGGGTGSTGCTGCGTCTTCTTCCTGTTACGCATCTCCGCTATGCACCTG
Seq ID 47    (21) GTGGGTGCTGCTGCGTCTTC---CTGTTACGCATCTCCGCTATGCACCTG
AC189461    (306) GTGGGTGCTGCTGCGTCTTC---CTGCTACGCATCTCCGCTATGCACCTG
BH723504    (410) GTGGGTGCTGCTGCGTCTTC---CTGTTACGCATCTCCCTTATGCACCTT
Consensus   (451) GTGGGTGCTGCTGCGTCTTC   CTGTTACGCATCTCCGCTATGCACCTG
                  501                                               550
Seq ID  3   (324) GTTCGTCGCCGCCTGCATGTCCGTCTCCCACGGCGGCGGAGATTCCCGAC
Seq ID  4   (332) GTTCGTCGCTGCTTGCATGTCCGTCTCCCACGGCGGCGGAGATTCCCGAC
Seq ID 46   (339) GTTCGTCGCYGCYTGCATGTCCGTCTCCCACGGCGGCGGAGATTCCCGAC
Seq ID 47    (68) GTTCGTCGCCGCCTGCATGTCCGTCTCCCACGGCGGCGGAGATTCCCGAC
AC189461    (353) GTTCGTCGCTGCCTGCATGTCCGTCTCCCACGGCGGCGGTGATACCCGTC
BH723504    (457) CTTCGTTGCTGCTTGCATGTCCTCTCTCACGGCGGCGGTGATACCCGTC
Consensus   (501) GTTCGTCGCTGCCTGCATGTCCGTCTCCCACGGCGGCGGAGATTCCCGAC
                  551                                               600
Seq ID  3   (374) AAGCCGTCGCTCTCAAATCTACCGGGCGGAGTCGTCGAAGCAGACAACAG
Seq ID  4   (382) AAGCCGTCTCCCTCAAATCTACCGGGCGGAGTCGTCGAAGCAGACGACAG
Seq ID 46   (389) AAGCCGTCKCYCTCAAATCTACCGGGCGGAGTCGTCGAAGCAGACAACAG
Seq ID 47   (118) AAGCCGTCGCTCTCAAATCTACCGGGCGGAGTCGTCGAAGCAGACAACAG
AC189461    (403) AAGCCGTCGCTCTCAAATCTAGCGGGCGGAGTCGTCGAAGCAGACAACAA
BH723504    (507) AAGCCTT-T-----------GGGCGGAGCCGTCGAAGGAGACAACAG
Consensus   (551) AAGCCGTCGCTCTCAAATCTACCGGGCGGAGTCGTCGAAGCAGACAACAG
                  601
```

FIG. 8B

```
Seq ID 3    (424) CTCACCAAATGCT---------CTGGATCCGGTAGCAG------------
Seq ID 4    (432) CTCACCAAATGCTTGGCTCTTTCTGGATCCGGTAGCGTT---CAGGAGGC
Seq ID 46   (439) CTCACCAAATGCT---------CTGGATCCGGTAGCAG------------
Seq ID 47   (168) CTCACCAAATGCT---------CTGGATCCGGTAGCAG------------
AC189461    (453) CTCACCAAATGCT---------CTGGATCCGGTAGCAGCGTTCAGCAGGC
BH723504    (542) CTCGGCAAATGCT---------CTGGATCCGGTAGCATTCTCGTGTCTTC
Consensus   (601) CTCACCAAATGCT         CTGGATCCGGTAGCAG    G     C
                  651                                               700
Seq ID 3    (453) ------CACTACTTCCTTTGGGCCTTGCAATCACTACAAT----------
Seq ID 4    (479) TCTCGTCACTACTTCCTTTGGGCCTTGCAATCACTACAAT----------
Seq ID 46   (468) ------CACTACTTCCTTTGGGCCTTGCAATCACTACAAT----------
Seq ID 47   (197) ------CACTACTTCCTTTGGGCCTTGCAATCACTACAAT----------
AC189461    (494) TCTCGTCACTACTTCCTTTGGGCCTTGCAATCACTACAAT----------
BH723504    (583) ------TTGTTTGGAGTTTAAGCCTTGCAGTCACTACAACAAGAACAACA
Consensus   (651)       CACTACTTCCTTTGGGCCTTGCAATCACTACAAT
                  701                                               750
Seq ID 3    (487) ---GCCTTGTCTT--CTCTCTTCGGATCGAACTCTGTTTCTCTCAATCGA
Seq ID 4    (519) ---GCCTTGTCTT--CTCTCTTCGGATCGAACTCTGTTTCTCTCAATCGA
Seq ID 46   (502) ---GCCTTGTCTT--CTCTCTTCGGATCGAACTCTGTTTCTCTCAATCGA
Seq ID 47   (231) ---GCCTTGTCTT--CTCTCTTCGGATCGAACTCTGTTTCTCTCAATCGA
AC189461    (534) ---GCCTTGTCTT--CTCTCTTCGGATCGAACTCTGTTTCTCTCAATCGA
BH723504    (627) AAGGCAATGCTTTCCTCTCCTCGGATCGAATAGCCTTTCTCTGAATCGA
Consensus   (701)    GCCTTGTCTT    CTCTCTTCGGATCGAACTCTGTTTCTCTCAATCGA
                  751         FWD----------                         800
Seq ID 3    (532) AACCAGAGGAGGTTGACTCGAGCTGCTACTGCTAGTTCCGGTGGAGGAGC
Seq ID 4    (564) AACCAGAGGAGGTTGAATCTGGCTG---CTGCTAGTTCCGGTGGAGGAGC
Seq ID 46   (547) AACCAGAGGAGGTTGAMTCGWGCTGCTRCTGCTAGTTCCGGTGGAGGAGC
Seq ID 47   (276) AACCAGAGGAGGTTGACTCGAGCTGCTACTGCTAGTTCCGGTGGAGGAGC
AC189461    (579) AACCAGAGGAGGTTGACTCGAGCTGCTACTGCTAGTTCCGGTAATTTAAC
BH723504    (677) AAGCAGAGGAAACTGAATCGAGCAACTTCTTCTTCTTCCGGTATAAACAT
Consensus   (751) AACCAGAGGAGGTTGACTCGAGCTGCTACTGCTAGTTCCGGTGGAGGAGC
                  801                          ---------REV          850
Seq ID 3    (582) ------C---ATGGCTGTTGCGATGGATA-TGAAAAGGAAGCCAAGGTT
Seq ID 4    (611) ------C---ATGGCTGTTGCGATGGATA-TGCAAAAGGAAGCCAAGGTT
Seq ID 46   (597) ------C---ATGGCTGTTGCGATGGATA-TGCAAAAGGAAGCCAAGGTT
Seq ID 47   (326) ------C---ATGGCTGTTGCGATGGATA-TGAAAAGGAAGCCAAGGTT
AC189461    (629) ATTTCAC---CAATCTGGGTTTTTGATTTGTGGGTATTGTTTGCAGAGTT
BH723504    (727) TCTTCTCCCAAAATCTCAAGTCTTGGTTTCTGGGTATCGTTTGCAA-GCT
Consensus   (801)       C   ATGGCTGTTGCGATGGATA TGGAAAAGGAAGCCAAGGTT
                  851                                               900
Seq ID 3    (622) GACAACAAACCTCCTACG-GAGCAGCG---CCGGGTTGTTGTGACAGGCA
Seq ID 4    (651) GACAACAAACCCCCTACG-GAGCAGCG---CCGTGTTGTGGTGACAGGCA
Seq ID 46   (637) GACAACAAACCCCCTACG-GAGCARCG---CCGTGTTGTGGTGACAGGCA
Seq ID 47   (366) GACAACAAACCTCCTACG-GAGCAGCG---CCGGGTTGTTGTGACAGGCA
AC189461    (676) GACAAGCTTTGTTTTTGT-TAGTAAAGTTTCTCTTTTATGTGTTTATGT
BH723504    (776) GACAAGCTTTGTTTTTGTGTATAAAGTTTCTCCTTT--------------
Consensus   (851) GACAACAAACCTCCTACG GAGCAGCG   CCGTGTTGTTGTGACAGGCA
                  901                                               950
```

FIG. 8C

```
Seq ID 3     (668)  TGGGAGTTGAAACATCACTAGGTCATGACCCTGACACCTTTTATGAGAAT
Seq ID 4     (697)  TGGGAGTTGAAACATCACTAGGTCAAGGGCGAATTC--------------
Seq ID 46    (683)  TGGGAGTTGAAACATCACTAGGTCAAGGGCGAATTC--------------
Seq ID 47    (412)  TGGGAGTTGAAACATCACTAGGTCAAGGGCGAATTC--------------
AC189461     (725)  TATTTGGTCAAATGATTCAACTTGGAGATCAAGTTTAACGGGAAAGTATG
BH723504     (813)  --------------------------------------------------
Consensus    (901)  TGGGAGTTGAAACATCACTAGGTCAAGGGCGAATTC
                    951                                               1000
Seq ID 3     (718)  CTCCTACAAGGGCGAATTC-------------------------------
Seq ID 4     (733)  --------------------------------------------------
Seq ID 46    (719)  --------------------------------------------------
Seq ID 47    (448)  --------------------------------------------------
AC189461     (775)  CTGATTTGGAATCTCAGCTTAATTGTCAAGTTTCATTCTTTATTGTGTGT
BH723504     (813)  --------------------------------------------------
Consensus    (951)
                    1001                                              1050
Seq ID 3     (737)  --------------------------------------------------
Seq ID 4     (733)  --------------------------------------------------
Seq ID 46    (719)  --------------------------------------------------
Seq ID 47    (448)  --------------------------------------------------
AC189461     (825)  GTAATATGCAAAGCACATTTCTGTGAGTTTGATTCAATATTGGACTCTAG
BH723504     (813)  --------------------------------------------------
Consensus   (1001)
                    1051         1069
Seq ID 3     (737)  ------------------
Seq ID 4     (733)  ------------------
Seq ID 46    (719)  ------------------
Seq ID 47    (448)  ------------------
AC189461     (875)  ATAAGGAGTATGATGATAC
BH723504     (813)  ------------------
Consensus   (1051)
```

FIG. 8D

ENGINEERED ZINC FINGER PROTEINS TARGETING PLANT GENES INVOLVED IN FATTY ACID BIOSYNTHESIS

CROSS-REFERENCE TO RELATED APPLICATIONS

The application claims the benefit of U.S. Provisional Application No. 61/279,528, filed Oct. 22, 2010, the disclosure of which is hereby incorporated by reference in its entirety herein.

TECHNICAL FIELD

The disclosure relates generally to the fields of genome engineering and protein expression in plants. In particular, the present disclosure relates to engineered DNA-binding domains, for example, zinc finger proteins, that target genes involved in fatty acid synthesis and methods of using such zinc finger proteins in modulating gene expression, gene inactivation, and targeted gene modification to generate plants with altered fatty acid profiles.

BACKGROUND

Diets high in saturated fats increase low density lipoproteins (LDL), which in turn causes the deposition of cholesterol on blood vessels, a pre-condition closely correlated with atherosclerosis and coronary heart disease (Conner et al., Coronary Heart Disease: Prevention, Complications, and Treatment, J. B. Lippincott, Philadelphia, 1984 pp. 43-64,). By contrast, diets high in monounsaturated fats have been shown to reduce heart disease. Oleic acid, the only monounsaturated fat in most edible vegetable oils, lowers LDL as effectively as linoleic acid, but does not affect high density lipoproteins (HDL) levels (Mensink et al. (1989) *New England J. Med.*, 321:436-441). Furthermore, diets high in monounsaturated fats are also correlated with reduced systolic blood pressure (Williams et al. (1987) *J. Am. Med. Assoc.*, 257:3251-3256, 1987).

In light of the effect of fatty acids on diet and health, attempts have been made to alter the fatty acid profile of plants used for edible and industrial purposes. However, conventional methods of altering plants to improve the fatty acid profile rely on mutagenesis (e.g., chemical, radiation, etc.) and/or breeding and are time-consuming, laborious and do not specifically target selected genes. See, e.g., U.S. Pat. No. 5,861,187.

Recently, engineered DNA-binding domains such as meganuclease DNA-binding domains and zinc fingers proteins (ZFPs) have been used advantageously to selectively modulate gene expression and for targeted alteration of gene sequences in plants (see, e.g., U.S. Pat. Nos. 7,262,054, 7,235,354, 7,220,719, 7,001,768, and 6,534,261; U.S. Patent Publication Nos. 2008/0182332 and U.S. Ser. No. 12/284, 888). Zinc finger proteins (ZFPs) are proteins that bind to DNA, RNA and/or protein, in a sequence-specific manner, by virtue of a metal stabilized domain known as a zinc finger. See, for example, Miller et al. (1985) *EMBO J.* 4:1609-1614; Rhodes et al. (1993) *Sci. Amer.* 268(2):56-65; and Klug (1999) *J. Mol. Biol.* 293:215-218. ZFPs are commonly found in transcription factors, and to date, over 10,000 zinc finger sequences have been identified in several thousand known or putative transcription factors.

DNA-binding domains can also be used with nuclease domains to make engineered nucleases. For example, the DNA-binding domain of a homing endonuclease can be altered to generate novel homing endonucleases. Similarly, zinc finger domains have also been combined with nuclease cleavage domains to produce zinc finger nucleases (ZFNs) for specific targeting of a double-stranded break to the region of a genome where modification (e.g., deletion, mutation, homologous recombination, or insertion of an exogenous sequence) is desired (see, e.g., U.S. Patent Application Publication Nos. 2007/0134796; 2005/0064474; 2008/0182332). Engineered ZFPs greatly facilitate the insertion of exogenous sequences or modification of endogenous sequences at specific target sites in plants and provide for targeted alteration of plant genomes with greater efficiencies than conventional methods (see, e.g., U.S. Pat. Nos. 7,262,054, 7,235,354, 7,220,719, 7,001,768, and 6,534,261).

Nonetheless, there remains a need for compositions and methods for targeted alteration of genes involved in fatty acid synthesis in order to produce plants and plant products (e.g., plant oils) having selected fatty acids. By producing plant varieties with reduced levels of individual and total saturated fats in the seed oil, oil-based food products which contain less saturated fats can be produced. Such products will benefit public health by reducing the incidence of atherosclerosis and coronary heart disease.

SUMMARY

The present disclosure provides compositions and methods for modulating expression and for targeted alteration in whole plants or plant cells of one or more plant genes involved in fatty acid biosynthesis, thereby altering the fatty acid composition in the whole plant or plant cells. Whole plants or plant cells can be from monocotyledonous (monocots) or dicotyledonous (dicots) plant species, including in some particular embodiments oil-producing plants, and also include cultured cells, cells in a plant at any stage of development, and plant cells that have been removed from a whole plant and which cells (or their descendants) will be regenerated into plants. Plant cells can contain one or more homeologous or paralogous gene sequences, any number of which or all of which can be targeted for modification by the methods disclosed herein.

In one aspect, described herein is a DNA-binding domain (e.g., zinc finger protein (ZFP)) that specifically binds to a gene involved in a plant fatty acid biosynthesis pathway. In some embodiments, the gene is a *Brassica napus* gene. In some particular embodiments, the *Brassica napus* gene can encode Acetyl-COA carboxylase (ACCase), β-ketoacyl-ACP synthetases (KAS, e.g., KAS I-KAS IV), Fatty acid thioesterase B (FATB, e.g., FATB1-FATB5, or other plastidial thioesterases), Fatty acid synthase (FAS), Fatty acid elongase (FAE, e.g., FAE1), Fatty acid thioesterase A (FatA), Fatty acid desaturase (Fad2, Fad3), plastidial G-3-P dehydrogenase (GPDH), glycerokinase (GK), stearoyl-acyl carrier protein desaturase (S-ACP-DES), and oleoyl-ACP hydrolase. In some particular embodiments, the gene can be an ortholog or a homolog of these genes in other oil-producing plant species.

In a still further aspect, fusion proteins comprising any of the DNA-binding domains (e.g., ZFPs) described herein are also provided. In certain embodiments, the fusion protein comprises a zinc finger protein and a transcriptional regulatory domain (e.g., activation or repression domain), also known as a ZFP TF. In other embodiments, the fusion protein comprises a ZFP and a nuclease domain to form a zinc finger nuclease (ZFN) that cleaves in a genomic region of interest with the target gene. In certain embodiments, the ZFN comprises a fusion polypeptide comprising an engineered zinc finger binding domain having specificity for a gene involved in a plant fatty acid biosynthesis pathway (e.g., a gene encoding ACCase, KAS I, KAS II, KAS III, KAS IV, FATB1, FATB2, FATB3, FATB4, FATB5, FAS, FAE1, FatA, Fad2, Fad3, GPDH, GK, or S-ACP-DES) and a cleavage domain, and/or one or more fusion polypeptides comprising an engineered zinc finger binding domain and a cleavage half-domain. In certain embodiments, the zinc finger binding domains bind to a target site as shown in Table 2 or Table 10A. In certain embodiments, the zinc finger binding domains comprise a sequence selected from the group consisting of zinc finger proteins comprising the recognition domains (e.g., a single row) shown in Table 1 or Table 10B. Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In other aspects, provided herein are polynucleotides encoding any of the DNA-binding domains (e.g., zinc finger proteins) and/or fusion proteins described herein. In certain embodiments, described herein is a ZFP expression vector comprising a polynucleotide, encoding one or more ZFPs described herein, operably linked to a promoter. In one embodiment, one or more of the ZFPs are ZFNs.

The ZFPs and fusion proteins comprising these ZFPs may bind to and/or cleave a gene involved in fatty acid synthesis within the coding region of the gene or in a non-coding sequence within or adjacent to the gene, such as, for example, a leader sequence, trailer sequence or intron, or within a non-transcribed region, either upstream or downstream of the coding region. In certain embodiments, the ZFPs or ZFNs bind to and/or cleave a coding sequence or a regulatory sequence of a gene involved in fatty acid biosynthesis.

In another aspect, described herein are compositions comprising one or more proteins, fusion proteins or polynucleotides as described herein. Plant cells may contain one unique gene target or multiple paralogous copies of the same gene. Thus, compositions may comprise one or more ZFP-containing proteins (and polynucleotides encoding same) that target one or more genes involved in fatty acid synthesis in a plant cell. The ZFPs may target all paralogous or homeologous genes and selected particular paralogous or homeologoug genes in a plant cell or a combination thereof.

In another aspect, provided herein is a plant host cell comprising one or more proteins or polynucleotides (e.g., ZFP expression vectors) as described herein. For polynucleotides, the plant host cell may be stably transformed or transiently transfected or a combination thereof with one or more ZFP expression vectors. In'one embodiment, the one or more ZFP expression vectors express one or more ZFNs in the plant host cell. In another embodiment, the one or more ZFP expression vectors express one or more ZFP TFs in the plant host cell.

In another aspect, described herein is a method for modulating expression of one or more genes involved in fatty acid biosynthesis in a plant cell, the method comprising: (a) introducing, into the plant cell, one or more expression vectors encoding one or more ZFP TFs that bind to a target site in the one or more genes involved in fatty acid biosynthesis under conditions such that the ZFP TFs is (are) expressed and expression of the one or more genes is modulated. Modulation may be activation or repression. In certain embodiments, at least one target site is in a ACCase, KAS I, KAS II, KAS III, KAS IV, FATB1, FATB2, FATB3, FATB4, FATB5, FAS, FAE1, FatA, Fad2, Fad3, GPDH, GK, and/or S-ACP-DES gene(s). In other embodiments, more than one gene involved in fatty acid biosynthesis is modulated. In any of the methods of modulating expression of genes involved in fatty acid biosynthesis as described herein, the methods result in plant cells with modified fatty acid content, for example, a reduction of the amount of saturated fats in the plant cells. In some embodiments, the modified fatty acid content in the plant cells results in a modified fatty acid content in the seeds of the plant, for example, a reduction of the amount of saturated fats in the seeds of the plant. In some embodiments the plant an oil-producing plant with modified fatty acid consent in the seeds of the oil-producing plant (e.g., reduced saturated fats). In some particular embodiment, the plant is a *Brassica napus* plant with modified fatty acid consent in the seeds of the *Brassica napus* plant (e.g., reduced saturated fats).

In another aspect, described herein is a method for cleaving one or more genes involved in fatty acid biosynthesis in a plant cell, the method comprising: (a) introducing, into the plant cell, one or more expression vectors encoding one or more nucleases (e.g., ZFNs) that bind to a target site in the one or more genes involved in fatty acid biosynthesis under conditions such that the nucleases (e.g., ZFN(s)) is (are) expressed and the one or more genes are cleaved. In certain embodiments, at least one target site is in a gene encoding ACCase, KAS I, KAS II, KAS III, KAS IV, FATB1, FATB2, FATB3, FATB4, FATB5, FAS, FAE1, FatA, Fad2, Fad3, GPDH, GK, and/or S-ACP-DES. In other embodiments, more than one gene involved in fatty acid biosynthesis is cleaved. Furthermore, in any of the methods described herein, cleavage of the one or more genes may result in deletion, addition and/or substitution of nucleotides in the cleaved region.

In yet another aspect, described herein is a method for introducing an exogenous sequence into the genome of a plant cell, the method comprising the steps of: (a) contacting the cell with an exogenous sequence (donor vector); and (b) expressing one or more nucleases (e.g., zinc finger nucleases) as described herein in the cell, wherein the one or more nucleases cleave chromosomal DNA; such that cleavage of chromosomal DNA in step (b) stimulates incorporation of the donor vector into the genome by homologous recombination. In certain embodiments, the one or more nucleases are fusions between the cleavage domain of a Type IIs restriction endonuclease and an engineered zinc finger binding domain. In other embodiments, the nuclease comprises a homing endonuclease, for example a homing endonuclease with a modified DNA-binding domain. In any of the methods described herein, the exogenous sequence may encode a protein product.

In a still further aspect, a transgenic or a non-transgenic plant cell obtained according to any of the methods described herein is also provided.

In another aspect, provided herein is a plant comprising a transgenic or a non-transgenic plant cell obtained as described herein.

In another aspect, provided herein is a seed from a plant comprising a transgenic or non-transgenic plant cell obtained as described herein.

In another aspect, provided herein is oil from a seed extracted from a plant comprising a transgenic or non-transgenic plant cell obtained as described herein.

BRIEF DESCRIPTION OF THE DRAWINGS

FIG. 7 depicts a sequence alignment of AF318307 (SEQ ID NO: 94) and AF244520 (SEQ ID NO: 93). Shading indicates regions of exact homology.

FIG. 8 depicts a sequence alignment of SEQ ID NO:3, SEQ ID NO:4, SEQ ID NO:46, SEQ ID NO:30, AC189461 (SEQ ID NO: 95), and BH723504 (SEQ ID NO: 96). Forward and reverse primer sequences (SEQ ID NOs 28 and 29) for amplification of the β-ketoacyl-ACP synthetase II cDNA are highlighted by broken lines above the corresponding sequence. Shading indicates regions of exact homology.

DETAILED DESCRIPTION

Figure 1:
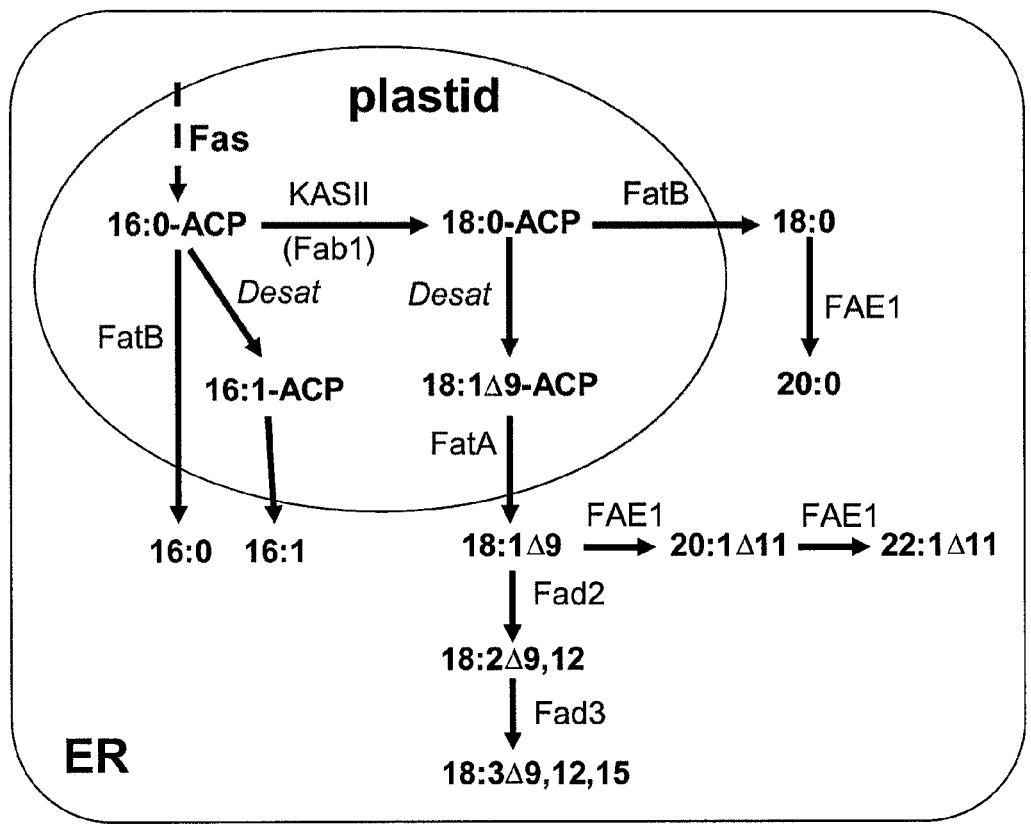
FIG. 1 is a schematic depicting fatty acid biosynthesis pathways in canola (*B. napus*). This was adapted as per John Shanklin, Brookhaven National Laboratory, Upton, N.Y. (Thelen and Ohlrogge, 2002, *Metabolic engineering* 4:12-21).

Disclosed herein are compositions and methods useful for modulation of expression and targeted cleavage and alteration of one or more genes involved in fatty acid synthesis in plants. Regulation of such genes can be modulated, e.g., by using engineered ZFP transcription factors or modifying gene regulatory regions. Genes can be altered, e.g., by targeted cleavage followed by intrachromosdmal homologous recombination or by targeted cleavage followed by homologous recombination between an exogenous polynucleotide (comprising one or more regions of homology with the gene nucleotide sequence) and a genomic sequence.

Genomic sequences include those present in chromosomes, episomes, organellar genomes (e.g., mitochondria, plastids), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, translocations, rearrangements, and/or point mutations. A genomic sequence can also comprise one of a number of different alleles.

Compositions disclosed herein comprise one or more ZFPs comprising engineered zinc finger binding domains, polynucleotides encoding these polypeptides, and combinations of ZFPs and ZFP-encoding polynucleotides. A zinc finger binding domain can comprise one or more zinc fingers (e.g., 2, 3, 4, 5, 6, 7, 8, 9 or more zinc fingers), and can be engineered to bind to any genomic sequence of a gene, including regulatory sequences operatively linked to the gene, involved in fatty-acid biosynthesis.

ZFPs as described herein can be used to regulate gene expression, either through activation or repression of gene transcription. ZFPs comprising fusions of zinc finger domains linked to regulatory domains can be constructed to create chimeric transcription factors that activate or repress transcription. ZFPs can also be used for targeted cleavage of a genomic region of interest by linking zinc finger domains with nuclease cleavage domains (or cleavage half-domains) to produce zinc finger nucleases. Thus, by identifying a target genomic region of interest at which gene regulation, cleavage, or recombination is desired, one can, according to the methods disclosed herein, construct a zinc finger protein comprising one or more fusion proteins comprising one or more regulatory domains and/or cleavage domains (or cleavage half-domains) linked to a zinc finger domain engineered to recognize a gene sequence in that genomic region. The presence of such a ZFP comprising a fusion protein (or proteins) in a cell will result in binding of the fusion protein(s) to its (their) binding site(s) and altered regulation or cleavage within or near the genomic region. Additionally, if a genomic region is cleaved and an exogenous polynucleotide homologous to that genomic region is also present in the cell, homologous recombination occurs at a high rate between the genomic region and the exogenous polynucleotide.

As shown in FIG. 1, there are several genes that are involved in fatty acid biosynthesis. Thus, compositions described herein may target one or more of these genes in a plant cell, including but not limited to ACCase, KAS I, KAS II, KAS III, KAS IV, FATB1, FATB2, FATB3, FATB4, FATB5, FAS, FAE1, FatA, Fad2, Fad3, GPDH, GK, or S-ACP-DES gene(s) and orthologs, paralogs, and homeologs of these genes. For example, 1, 2, 3, 4, 5, or more genes involved in fatty acid biosynthesis can be targeted by proteins (e.g., ZFPs) disclosed herein. Therefore, one or more ZFPs or expression vectors encoding ZFPs of different specificities may be combined to target the desired genes of interest in a plant.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower IQ.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence (e.g., a target sequence in any gene involved in fatty acid biosynthesis). Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 6,785,613; see, also WO 98/53058; WO 98/53059; WO 98/53060; WO 02/016536 and WO 03/016496; and U.S. Pat. Nos. 6,746,838; 6,866,997; and 7,030,215. Thus, an "engineered" zinc finger protein or "non-naturally occurring" zinc finger protein is one in which one or more of the component zinc finger DNA binding domains (recognition helices) are not naturally occurring and have been engineered to bind to a pre-selected target site.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 6,733,970; U.S. Pat. No. RE. 39,229; and WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 25,000 nucleotides in length (or any integer value therebetween or thereabove), preferably between about 100 and 5,000 nucleotides in length (or any integer therebetween), more preferably between about 200 and 2,500 nucleotides in length.

A "homologous sequence" refers to a first sequence which shares a degree of sequence identity with a second sequence, and whose sequence may be identical to that of the second sequence. A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, by utilizing normal cellular mechanisms. Two homologous non-identical sequences can be of any length and their degree of non-homology can be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 35% to 100% and any integer value therebetween. Typically the percent identities between sequences are at least 35%-40%; 40%-45%; 45%-50%; 50%-60%; 60%-70%; 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have, a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule for template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence, which in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged-into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, an *Agrobacterium tumefaciens* T-strand, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. The exogenous molecule non-plant molecule, for example, a mammalian (e.g., human or humanized) antibody.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a ZFN comprising a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development. Therefore, plant cells may be cells from seeds of the plant. In some embodiments, the plant or plant cell is, or is derived from, a plant involved in the production of vegetable oils for edible and/or industrial uses (i.e., an "oil-producing plant"). Exemplary oil-producing plants include, but are not limited to, *Brassica* sp. (e.g., *Brassica napus* including canola cultivars), maize, soybean, *crambe*, mustard, castor bean, peanut, sesame, cotton, linseed, safflower, oil palm, flax, sunflower, and coconut.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 25,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a regulatory domain, the ZFP DNA-binding domain and the regulatory domain are in operative linkage if, in the fusion polypeptide, the ZFP DNA-binding domain portion is able to bind its target site and/or its binding site, while the regulatory domain is able to regulate expression of DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the correspOnding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

As used herein, "saturated fatty acids" include, but are not limited to, lauric (C12:0), myristic (C14:0), palmitic (C16:0) and stearic (C18:0) acids. Similarly, "monounsaturated fatty acids" and "polyunsaturated fatty acids" include, but are not limited to, C18 fatty acids such as oleic acid (C18:1), reduced linoleic acid (C18:2) and reduced linolenic acid (C18:3).

Target Sites

The disclosed methods and compositions include fusion proteins comprising a DNA-binding domain (e.g., ZFP) and a regulatory domain or cleavage (nuclease) domain (or a cleavage half-domain), in which the DNA-binding domain (e.g., zinc finger domain), by binding to a sequence in cellular chromatin in a gene involved in fatty acid synthesis, directs the activity of the transcriptional regulatory domain or cleavage domain (or cleavage half-domain) to the vicinity of the sequence and, hence, modulates transcription or induces cleavage in the vicinity of the target sequence.

As set forth elsewhere in this disclosure, a zinc finger domain can be engineered to bind to virtually any desired sequence. Accordingly, after identifying a region of interest containing a sequence at which gene regulation, cleavage, or recombination is desired, one or more zinc finger binding domains can be engineered to bind to one or more sequences in the region of interest.

Selection of a target site in a genomic region of interest in cellular chromatin of any gene involved in fatty acid biosynthesis (e.g., see FIG. 1) for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

In certain embodiments, the ZFPs as described herein bind to a target site in a gene encoding ACCase, KAS I, KAS II, KAS III, KAS N, FATB1, FATB2, FATB3, FATB4, FATB5, FAS, FAE1, FatA, Fad2, Fad3, GPDH, GK, and/or S-ACP-DES.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a β-nucleotide sequence, wherein the thirteenth nucleotide is part of a quadruplet bound by a terminal finger, etc.

The length and nature of amino acid linker sequences, between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a β-nucleotide target site comprising, in sequence, two contiguous 3-nucleotide subsites, an intervening nucleotide, and two contiguous triplet subsites. See, also, U.S. Application No. 61/130,099 for compositions and methods for linking artificial nucleases to bind to target sites separated by different numbers of nucleotides. Distance between sequences (e.g., target sites) refers to the number of nucleotides or nucleotide pairs intervening between two sequences, as measured from the edges of the sequences nearest each other.

In certain embodiments, ZFPs with transcription factor function are designed. For transcription factor function, simple binding and sufficient proximity to the promoter are all that is generally needed. Exact positioning relative to the promoter, orientation, and within limits, distance does not matter greatly. This feature allows considerable flexibility in choosing target sites for constructing artificial transcription factors. The target site recognized by the ZFP therefore can be any suitable site in the target gene that will allow activation or repression of gene expression by a ZFP, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region.

In other embodiments, ZFPs with nuclease activity are designed. Expression of a ZFN comprising a fusion protein comprising a zinc finger binding domain and a cleavage domain (or of two fusion proteins, each comprising a zinc finger binding domain and a cleavage half-domain), in a cell, effects cleavage in the vicinity of the target sequence. In certain embodiments, cleavage depends on the binding of two zinc finger domain/cleavage half-domain fusion molecules to separate target sites. The two target sites can be on opposite DNA strands, or alternatively, both target sites can be on the same DNA strand.

DNA Binding Domains

Any DNA binding domain can be used in the practice of the present invention. In certain embodiments, the DNA binding domain comprises a zinc finger binding domain of one or more zinc fingers (Miller et al. (1985) *EMBO J.* 4:1609-1614; Rhodes (1993) *Scientific American Feb.*:56-65; U.S. Pat. No. 6,453,242). Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ and $C_2HC$ zinc fingers (those in which the zinc ion is coordinated by three cysteine residues and one histidine residue, see, e.g., U.S. Patent Publication No. 2008/0182332) and $C_4$ zinc fingers (those in which the zinc ion is coordinated by four cysteine residues). See also WO 02/057293.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered (or non-naturally occurring) zinc finger binding domain can have a novel binding specificity, compared to a naturally-occurring zinc finger protein. Engineering methods include, but are not limited to, rational design, and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261. Additional design methods are disclosed, for example, in U.S. Pat. Nos. 6,746,838; 6,785,613; 6,866,997; and 7,030,215.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned U.S. Pat. No. 6,794,136.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence.

Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) *Proc. Natl. Acad. Sci. USA* 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

In one embodiment, described herein is a zinc finger binding domain comprising an amino acid sequence as shown in Table 1. In another embodiment, the disclosure provides a polynucleotide encoding a zinc finger binding domain, wherein the zinc finger binding domain comprises an amino acid sequence as shown in Table 1.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In other embodiments, the DNA-binding domain comprises a naturally occurring or engineered (non-naturally occurring) TAL effector DNA binding domain. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet.* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 by in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 by and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). Christian et al ((2010) Genetics epub 10.1534/genetics.110.120717).

Regulatory Domains

The DNA-binding domains (e.g., ZFPs) described herein can optionally be associated with regulatory domains for modulation of gene expression. The ZFP can be covalently or non-covalently associated with one or more regulatory domains, alternatively two or more regulatory domains, with the two or more domains being two copies of the same domain, or two different domains. The regulatory domains can be covalently linked to the ZFP, e.g., via an amino acid linker, as part of a fusion protein. The ZFPs can also be associated with a regulatory domain via a non-covalent dimerization domain, e.g., a leucine zipper, a STAT protein N terminal domain, or an FK506 binding protein (see, e.g., O'Shea, Science 254: 539 (1991), Barahmand-Pour et al, *Curr. Top. Microbiol. Immunol.* 211:121-128 (1996); Klemm et al., *Annu. Rev. Immunol.* 16:569-592 (1998); Klemm et al., *Annu. Rev. Immunol.* 16:569-592 (1998); Ho et al., *Nature* 382:822-826 (1996); and Pomeranz et al., *Biochem.* 37:965 (1998)). The regulatory domain can be associated with the ZFP at any suitable position, including the C- or N-terminus of the ZFP.

Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825-30 (1996) for a review of proteins and nucleic acid elements involved in transcription; transcription factors in general are reviewed in Barnes and Adcock, *Clin. Exp. Allergy* 25 Suppl. 2:46-9 (1995) and Roeder, Methods Enzymol. 273:165-71 (1996)). Nuclear hormone receptor transcription factors are described in, for example, Rosen et al., *J Med. Chem.* 38:4855-74 (1995). The C/EBP family of transcription factors are reviewed in Wedel et al., *Immunobiology* 193:171-85 (1995). Coactivators and co-repressors that mediate transcription regulation by nuclear hormone receptors are reviewed in, for example, Meier, *Eur. J Endocrinol.* 134(2):158-9 (1996); Kaiser et al., *Trends Biochem. Sci.* 21:342-5 (1996); and Utley et al., *Nature* 394:498-502 (1998)). GATA transcription factors, which are involved in regulation of hematopoiesis, are described in, for example, Simon, *Nat. Genet.* 11:9-11 (1995); Weiss et al., *Exp. Hematol.* 23:99-107. TATA box binding protein (TBP) and its associated TAP polypeptides (which include TAF30, TAF55, TAF80, TAF 10, TAFI 50, and TAF250) are described in Goodrich and Tjian, *Curr. Opin. Cell Biol.* 6:403-9 (1994) and Hurley, *Curr. Opin. Struct. Biol.* 6:69-75 (1996). The STAT family of transcription factors are reviewed in, for example, Barahmand-Pour et al., *Curr. Top. Microbiol. Immunol.* 211:121-8 (1996). Transcription factors involved in disease are reviewed in Aso et al., *J. Clin. Invest.* 97:1561-9 (1996).

In one embodiment, the KRAB repression domain from the human KOX-1 protein is used as a transcriptional repressor (Thiesen et al., *New Biologist* 2:363-374 (1990); Margolin et al., *Proc. Natl. Acad. Sci. USA* 91:4509-4513 (1994); Pengue et al., *Nucl. Acids Res.* 22:2908-2914 (1994); Witzgall et al., *Proc. Natl. Acad. Sci. USA* 91:4514-4518 (1994)). In another embodiment, KAP-1, a KRAB co-repressor, is used with KRAB (Friedman et al., *Genes Dev.* 10:2067-2078 (1996)). Alternatively, KAP-1 can be used alone with a ZFP. Other preferred transcription factors and transcription factor domains that act as transcriptional repressors include MAD (see, e.g., Sommer et al., *J. Biol. Chem.* 273:6632-6642 (1998); Gupta et al., *Oncogene* 16:1149-1159 (1998); Queva et al., *Oncogene* 16:967-977 (1998); Larsson et al., *Oncogene* 15:737-748 (1997); Laherty et al., *Cell* 89:349-356 (1997); and Cultraro et al, *Mol. Cell. Biol.* 17:2353-2359 (19977)); FKHR (forkhead in rhapdosarcoma gene; Ginsberg et al., *Cancer Res.* 15:3542-3546 (1998); Epstein et al, *Mol. Cell. Biol.* 18:4118-4130 (1998)); EGR-1 (early growth response gene product-1; Yan et al., *Proc. Natl. Acad. Sci. USA* 95:8298-8303 (1998); and Liu et al., *Cancer Gene Ther.* 5:3-28 (1998)); the ets2 repressor factor repressor domain (ERD; Sgouras et al., *EMBO J.* 14:4781-4793 ((19095)); the MAD smSIN3 interaction domain (SID; Ayer et al., *Mol. Cell. Biol.* 16:5772-5781 (1996)); and the ERF3 (ethylene response factor-3) amphiphilic repression domain, EAR (Ohta, M., et al. (2001), *Plant Cell* 13:1959-1968).

In one embodiment, the HSV VP16 activation domain is used as a transcriptional activator (see, e.g., Hagmann et al., *J. Virol.* 71:5952-5962 (1997)). Other preferred transcription factors that could supply activation domains include the VP64 activation domain (Seipel et al., *EMBO J.* 11:4961-4968 (1996)); nuclear hormone receptors (see, e.g., Torchia et al., *Curr. Opin. Cell. Biol.* 10:373-383 (1998)); the p65 subunit of nuclear factor kappa B (Bitko and Barik, *J Virol.* 75:5610-5618 (1998) and Doyle and Hunt, *Neuroreport* 8:2937-2942 (1997)); EGR-1 (early growth response gene product-1; Yan et al., *Proc. Natl. Acad. Sci. USA* 95:8298-8303 (1998); and Liu et al., *Cancer Gene Ther.* 5:3-28 (1998)); and the maize anthocyanin biosynthetic pathway regulatory protein, C1 (S. A. Goff, et al, (1991), *Genetics and Development* 5:298-309).

Kinases, phosphatases, and other proteins that modify polypeptides involved in gene regulation are also useful as regulatory domains for ZFPs. Such modifiers are often involved in switching on or off transcription mediated by, for example, hormones. Kinases involved in transcriptional regulation are reviewed in Davis, *Mol. Reprod. Dev.* 42:459-67 (1995), Jackson et al., *Adv. Second Messenger Phosphoprotein Res.* 28:279-86 (1993), and Boulikas, *Crit. Rev. Eukaryot. Gene Expr.* 5:1-77 (1995), while phosphatases are reviewed in, for example, Schonthal and Semin, *Cancer Biol.* 6:239-48 (1995). Nuclear tyrosine kinases are described in Wang, *Trends Biochem. Sci.* 19:373-6 (1994).

As described, useful domains can also be obtained from the gene products of oncogenes (e.g., myc, jun, fos, rriyb, max, mad, rel, ets, bcl, myb, mos family members) and their associated factors and modifiers. Oncogenes are described in, for example, Cooper, Oncogenes, 2nd ed., The Jones and Bartlett Series in Biology, Boston, Mass., Jones and Bartlett Publishers, 1995. The ets transcription factors are reviewed in Waslylk et al., *Eur. J. Biochem.* 211:7-18 (1993) and Crepieux et al., *Crit. Rev. Oncog.* 5:615-38 (1994). Myc oncogenes are reviewed in, for example, Ryan et al., *Biochem. J.* 314:713-21 (1996). The jun and fos transcription factors are described in, for example, The Fos and Jun Families of Transcription Factors, Angel and Herrlich, eds. (1994). The max oncogene is reviewed in Hurlin et al., *Cold Spring Harb. Symp. Quant. Biol.* 59:109-16. The myb gene family is reviewed in Kanei-Ishii et al., *Curr. Top. Microbiol. Immunol.* 211:89-98 (1996). The mos family is reviewed in Yew et al., *Curr. Opin. Genet. Dev.* 3:19-25 (1993).

ZFPs can include regulatory domains obtained from DNA repair enzymes and their associated factors and modifiers. DNA repair systems are reviewed in, for example, Vos, *Curr. Opin. Cell Biol.* 4:385-95 (1992); Sancar, *Ann. Rev. Genet.* 29:69-105 (1995); Lehmann, *Genet. Eng.* 17:1-19 (1995); and Wood, *Ann. Rev. Biochem.* 65:135-67 (1996). DNA rearrangement enzymes and their associated factors and modifiers can also be used as regulatory domains (see, e.g., Gangloff et al., *Experientia* 50:261-9 (1994); Sadowski, *FASEB J.* 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13-22 (1994), and methyltransferases are described in Cheng, *Curr. Opin. Struct. Biol.* 5:4-10 (1995). Chromatin associated proteins and their modifiers (e.g., kinases, acetylases and deacetylases), such as histone deacetylase (Wolffe, *Science* 272:371-2 (1996)) are also useful as domains for addition to the ZFP of choice. In one preferred embodiment, the regulatory domain is a DNA methyl transferase that acts as a transcriptional repressor (see, e.g., Van den Wyngaert et al., *FEBS Lett.* 426:283-289 (1998); Flynn et al., *J. Mol. Biol.* 279:101-116 (1998); Okano et al., *Nucleic Acids Res.* 26:2536-2540 (1998); and Zardo and Caiafa, *J. Biol. Chem.* 273:16517-16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived froin microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin and Scotto, *Mol. Cell. Biol.* 18:4377-4384 (1998); Wolffe, *Science* 272:371-372 (1996); Taunton et al., *Science* 272:408-411 (1996); and Hassig et al., *Proc. Natl. Acad. Sci. USA* 95:3519-3524 (1998)). In another embodiment, histone deacetylase is used as a transcriptional repressor (see, e.g., Jin and Scotto, *Mol. Cell. Biol.* 18:4377-4384 (1998); Syntichaki and Thireos, *J. Biol. Chem.* 273:24414-24419 (1998); Sakaguchi et al., *Genes Dev.* 12:2831-2841 (1998); and Martinez et al, *J. Biol. Chem.* 273:23781-23785 (1998)).

Linker domains between polypeptide domains, e.g., between two ZFPs or between a ZFP and a regulatory domain, can be included. Such linkers are typically polypeptide sequences, such as poly gly sequences of between about 5 and 200 amino acids (SEQ ID NO: 92). Linkers can be flexible or rigid amino acid subsequences which are synthesized as part of a recombinant fusion protein. See, e.g., U.S. Pat. No. 6,534,261; Liu et al., *Proc. Nat. Acad. Sci. USA*, 95:5525-5530 (1997); Pomerantz et al., *Proc. Nat. Acad. Sci. USA* 92:9752-9756 (1995); Kim et al., *Proc. Nat. Acad. Sci. USA* 93:1156-1160 (1996); herein incorporated by reference in their entireties. Alternatively, flexible linkers can be rationally designed using computer program capable of modeling both DNA-binding sites and the peptides themselves (Desjarlais and Berg, *Proc. Nat. Acad. Sci. USA* 90:2256-2260 (1993), Desjarlais and Berg, *Proc. Nat. Acad. Sci. USA* 91:11099-11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to regulatory domains, non-covalent methods can be used to produce molecules with ZFPs associated with regulatory domains.

Cleavage Domains

As noted above, the DNA-binding domain may also be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., Si Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in certain embodiments, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Patent Publication No. 2008/0131962, the disclosure of which is incorporated by reference in its entirety for all purposes. See, also, Szczepek et al. (2007) Nat Biotechnol 25:786-793. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. provisional application 61/337,769 filed Feb. 8, 2010). In other embodiments, the engineered cleavage half domain comprises the "Sharkey" and/or "Sharkey'" mutations (see Guo et al, (2010) J. Mol. Biol. doi:10.1016/j.jmb.2010.04.060).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Another preferred Type IIS restriction enzyme is BfiI (see Zaremba et al, (2004) J. Mol. Biol. 336(1):81-92). The cleavage domain of this enzyme may be separated from its DNA binding domain and operably linked to a zinc finger DNA binding domain to create a ZFN.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains) and regulatory or cleavage domains (or cleavage half-domains), and polynucleotides encoding such fusion proteins, are described in co-owned U.S. Pat. Nos. 6,453,242 and 6,534,261 and U.S. Patent Application Publications 2007/0134796 and 2005/0064474; herein incorporated by reference in their entireties.

In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

As noted above, in certain embodiments, the fusion protein comprises a zinc finger protein that binds to a target site in a gene involved in fatty acid biosynthesis and at least one transcriptional regulatory domain, for example an activation or repression domain.

In other embodiments of the methods described herein, a zinc finger nuclease comprises a fusion protein comprising a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the zinc finger nucleases (e.g., ZFP-Fok I fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-Fok I fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments, the disclosed fusion proteins the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

In one embodiment, the disclosure provides a ZFN comprising a zinc finger protein having the recognition helix amino acid sequences shown in Table 1 or Table 10. In another embodiment, provided herein is a ZFN expression vector comprising a nucleotide sequence encoding a ZFP having the recognition helices shown in Table 1 or Table 10.

Regulation of Gene Expression

A variety of assays can be used to determine whether a ZFP modulates gene expression. The activity of a particular ZFP can be assessed using a variety of in vitro and in vivo assays, by measuring, e.g., protein or mRNA levels, product levels, enzyme activity; transcriptional activation or repression of a reporter gene, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, phenotypic assays, and the like.

ZFPs are typically first tested for activity in vitro using ELISA assays and then using kidney cells. The ZFP is often first tested using a transient expression system with a reporter gene, and then regulation of the target endogenous gene is tested in cells and in whole plants, both in vivo and ex vivo. The ZFP can be recombinantly expressed in a cell, recombinantly expressed in cells transplanted into a plant, or recombinantly expressed in a transgenic plant, as well as administered as a protein to plant or cell using delivery vehicles described below. The cells can be immobilized, be in solution, be injected into a plant, or be naturally occurring in a transgenic or non-transgenic plant.

Modulation of gene expression is tested using one of the in vitro or in vivo assays described herein. Samples or assays are treated with a ZFP and compared to control samples without the test compound, to examine the extent of modulation. For regulation of endogenous gene expression, the ZFP typically has a $K_d$ of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or plants, one can also measure a variety of effects such as plant growth, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with an empty vector or an unrelated ZFP that is targeted to another gene.

In another embodiment, ZFP regulation of endogenous gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the ZFP of choice, the amount of reporter gene transcription, translation, or activity is measured according to standard techniques known to those of skill in the art.

Transgenic and non-transgenic plants are also used as a preferred embodiment for examining regulation of endogenous gene expression in vivo. Transgenic plants can stably express the ZFP of choice. Alternatively, plants that transiently express the ZFP of choice, or to which the ZFP has been administered in a delivery vehicle, can be used. Regulation of endogenous gene expression is tested using any one of the assays described herein.

Methods for Targeted Cleavage

The disclosed methods and compositions can be used to cleave DNA at a region of interest in cellular chromatin (e.g., at a desired or predetermined site in a genome, for example, within or adjacent to a gene involved in fatty acid biosynthesis). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity, of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near where cleavage is desired. The fusion protein, or a polynucleotide encoding same, is introduced into a plant cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (see, for example, Smith et al. (2000) Nucleic Acids Res. 28:3361-3369; Bibikova et al. (2001) Mol. Cell. Biol. 21:289-297) and the length of the ZC linker in each fusion protein. See, also, U.S. Patent Publication 20050064474A1 and International Patent Publications WO05/084190, WO05/014791 and WO03/080809.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian and plant genomes, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins is bound, its cleavage half-domain forms a dimer with the dominant negative mutant half-domain, and undesirable, non-specific cleavage does not occur.

Expression Vectors

A nucleic acid encoding one or more proteins (e.g., ZFPs) as described herein can be cloned into a vector for transformation into prokaryotic or eukaryotic cells for replication and/or expression. Vectors can be prokaryotic vectors, e.g., plasmids, or shuttle vectors, insect vectors, viral vectors, or eukaryotic vectors. A nucleic acid encoding a ZFP can also be cloned into an expression vector, for administration to a plant cell.

To express the ZFPs, sequences encoding the ZFPs are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* Stockton Press, New York (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian, plant, yeast, and insect cells are well known by those of skill in the art and are also commercially available.

The promoter used to direct expression of a ZFP-encoding nucleic acid depends on the particular application. For example, a strong constitutive promoter suited to the host cell is typically used for expression and purification of ZFPs.

In contrast, when a ZFP is administered in vivo for regulation of a plant gene (see, "Nucleic Acid Delivery to Plant Cells" section below), either a constitutive or an inducible promoter is used, depending on the particular use of the ZFP. Non-limiting examples of plant promoters include promoter sequences derived from *A. thaliana* ubiquitin-3 (ubi-3) (Callis, et al., 1990, *J. Biol. Chem.* 265-12486-12493); *A. tumefaciens* mannopine synthase (Δmas) (Petolino et al., U.S. Pat. No. 6,730,824); and/or Cassaya Vein Mosaic Virus (CsVMV) (Verdaguer et al., (1996), *Plant Molecular Biology* 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

The particular expression vector used to transport the genetic information into the cell is selected with regard to the intended use of the ZFP, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, plant, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss and Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach and Weissbach *Methods for Plant Molecular Biology* (1988, Academic Press, N.Y.) Section VIII, pp. 421-463; and Grierson and Corey, *Plant Molecular Biology* (1988, 2d Ed.), Blackie, London, Ch: 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al., (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al., (1984) *Science* 233:496-498, and Fraley et al., (1983) *Proc. Nat'l. Acad. Sci. USA* 80:4803.

In addition, gene transfer may be achieved using non-Agrobacterium bacteria or viruses such as *Rhizobium* sp. NGR234, *Sinorhizoboium meliloti, Mesorhizobium loti*, potato virus X, cauliflower mosaic virus and cassaya vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) Science 227:1229-1231). Generally, the *Agrobacterium* transformation system is used to engineer dicotyledonous plants (Bevan et al., (1982) *Ann. Rev. Genet.* 16:357-384; Rogers et al., (1986) *Methods Enzymol.* 118: 627-641). The *Agrobacterium* transformation system may also be used to transform, as well as transfer, DNA to monocotyledonous plants and plant cells. See U.S. Pat. No. 5,591, 616; Hernalsteen et al., (1984) *EMBO J.* 3:3039-3041; Hooykass-Van Slogteren et al., (1984) *Nature* 311:763-764; Grimsley et al. (1987) *Nature* 325:1677-179; Boulton et al., (1989) *Plant Mol. Biol.* 12:31-40.; and Gould et al., (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618) or nanoparticles.

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed, soybean) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct, and including seeds with desired modified oil profiles. The present disclosure further encompasses the progeny, clones, cell lines or cells of the transgenic plants described above wherein said progeny, clone, cell line or cell has the transgene or gene construct.

Administration of effective amounts is by any of the routes normally used for introducing ZFPs into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of compositions that are available.

Applications

As noted above, targeted modulation of genes involved in fatty acid synthesis can be used to quickly and efficiently generate plant oils of the desired fatty acid profile.

Altering the fatty acid compositions of plant oils from oil-producing plants such as, for example canola, has profound implications for food production and, consequently, on dietary health. For example, canola-quality oilseed *Brassica* varieties with reduced levels of saturated fatty acids in the seed oil can be used to produce food products which promote cardiovascular health. The methods and compositions described herein can be used to generate oil-producing plants with low palmitic and/or stearic acid content, which reduce the levels of saturated fatty acids in the plant oil. Similarly, generating oil-producing plants with increased levels of oleic acid content will also reduce the amount of saturated fatty acids in the plant oil.

Furthermore, the methods and compositions described herein can be used to increase palmitic acid content, for example in oils produced from such plants. Oils high in palmitic acid content are particularly useful in the formulation of margarines.

In addition, targeted alteration of fatty acid profiles as described herein can be used to generate plants (and plant oils) which are low in linolenic acid. Low linolenic acid oils show increased stability; foods made using these oils do not go off in terms of flavor or odor as quickly as foods made from plant materials with high linolenic acid concentrations.

EXAMPLES

Below are examples of specific embodiments for carrying out the present disclosure. The examples are offered for illustrative purposes only, and are not intended to limit the scope of the present disclosure in any way.

Efforts have been made to ensure accuracy with respect to numbers used (e.g., amounts, temperatures, etc.), but some experimental error and deviation should, of course, be allowed for.

Example 1

Target Sequence Identification in *Brassica napus* L 1.1 Target Sequence Identification In this example, endogenous DNA sequences encoding β-ketoacyl-ACP synthetase II (KAS II) enzyme native to *Brassica napus* L (canola) were identified. These genes were selected as exemplary targets to demonstrate transcriptional regulation via engineered zinc-finger protein transcription factors (ZFP TF) resulting in desired modification of fatty acid biosynthesis and concomitant altered seed oil profiles. The enzyme β-ketoacyl-ACP synthetase II catalyzes the conversion of 16:0-ACP to 18:0-ACP and the subsequent formation of oleic acid (Ohlrogge and Browse, 1995, *The Plant Cell*, 7: 957-970). A reported *Arabidopsis thaliana* fab1 mutant of the β-ketoacyl-ACP synthetase II gene resulted in a 65% reduction in enzyme activity and concomitant increases of stearic acid content by 7% and 3% in leaves and roots, respectively (Wu et al., 1994, *Plant Physiology*, 106: 143-150). A stably expressing transformed soybean β-ketoacyl-ACP synthetase II transgene in canola decreased seed palmitic acid content by 0.8% and introduction of the same gene in tobacco decreased the palmitic acid content by 2% (Japanese Patent Publication # 501446/1995).

cDNA sequences of β-ketoacyl-ACP synthetase II have been reported from multiple plant species including *Arabidopsis thaliana* (GenBank: AF318307) and *Brassica napus* (GenBank: AF244520). The alignment of *A. thaliana* and *B. napus* cDNA sequences (GenBank: AF318307 and AF244520, respectively) showed that the AF244520 sequence was incomplete (FIG. 7). This truncated *B. napus* DNA sequence was missing several hundred base pairs at the 5' end. In addition, since *B. napus* is an amphidiploid species resulting from the combination of the chromosome sets of *B. rapa* (2n=20, AA) and *B. oleracea* (2n=18, CC) (Morinaga, 1934, *Cytologia*, 6:62-67; U.N., 1935, *Japanese J. Bot.*, 7:389-452), it is predicted that there would be more than one β-ketoacyl-ACP synthetase II gene in this species. The additional 5' UTR sequences present in the cDNA sequences were identified and obtained. These 5' β-ketoacyl-ACP synthetase II gene sequences served as targets for transcriptional up-regulation via ZFP-TFs in the present examples.

1.2 Total RNA Isolation

Total RNA was isolated from immature seed of *Brassica napus* (canola) genotype Nex710 (Crop Certificate 99-7049208-501) 15 days after flowering (DAF) using Qiagen's RNEASY®PLANT MINI KIT (Qiagen, Valencia, Calif.). Total mRNA was treated with RNase-free DNase as per manufacturer's recommendation to remove any contaminating DNA that might amplify during quantitative RT-PCR.

1.3 5' RACE and Sequence Analysis

Rapid amplification of cDNA ends (RACE) specific to the 5' end of the *B. napus* β-ketoacyl-ACP synthetase II cDNA (GenBank AF244520) was performed using FIRSTCHOICE® RLM-RACE kit from Ambion (Ambion, Austin, Tex.) per manufacturer's recommendations. To obtain the 5' cDNA sequence, a synthetic RNA adapter was annealed to the 5' uncapped mRNA region. A primer supplied with the kit (5'-CGCGGATCCGAACACTGCGTTTGCTG-GCTTTGATGAAA-3') (SEQ ID NO:1) and a second primer (5'-CTCGAGCTGCTACTGCTAGTTCCGGTG-GAGGAGCC-3') (SEQ ID NO:2) which was designed to bind within the partial *B. napus* cDNA sequence (GenBank AF244520) were used to amplify a fragment to determine the unknown upstream sequence. The 5' RACE amplification identified about 500 base pairs of new *B. napus* sequences. Contigs of four clearly different 5' cDNA sequences of β-ketoacyl-ACP synthetase II genes (SEQ ID NO: 3, SEQ ID NO: 4, SEQ ID NO: 46, and SEQ ID NO: 30) were identified when the amplified sequences were aligned (FIG. 8). These 5' sequences showed high levels of homology to *B. rapa* (GenBank: AC189461) and *B. oleracea* (GenBank: BH723504) sequences from the same region.

ZFP TF binding sequences were identified in the 5' cDNA sequences of β-ketoacyl-ACP synthetase II genes. The sequences from the upstream region of β-ketoacyl-ACP synthetase II genes (Table 2) served as targets for ZFP TF binding (Table 1). Plasmid constructs: pDAB4695, pDAB4696, pDAB4697, and pDAB4698 containing the engineered ZFP TF designs were used to stably transform *B. napus* as described in the next sections. It was hypothesized that engineered ZFP TFs upon expression in plant cells would bind to the endogenous β-ketoacyl-ACP synthetase II targets resulting in modified mRNA expression of the target.

Example 2

Design of ZFP DNA Binding Domains Specific to β-ketoacyl-ACP Synthetase II Gene

Figure 2:
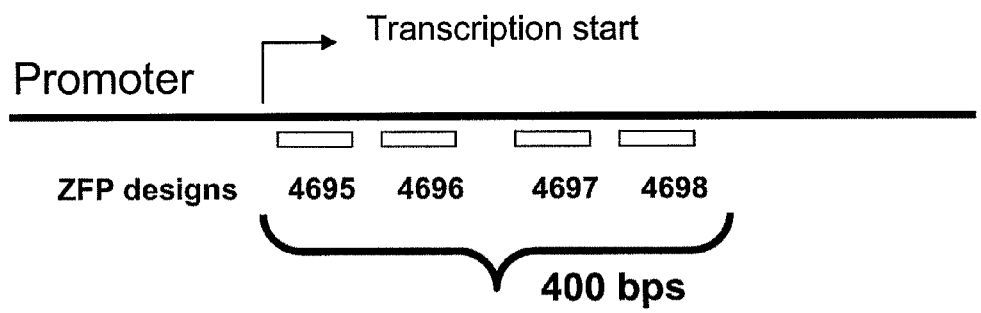
FIG. 2 is a schematic depicting the target site locations within the KASII gene for various exemplary KASII-targeted ZFP TFs. Numbers indicate the target sites for the ZFPs contained within the constructs shown in Table III. ZFP designs are shown in Tables I and II.

Zinc finger proteins were designed against various targets sites in the *B. napus* β-ketoacyl-ACP synthetase II gene promoter region and 5' untranslated and translated region. See, FIG. 2. The recognition helices for representative ZFP designs are shown below in Table 1. Target sites of the zinc finger designs are shown below in Table 2.

TABLE 1

| | β-ketoacyl-ACP synthetase II Zinc finger Designs | | | | | |
|---|---|---|---|---|---|---|
| ZFP | F1 | F2 | F3 | F4 | F5 | F6 |
| 14025 | RSDNLSV (SEQ ID NO: 5) | QKINLQV (SEQ ID NO: 6) | RSDTLSE (SEQ ID NO: 7) | TRSSRIN (SEQ ID NO: 8) | RSDALAR (SEQ ID NO: 9) | N/A |

TABLE 1-continued

β-ketoacyl-ACP synthetase II Zinc finger Designs

| ZFP | F1 | F2 | F3 | F4 | F5 | F6 |
|---|---|---|---|---|---|---|
| 14033 | RSDHLSA (SEQ ID NO: 10) | TSSSRIN (SEQ ID NO: 11) | RSDNLAR (SEQ ID NO: 12) | DRSHLAR (SEQ ID NO: 13) | RSDNLSE (SEQ ID NO: 14) | RNAHRTT (SEQ ID NO: 15) |
| 14035 | QSGNLAR (SEQ ID NO: 16) | RSDHLSE (SEQ ID NO: 17) | QKANRTK (SEQ ID NO: 18) | RSDDLTR (SEQ ID NO: 19) | TSANLSR (SEQ ID NO: 20) | N/A |
| 14047 | RSDDLSK (SEQ ID NO: 21) | RSANLTR (SEQ ID NO: 22) | RSDDLTR (SEQ ID NO: 19) | RSDHLSE (SEQ ID NO: 17) | DKSNRKK (SEQ ID NO: 23) | N/A |

TABLE 2

Target Sites of β-ketoacyl-ACP synthetase II Zinc Fingers

| ZFP | Target Site (5' to 3') | ZFP target/binding site present in SEQ ID Nos. |
|---|---|---|
| 14025 | cGTGGAGACGtCAAAAGa (SEQ ID NO: 24) | 3, 4, 46 and 30 |
| 14033 | aAGGAAGGGCGAGAAAAGGg (SEQ ID NO: 25) | 3 and 4 |
| 14035 | aGATGCGTAACAGGAAg (SEQ ID NO: 26) | 3, 4, 46 and 30 |
| 14047 | cTACCGGGCGGAGTCGt (SEQ ID NO: 27) | 3, 4 and 30 |

The β-ketoacyl-ACP synthetase II designs were incorporated into zinc finger expression vectors encoding a protein having at least one finger with a CCHC structure. See, U.S. Patent Publication No. 2008/0182332. In particular, the last finger in each protein had a CCHC structure (architecture).

The zinc finger-encoding sequences were then fused to sequences encoding a VP16 activation domain and an opaque-2 nuclear localization signal. Expression of the fusion proteins was driven by a relatively strong constitutive promoter such as a promoter derived from the *Arabidopsis thaliana* Ubiquitin 10 (AtUbi10) promoter. Exemplary vectors are shown in Table 3 below.

Example 3

ZFP TF-Mediated Up-Regulation of the Native β-Ketoacyl-ACP Synthetase II Gene(s) in *B. napus*

In order to assess the functionality of designed zinc-finger proteins in plant cells, methods for the expression of such proteins in living plant cells were utilized. DNA encoding zinc-finger proteins can be delivered into plant cells under conditions where the DNA is not incorporated into the plant cell genome. Thus, the DNA molecule is transiently maintained in plant cells and acts as a template for gene expression. Alternatively, DNA encoding zinc-finger proteins can be delivered into plant cells under conditions that allow the DNA to be incorporated into the plant cell genome, resulting in transgenesis of the zinc-finger protein encoding genes such that the DNA molecule is stably maintained in the plant cells and acts as a template for gene expression. One skilled in the art may utilize either transient or transgenic expression of zinc-finger proteins encoding DNAs in order to assess the functionality of these proteins in living plant cells.

3.1 Construct Design

The binary plasmids designed and constructed for this project are listed in Table 3.

TABLE 3

Construct description for ZFP TFs targeted to *B. napus* KAS II

| S.N. | ZFP | Construct No. | Gene Cassette |
|---|---|---|---|
| 1 | 14025 | pDAB4695 | Atubi10/ZFP1-Vp16/AtuORF23/CsVMV/pat/AtuORF1 |
| 2 | 14033 | pDAB4696 | Atubi10/ZFP2-Vp16/AtuORF23/CsVMV/pat/AtuORF1 |
| 3 | 14035 | pDAB4697 | Atubi10/ZFP3-Vp16/AtuORF23/CsVMV/pat/AtuORF1 |
| 4 | 14047 | pDAB4698 | Atubi10/ZFP4-Vp16/AtuORF23/CsVMV/pat/AtuORF1 |

AtUbi10 = *Arabidopsis thaliana* Ubiquitin 10 promoter,
CsVMV = Cassava Vein Mosaic Virus promoter,
ZFP = zinc finger protein gene,
pat = phosphinothricin acyl transferase gene,
AtuORF1 = *Agrobacterium tumefaciens* 3' UTR 1 and
AtuORF23 = *Agrobacterium tumefaciens* 3' UTR 23.

pDAB4695 is a binary plasmid which contains the 14025 v3/VP 16 and pat gene expression cassettes. This construct includes the following gene elements; RB7 MAR v3 (Matrix Attachment Region (Thompson et al., 1997, WO9727207))::AtUbi10 Promoter v2 (*Arabidopsis thaliana* Ubiquitin-10 Promoter (Callis, et al., 1990, *J. Biol. Chem.* 265-12486-12493))::14025 v3 Zinc Finger/VP16 Fusion::Atu ORF23 3'UTR v1 (*Agrobacterium tumefaciens* Open Reading Frame 23, 3'UnTranslated Region (Gelvin et al., 1987, EP222493)) CsVMV Promoter v2 (Cassaya Vein Mosaic Virus Promoter (Verdaguer et al., 1996, *Plant Molecular Biology* 31: 1129-1139))::pat v5 (Phosphinothricin Acetyl Transferase (Wohlleben et al., 1988, *Gene* 70:25-37))::AtuORF 1 3'UTR v4 (*Agrobacterium tumefaciens* Open Reading Frame 1, 3'UnTranslated Region (Huang et al., *J. Bacteriol.* 172:1814-1822)). The binary was constructed by cloning a DNA fragment containing the 14025 v3 Zinc Finger/VP16 fusion into pDAB3916 via NcoI-SacI restriction sites. The resulting construct which was labeled as pDAB8221 contained the AtUbi10 Promoter v2::14025 v3 Zinc Finger/VP16 Fusion::Atu ORF23 3'UTR v1 gene expression cassette. pDAB8221 was cloned into the pDAB7309 binary via an L-R Gateway® Reaction (Invitrogen, Carlsbad, Calif.). This reaction produced pDAB4695 and was confirmed via restriction enzyme digestions and sequencing reactions.

pDAB4696 is a binary plasmid which contains the 14033 v3/VP 16 and pat gene expression cassettes. This construct includes the following gene elements; RB7 MAR v3:: AtUbi10 Promoter v2::14033 v3 Zinc Finger/VP16 Fusion:: Atu ORF23 3'UTR v1 CsVMV Promoter v2::pat v5::At-uORF 1 3'UTR v4. The binary was constructed by cloning a DNA fragment containing the 14033 v3 Zinc Finger/VP16 fusion into pDAB3916 via NcoI-SacI restriction sites. The resulting construct which was labeled as pDAB8222 contained the AtUbi10 Promoter v2::14033 v3 Zinc Finger/VP16 Fusion::Atu ORF23 3'UTR v1 gene expression cassette. pDAB8222 was cloned into the pDAB7309 binary via an L-R Gateway® Reaction (Invitrogen, Carlsbad, Calif.). This reaction produced pDAB4696 and was confirmed via restriction enzyme digestions and sequencing reactions.

pDAB4697 is a binary plasmid which contains the 14035 v3/VP 16 and pat gene expression cassettes. This construct includes the following gene elements; RB7 MAR v3:: AtUbi10 Promoter v2::14035 v3 Zinc Finger/VP16 Fusion:: Atu ORF23 3'UTR v1::CsVMV Promoter v2::pat v5::At-uORF 1 3'UTR v4. The binary was constructed by cloning a DNA fragment containing the 14035 v3 Zinc Finger/VP16 fusion into pDAB3916 via NcoI-SacI restriction sites. The resulting construct which was labeled as pDAB8223 contained the AtUbi10 Promoter v2::14035 v3 Zinc Finger/VP16 Fusion::Atu ORF23 3'UTR v1 gene expression cassette. pDAB8223 was cloned into the pDAB7309 binary via an L-R Gateway® Reaction (Invitrogen, Carlsbad, Calif.). This reaction produced pDAB4697 and was confirmed via restriction enzyme digestions and sequencing reactions.

pDAB4698 is a binary plasmid which contains the 14047 v3/VP 16 and pat gene expression cassettes. This construct includes the following gene elements; RB7 MAR v3:: AtUbi10 Promoter v2::14047 v3 Zinc Finger/VP 16 Fusion:: Atu ORF23 3'UTR v1 CsVMV Promoter v2::pat v5::At-uORF 1 3'UTR v4. The binary was constructed by cloning a DNA fragment containing the 14047 v3 Zinc Finger/VP16 fusion into pDAB3916 via NcoI-SacI restriction sites. The resulting construct which was labeled as pDAB8224 contained the AtUbi10 Promoter v2::14047 v3 Zinc Finger/VP16 Fusion::Atu ORF23 3'UTR v1 gene expression cassette. pDAB8224 was cloned into the pDAB7309 binary via an L-R Gateway® Reaction (Invitrogen, Carlsbad, Calif.). This reaction produced pDAB4698 and was confirmed via restriction enzyme digestions and sequencing reactions.

3.2 *Agrobacterium* Transformation

*Agrobacterium* cells were prepared for electroporation using the protocol described in Weigel D., Glazebrook J. *Arabidopsis: A Laboratory Manual*. Cold Spring Harbor Laboratory Press, 2002: pg 123-124. Minor modifications were made to the protocol that allowed for optimal growth of *Agrobacterium* (i.e. YEP media was substituted for LB). Independently, 1.5-3 μg of plasmid DNA for each construct was added to 50 μl of C58::Z707s *Agrobacterium tumefaciens* cells and gently mixed. The mixture was transferred to cold 0.2 cm GENE PULSER® cuvettes (BioRad Hercules, Calif.) and placed on ice. The cuvettes were then placed in a cold GENE PULSER® rack (BioRad, Hercules, Calif.) and electroporated at the following conditions: capacitance output 25 μFarad, capacitance extender 960 μFarad, resistance 200 ohms, and voltage 2.5 kVolts. Immediately after electroporation, 950 μl of SOC medium (Invitrogen, Carlsbad, Calif.) was added and the mixture was transferred to a Falcon 2059 tube (Becton Dickinson and Co., Franklin Lakes, N.J.) or equivalent. The transformed cells were then incubated at 28° C. for 1 hour. After incubation, 50 μl, 100 μl, and 200 μl of cells were plated on separate YEP medium plates (10 gm yeast extract, 10 gm peptone, 5 gm NaCl, 10 gm sucrose, and 15 gm agar in 1 Liter of water) containing antibiotics as appropriate. The plates were grown inverted at 28° C. for approximately 36-48 hours. Single colonies were picked and propagated in 50 ml of liquid YEP (10 gm yeast extract, 10 gm peptone, 5 gm NaCl, and 10 gm sucrose in 1 Liter of water), containing antibiotics as appropriate, at 28° C. for approximately 36 hours.

The *Agrobacterium tumefaciens* strain was confirmed via a ketolactose test. Putatively transformed colonies were streaked out on lactose agar and incubated at 28° C. for 48 hours. The plates were then flooded with Benedict's Solution. The plates were monitored; streaked isolates which turned the Benedict's Solution from blue to yellow were confirmed as *Agrobacterium* (Bouzar, H., Jones, J., Bishop, A. "Simple Cultural Tests for Identification of *Agrobacterium* Biovars." *Methods in Molecular Biology*, Volume 44. Humana Press, 1995: 9-13).

After completing a QIAGEN® low copy mini-prep protocol (Qiagen, Valencia, Calif.), purified plasmid DNA was prepared from the bacterial cultures. DNA integrity was evaluated by restriction digest. Clones with the expected banding patterns were identified and glycerol stocks were prepared by adding 500 μl of bacterial culture to 500 μl of sterile glycerol (Sigma Chemical Co., St. Louis, Mo.) and inverting to mix. Glycerol stocks were frozen on dry ice and stored at −80° C.

3.3 Transformation of *B. napus* with ZFP TFs

Preparation of Hypocotyl Segments: seeds of *B. napus* genotype, Nex 710, were surface-sterilized with 10% commercial bleach for 10 minutes and rinsed 3 times with sterile distilled water. The seeds were dried via a sterile paper towel then placed in a Phyta-tray containing 'germination medium' consisting of one half concentration of MS basal medium (Murashige and Skoog, *Physiol Plant* 15(3): 473-497, 1962), 20 g/L sucrose, and 8 g/L TC Agar (PhytoTechnology Laboratories, Shawnee Mission, Kans.) and maintained under growth regime set at 23° C., and a photoperiod of 16 hrs light/8 hrs dark.

On day 5, seedlings were checked for sterility and the Phyta-tray was placed inside an EDGEGARD® laminar flow hood (The Baker Company, Sanford, Me.) to maintain sterility. Using sterile forceps and dissecting scissors, plants were removed from the Phyta-tray and the aerial (meristem and cotyledon) region and roots were detached and discarded. Hypotcotyls were placed into a 100×25 mm petri dish containing sterile distilled water which is required to prevent drying. Hypocotyls were placed onto the lid of a 100×25 mm petri dish and cut transversely into 3 mm segments using a #10 scalpel. Hypocotyl segments were placed on 'callus induction medium' consisting of MS medium containing 30 g/L sucrose, 1 mg/L kinetin and 1 mg/L 2,4-D solidified with 7 g/L TC Agar including a sterile filter paper. The plates were placed into a clear STERILITE® tub and maintained under the same growth regime for 3 days, as a pre-treatment.

On day 8, the segments were then transferred into a 100×25 sterile petri plate containing 20 mL of 'liquid culture medium' consisting of Linsmaier and Skoog basal medium (1965) containing 30 g/L glucose, ½ strength Gamborg vitamins (1968), 215.2 mg/l kinetin and 221.04 mg/l 2,4-D for a 1 hour pretreatment. The 'liquid culture medium' was removed from the hypocotyl segments and 40 mL of *Agrobacterium* suspension (containing either pDAB4695, pDAB4696, pDAB4697 or pDAB4698 in Z707s) at a 50 Klett was vortexed briefly and poured into the 100×25 mm petri dish containing hypocotyl segments for a 30 minute treatment. After 30 minutes, all of the *Agrobacterium* suspension was removed using a double stacked pipette. The treated hypocotyls were placed back onto the 'callus induction medium' plus filter papers, returned to the STERILITE® tub, covered with a dark lid and returned to the culture room under the same growth regime as above, for a 3 day co-cultivation period. After 3 days, the hypocotyls were placed directly onto 'callus induction medium' containing 1 mg/L HERBIACE®, placed back into the tub with a clear lid and returned to the culture room, maintaining the same growth regime as above. After 1 week, the hypocotyls were transferred directly to 'callus induction medium' with selection at 3 mg/L HERBIACE® for 2 weeks for further callus development and transferred to 'callus induction medium' with selection at 5 mg/L HERBIACE for 2-8 weeks for additional callus development. Once a sufficient amount of callus was available it was submitted for molecular analysis.

Regeneration of Plants from Aged Canola Callus: Canola callus tissue was placed onto 'shoot regeneration medium' consisting of MS medium containing 30 g/L sucrose, 3 mg/L benzyaminopurine, 0.5 g/L MES [2-(N-morpholion) ethane sulfonic acid], 5 mg/L silver nitrate, 1 mg/L zeatin, 250 mg/L carbenicillin, 300 mg/L timentin and 7 g/L TC Agar with selection at 5 mg/L HERBIACE®, plates were wrapped with 3M tape and place under growth regime set at 23° C., and a photoperiod of 16 hrs light/8 hrs dark. The tissues were then moved to 'shoot elongation medium' consisting of MS medium containing 0.5 g/L MES, 300 mg/L timentin, 20 g/L sucrose and 7 g/L TC Agar with selection at 5 mg/L HERBIACE®. Plantlets were transferred to 'rooting medium' consisting of ½ MS medium containing 10 g/L sucrose, 0.5 mg/L indolebutyric acid, 300 mg/Utimentin and 8 g/L TC Agar with selection at 5 mg/L HERBIACE®.

Once roots established on the plantlet in vitro, they were transplanted to 5¼" pots containing Metro Mix 360. The plants were covered with a clear solo cup and placed into a conviron for acclimation. After 48-72 hours, cups were removed to allow air circulation. After a total of seven days, the pots were shifted from the conviron to a greenhouse bay for further development. Plants were grown under a 16:8-hour photoperiod, with daytime and nighttime temperature between 22-24° C. When the primary flowering stem began to elongate and form flower buds, the entire plant was covered with a selfing bag to prevent outcrossing. Seeds derived from self-pollinations were harvested about four months after transplanting.

Preparation of *Agrobacterium*: The *Agrobacterium* from a glycerol stock was streaked, four days prior to treatment, onto 'semi solid bacterial growth medium' consisting of 10 g/L Peptone, 10 g/L Yeast Extract, 5 g/L NaCl, 10 g/L Sucrose plus 100 mg/L spectinomycin and 250 mg/L streptomycin and solidified with 15 g/L Bacto Agar and grown for two days in an incubator (Fisher Scientific Isotemp Incubator) at 28° C. After 2 days, a small loop of *Agrobacterium* was placed into a 500 mL sterile disposable baffled flask containing 150 mL 'liquid bacterial growth medium' (same as, above minus solidifying agent), 250 mg/L of streptomycin and 100 mg/L of spectinomycin, grown for 16 hours overnight at 28° C. in the dark on an enclosed shaker (New Brunswick Scientific Innova 4330 refrigerated incubator shaker) at 200 rpm. After 16 hours the *Agrobacterium* culture was removed from the shaker and aliquotted into 50 mL centrifuge tubes (one containing 35 mL for preparation and two containing 50 mL for revalidation). The centrifuge tubes are placed into a centrifuge (Beckman Model J2-21 centrifuge) and centrifuged at 6,000 rpm for 15 minutes and subsequently re-suspended in the 'liquid culture medium' to a final density of Klett 50 with a red filter.

Example 4

Analysis of Transformed Callus Samples

Putatively transformed *B. napus* callus samples were analyzed for alterations in mRNA expressions for β-ketoacyl-ACP synthetase II endogenous gene, tubulin endogenous gene and ZFP TF transgene. The tubulin mRNA levels were used as an internal control to normalize the expression of ZFP TF and β-ketoacyl-ACP synthetase II mRNAs. The ZFP TF mRNA expression data was used to confirm the presence of at least one functional ZFP TF transgene in transformed calli.

4.1 Callus Sample Preparation

Approximately 40-50 eight-week-old callus samples of *B. napus* were obtained after the transformation of Nex710 hypocotyl tissue. They were individually transformed with the ZFP TF constructs, pDAB4695, pDAB4696, pDAB4697, and pDAB4698 as described above in Example 3.3. Control samples were obtained by transformation of a control binary construct containing a pat gene expression cassette (AtUbi10 Promoter v2::pat v3::Atu ORF1 3'UTR v3). All samples were grown in HERBIACE-supplemented cell culture medium until their harvest.

Total RNA was prepared from the fresh callus tissue using QIAGEN RNEASY 96 Kit (Qiagen, Valencia, Calif.). The RNA was treated with RNase-free DNase according to the kit's instructions to remove any genomic DNA contaminants. First strand synthesis was set up according to the Superscript® III Reverse Transcriptase Enzyme (Invitrogen, Carlsbad, Calif.) manufacturer's instructions and primed using random hexamers. The synthesized cDNA strands were diluted in water at ratios of 1:10 and 1:50 (this provides sufficient template to PCR amplify multiple targets). Each aliquot was saved at −20° C. indefinitely.

4.2 β-Ketoacyl-ACP Synthetase II mRNA Expression Analysis qRT-PCR reaction mixes were set up for amplification of the β-ketoacyl-ACP synthetase II cDNA as follows: 7.5 µL of 2×LC480 Probes Master Buffer (Roche Diagnostic, Indianapolis, Ind.), 0.3 µL gene specific forward primer (SEQ ID NO: 28: 5'-TTGACTCGAGCTGCTACTGC-3'; nucleotide positions 544-563 for SEQ ID NO: 3 in FIG. 8 alignment) from 10 µM stock, 0.3 µL gene specific reverse primer (SEQ ID NO: 29: 5'-TTTCCATATCCATCGCAACA-3'; nucleotide positions 588-607 for SEQ ID NO: 3 in FIG. 8 alignment) from 10 µM stock, 0.15 µL UPL probe #25 from LIGHTCYCLER® 480 Probes Master, (Roche Diagnostic, Indianapolis, Ind.), 1.5 µL of 10% (w/v) polyvinyl pyrrolidone-40 (PVP-40), and 3.9 µL water. The UPL probe (Roche Diagnostics, Indianapolis, USA) is a locked nucleic acid and therefore has a higher Tm than otherwise calculated. All components were put back in the freezer prior to handling standards and unknowns. A 384-well microplate was demarcated and labeled, 13.5 µL of master mix was added per well. A sealing foil was gently attached to the microplate. The plate was centrifuged for 1 minute at 3,000 rpm in a Qiagen microplate centrifuge. 1.5 pit of thawed, diluted synthesized cDNA strands were added. Additionally, 1.5 µL of plasmid DNA copy number standards were added to separate wells in a dilution series from lowest to highest concentrations, these standards were compared to the β-ketoacyl-ACP synthetase II cDNA (synthesized from total mRNA) to quantitate the copy number. β-ketoacyl-ACP synthetase II DNA copy number standard series were made by cloning the target amplicon into a pCR2.1 plasmid (Invitrogen, Carlsbad, Calif.) and making a dilution series for quantifying the copy number. A foil seal was firmly affixed to the plate and centrifuged as previously described. A PCR program was performed as follows: i. Activate 95° C. for 5 minutes; ii. Denature 95° C. for 10 sec @ 4.8° C./sec; iii. Anneal/Extend 60° C. for 25 sec @ 2.5° C./sec; iv. Acquire 72° C. for 1 sec @ 4.8° C./sec; Repeat step ii-iv, 40-50 more times; Cool to 38° C. for 5 sec. DNA was amplified in Real-time PCR instrumentation LC480 (Roche, Indianapolis, Ind.) or equivalent. The amplicon size was 64 base pairs. The forward and reverse primer sequences employed in this PCR assay matched perfectly with the corresponding sequences present in two of the β-ketoacyl-ACP synthetase II gene targets, SEQ ID NOs: 3 and 30 (FIG. 8). Therefore, this assay represented quantitative expression of two β-ketoacyl-ACP synthetase II gene targets.

4.3 Tubulin mRNA Expression Analysis

The tubulin gene, a native gene of *Brassica napus* (GenBank: AF258790 and GenBank: DU106489), was used as a reference standard to accurately normalize mRNA expression signal across genes in qRT-PCR assays. cDNA synthesized for β-ketoacyl-ACP synthetase II qRT-PCR assay (described in example 4.1) was also used in tubulin qRT-PCR assay as described below.

A qRT-PCR was set up with 0.3 μL of a gene specific forward primer (SEQ ID NO: 31: 5'-ACAGCGATTGCCTACAAGG-3') (10 μM stock) and 0.3 μL of a gene specific reverse primer (SEQ ID NO: 32: 5'-AGATGGTTAAGATCACCAAAGG-3') (10 μM stock), 1.5 μL of 10% (w/v) PVP-40, 3.9 μL water and 7.5 μL 2× LIGHTCYCLER® 480 SYBR Green I Master Mix (Roche, Indianapolis, Ind.) to detect and quantify DNA. A 384-well microplate was demarcated and labeled, 13.5 μL of master mix was added per well. A sealing foil was gently attached to the microplate. The plate was centrifuged for 1 minute at 3,000 rpm in a Qiagen microplate centrifuge. The sealing foil was removed and 1.5 μL of thawed, diluted synthesized cDNA strands were added. Additionally, 1.5 μL of plasmid DNA copy number standards were added to separate wells in a dilution series from lowest to highest concentrations, these standards were compared to the tubulin cDNA (synthesized from total mRNA) to quantitate the copy number. Tubulin DNA copy number standard series were made by cloning the target amplicon into a pCR2.1 plasmid (Invitrogen, Carlsbad, Calif.) and making a dilution series for quantifying the copy number. A foil seal was firmly affixed to the plate and centrifuged as previously described. A PCR program was run as follows: i. Activate 95° C. for 10 minutes; ii. Denature 95° C. for 10 sec @ 4.8° C./sec; iii. Anneal/Extend 55.5° C. for 20 sec @ 2.5° C./sec; iv. Acquire 72° C. for 20 sec @ 4.8° C./sec; steps ii-iv were repeated 39 more times; vi. Cool to 38° C. for 5 sec. DNA was amplified in Real-time PCR instrumentation LC480 or equivalent. A 307 base pair amplicon was amplified in this reaction. This reverse primer spans a 78 by intron based upon the GenBank sequence. Therefore, amplicons amplified from the genomic DNA would not be favored and genomic DNA contaminants would be of higher molecular weight and can easily be differentiated from that of cDNA by running amplicons on an agarose gel.

4.4 ZFP TF mRNA Expression Analysis

Expression of ZFP TF mRNA was quantitated from cDNA samples that were originally synthesized for β-ketoacyl-ACP synthetase II mRNA (described above in Example 4.1). A TaqMan PCR assay was designed from the ZFP cassette by anchoring primers to the opaque-2 NLS sequence at the 5' and VP16 sequence at the 3'. The PCR assay was set up using: 0.5 μL forward primer "OP2_NLS_F1" (SEQ ID NO: 33: 5'-AAGGAAGAGGAAGGAGTCTAACAG-3') from 10 μM stock, 0.5 μL reverse primer "VP16_R1" (SEQ ID 34: 5'-CTTCTGCTCTCCACCGTA-3') from 10 μM stock, 0.25 μL probe "VP16_MGB_185" (SEQ ID NO: 45: 5'-TTGATGGTGAAGATGT-3') from 5 μM stock, 1.5 μL of 10% (w/v) PVP-40, 1.5 μL 10× Hot Start PCR buffer, 1.0 μL 25 mM MgCl$_2$, 1.2 μL dNTP (2.5 mM each), 0.15 μL Hot Start Taq Polymerase (Qiagen, Valencia, Calif.), and 6.9 μL water, The cocktail was amplified using LIGHTCYCLER® 480 (Roche Diagnostics, USA). A 384-well microplate was demarcated and labeled, 13.5 μL of master mix was added per well. A sealing foil was gently attached to the microplate. The plate was centrifuged for 1 minute at 3,000 rpm in a Qiagen microplate centrifuge. The sealing foil was removed and 1.5 μL of thawed, diluted synthesized cDNA strands were added. A foil seal was firmly affixed to the plate and centrifuged as previously described. A PCR program was run as follows: i. Activate 95° C. for 15 minutes; ii. Denature 95° C. for 20 sec @ 4.8° C./sec; iii. Anneal/Extend 60° C. for 20 sec @ 2.5° C./sec; iv. Acquire 72° C. for 55 sec @ 4.8° C./sec; steps ii-iv were repeated 44 more times; vi. Cool to 38° C. for 5 sec. DNA was amplified in Real-time PCR instrumentation LC480 or equivalent. The amplicon size was 775 base pairs. ZFP TF cDNA/mRNA copy number was determined using a standard series in which the target amplicon was cloned into a plasmid and making a dilution series for PCR assays as described for β-ketoacyl-ACP synthetase II and tubulin examples above.

4.5 Expression Analysis of Callus Samples

ZFP TF mRNA expression was measured in 8-week-old transgenic callus samples putatively transformed with ZFP TFs and growing on HERBIACE® selection medium (see Example 3). ZFP TF quantitative mRNA expression, as measured with qRT-PCR assay, was detected in samples transformed with only ZFP TF containing constructs but not in samples containing the control construct. This data indicated that the assay was specific to ZFP TF expression and that control calli did contain ZFP TF transgene.

Ratios of β-ketoacyl-ACP synthetase II and tubulin mRNA expression were calculated, based on qRT-PCR results, to discern the expression differences between callus samples. The highest mRNA up-regulation of the β-ketoacyl-ACP synthetase II mRNA was observed in canola callus samples transformed with the pDAB4695 construct (Table 4). This 27% up-regulation was statistically significant (p=0.05) over that of control samples.

TABLE 4

KASII mRNA expression in *B. napus callus* samples transformed with different ZFP TF constructs

| Construct | Number of calli Analyzed | KasII/Tubulin expression Mean | KasII/Tubulin expression STDEV |
|---|---|---|---|
| 4695 | 23 | 3.69 | 1.20 |
| 4696 | 20 | 2.81 | 0.84 |
| 4697 | 24 | 3.18 | 0.93 |
| 4698 | 24 | 3.03 | 0.68 |
| Control | 14 | 2.90 | 1.12 |

Example 5

Analysis of Transformed T0 Plant Samples 5.1 Analysis of β-Ketoacyl-ACP Synthetase II, Tubulin, and ZFP TF mRNA Expression T0 canola plants containing pDAB4695 transgene construct were grown up to the 6-leaf plant stage and analyzed for mRNA expressions of the β-ketoacyl-ACP synthetase II endogenous gene, tubulin endogenous gene, and ZFP TF transgene. The transgenic plants were compared to control samples that had been transformed with a binary construct containing a pat gene expression cassette (AtUbi10 Promoter v2::pat v3::Atu ORF1 3'UTR v3). Six leaf punches from a standard size paper puncher were sampled on ice from each plant and total mRNA was extracted with Qiagen 96-well RNeasy RNA extraction kit according to the manufacturer's instructions. (Qiagen, Carlsbad, Calif.). The β-ketoacyl-ACP synthetase II, tubulin, and ZFP TF mRNA expression analyses were completed using the protocols described above in Example 4.

Figure 3:
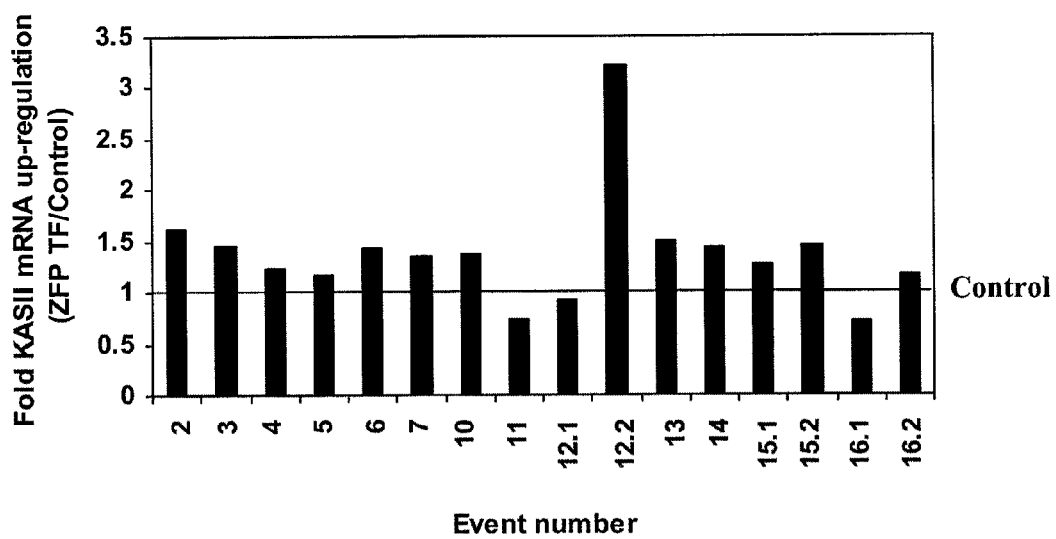
FIG. 3 is a graph depicting KASII mRNA expression in T0 plant leaves transformed with KASII-activating ZFP TF construct 4695, as assayed by qRT-PCR. An average of 27 control plants was used to calculate fold up-regulation shown in the graph. More than 3-fold KASII mRNA up-regulation was observed in certain events.

The expression of β-ketoacyl-ACP synthetase II mRNA varied among independent transgenic T0 plants. Greater than 3-fold mRNA up-regulation was observed among the 16 events analyzed (FIG. 3). All plants were positive for ZFP TF expression. In addition, 27 control plants were used to calculate a β-ketoacyl-ACP synthetase II mRNA expression baseline. The mean expression of the β-ketoacyl-ACP synthetase II mRNA from the baseline control was compared to the expression of β-ketoacyl-ACP synthetase II mRNA from individual ZFP TF plant events to calculate the fold-increase of expression (FIG. 3). These plants were grown to maturity to obtain T1 seed. Prior to flowering, all plants were individually covered with selfing bags to facilitate self pollination of flowers within a plant. T1 seed of these plants were collected approximately 4 months following their transfer to the greenhouse.

Events 3, 6 and 12.2 (hereafter referred to as event 12), representing different β-ketoacyl-ACP synthetase II mRNA expression ranges, were selected for further study.

Example 6

Analysis of Transformed T1 Plant Samples 6.1 Fatty Acid Analysis of T1 Seed

Single seed fatty acid analysis was performed on 24 individual T1 seeds, per event, to study ZFP TF effects on alteration in the fatty acid contents (Table 5). A fatty acid methyl ester (FAME) analysis method based on AOCS method Ce2-66(97) was employed and all numbers in Table 5 are displayed as a percentage of the total fatty acids present in canola seeds.

For sample preparation, individual single seeds were placed into labeled cluster tubes on a 96-well extraction plate containing one ⅛" steel ball (Small Parts, Miramar, Fla.). Tubes were capped and the seed dry ground in a GenoGrinder (SPEX CertiPrep Group, Metuchen, N.J.) for 3.0 minutes at 1300 strokes/minute. The caps were removed and 0.6 mL of heptane was added to each well. The wells were re-capped and placed back into the GenoGrinder for additional grinding for 2.0 minutes at 1200 strokes/min. The samples were then removed and centrifuged at 3700 rpm for 10.0 minutes at 6° C. Using a Beckman Coulter MC Robot, the supernatant was transferred to a 96 well plate with glass inserts (MicroLiter, Suwanee, Ga.). 40 μL of 1% sodium methoxide was added to the sample. The sodium methoxide was diluted from a stock 30% solution with methanol (Fluka/Sigma Aldrich, St. Louis, Mo.). The plates were capped with a Teflon lined mat and allowed to incubate at room temp for 4 hours before GC analysis.

Samples were analyzed for fatty acid contents on an Agilent 6890 GC-FID (Agilent Technologies, Santa Clara, Calif.) equipped with a J&W Scientific DB-23 column, 15 meter× 0.25 mm ID column and 0.25 μm film thickness, (J&W Scientific, Folsom, Calif.). The initial oven temperature was 200° C. and this temperature was maintained for the duration of the run. The inlet was set to split ratio of 1:100 and a temperature of 280° C. A ramped flow rate of 0.8 mL/min helium was maintained for the initial two minutes. The flow was then increased at a rate of 1.0 mL/min to 2.5 mL/min and held for 1.5 minutes. The detector was set to 300° C. with a constant carrier gas make up and column flow of 30 mL/min, fuel hydrogen flow of 30 mL/min, and oxidizer flow of 400 mL/min. An injection volume of 2 μL was used for all samples.

Individual fatty acid methyl ester peaks were identified by comparison with the retention times of methyl ester reference standards (GLC#428, Nu-Chek-Prep, Inc., Elysian, Minn.)

TABLE 5

Fatty acid profile of individual T1 seed measured with FAME analysis

| Events | C16:0 | C16:1 | C18:0 | C18:1 | C18:2 | C18:3 | Total C18 |
|---|---|---|---|---|---|---|---|
| 3 Low | 2.8 | 0.3 | 1.6 | 76.1 | 12.2 | 3.7 | 93.6 |
| 3 Low | 2.9 | 0.3 | 1.4 | 76.7 | 11.8 | 4.0 | 93.9 |
| 3 Low | 2.9 | 0.3 | 1.4 | 75.7 | 13.0 | 3.8 | 93.9 |
| 3 High | 3.6 | 0.3 | 1.4 | 75.1 | 13.0 | 3.5 | 93.1 |
| 3 High | 3.8 | 0.4 | 1.4 | 75.6 | 12.0 | 3.8 | 92.8 |
| 3 High | 4.0 | 0.4 | 1.5 | 74.8 | 12.6 | 3.7 | 92.5 |
| Mean (n = 24) | 3.3 | 0.3 | 1.5 | 75.7 | 12.4 | 3.8 | 93.3 |
| STD Dev (n = 24) | 0.5 | 0.1 | 0.1 | 0.7 | 0.5 | 0.1 | 0.34 |
| 12 Low | 3.1 | 0.2 | 1.5 | 76.4 | 12.0 | 3.8 | 93.6 |
| 12 Low | 3.2 | 0.3 | 1.4 | 77.0 | 11.5 | 3.4 | 93.3 |
| 12 Low | 3.2 | 0.2 | 1.8 | 80.9 | 7.5 | 3.2 | 93.5 |
| 12 High | 3.6 | 0.3 | 1.5 | 76.8 | 11.7 | 3.1 | 93.2 |
| 12 High | 3.6 | 0.3 | 1.6 | 76.0 | 11.9 | 3.5 | 93.0 |
| 12 High | 3.6 | 0.3 | 1.8 | 77.3 | 10.8 | 3.0 | 92.9 |
| Mean (n = 24) | 3.4 | 0.3 | 1.6 | 77.4 | 10.9 | 3.3 | 93.2 |
| STD Dev (n = 24) | 0.2 | 0.0 | 0.2 | 1.8 | 1.7 | 0.3 | 0.23 |
| 6 Low | 3.2 | 0.5 | 1.9 | 81.3 | 8.1 | 2.1 | 93.3 |
| 6 Low | 3.3 | 0.5 | 1.2 | 79.6 | 10.1 | 2.3 | 93.1 |
| 6 Low | 3.5 | 0.5 | 2.6 | 80.6 | 7.5 | 1.9 | 92.6 |
| 6 High | 4.4 | 0.5 | 2.4 | 77.7 | 10.7 | 1.5 | 92.2 |
| 6 High | 4.5 | 0.6 | 2.2 | 77.1 | 10.5 | 1.8 | 91.6 |
| 6 high | 4.6 | 0.7 | 1.3 | 77.4 | 11.0 | 1.7 | 91.4 |
| Mean (n = 24) | 3.9 | 0.5 | 1.9 | 78.9 | 9.6 | 1.9 | 92.4 |
| STD Dev (n = 24) | 0.6 | 0.1 | 0.6 | 1.8 | 1.5 | 0.3 | 0.54 |
| Nex710 Mean (n = 216) | 3.8 | 0.4 | 2.3 | 78.1 | 9.5 | 2.5 | 92.5 |
| STD Dev (n = 216) | 0.2 | 0.0 | 0.6 | 1.8 | 1.6 | 0.7 | 0.45 | using Waters Corp. Empower Software. Individual percent areas were calculated for all analytes in the reference standard based upon the total integrated chromatography peak areas. A heptane blank was also shot to identify any contamination on the GC.

A comparison of T1 seed with the three lowest C16:0 levels (which are most likely ZFP TF positive plants) and the three highest C16:0 levels (which are most likely ZFP TF null plants) indicated that changes in the C 16:0 content could be due to the segregation of the ZFP TF transgene (Table 5). A corresponding change in total C18 (C18:0+C18:1+C18:2+C18:3) was also observed in all events; seeds with low C16:0 levels had increased total C18 levels and vice versa. This was despite the variability in individual fatty acid contents of C18:0, C18:1, C18:2 and C18:3 due to the segregation of fad2 and fad3 mutant genes (Hu, X., et al. Theor. Appl. Genet. 2006, 113: 497-507) in the Nex710 genotype that was transformed. Therefore, the next step was undertaken to identify the ZFP TF positive and sibling null plants in a T1 segregating population of each event to detect the actual change in the fatty acid profile in similar genetic backgrounds.

6.2 ZFP TF Presence Analysis in T1 Plants 100-150 T1 seedlings of all three transgenic events 3, 6, and 12, were screened to identify ZFP TF positive and sibling null plants (Table 6). Plants were tested for the presence of at least one full-length cassette of the ZFP TF transgene. Total genomic DNA from the leaves of these plants was isolated as per manufacturer's recommendations with the QIAGEN PLANT DNEASY extraction kit (Qiagen, Valencia, Calif.). The protocol was modified by adding PVP-40 to the Qiagen buffer AP1 at a final concentration of 1%. The purified gDNA was quantified by a PICOGREEN® DNA Quantification protocol (Molecular Probes, Inc., Eugene, Oreg.). The DNA samples were assayed for the presence of at minimum, one full-length copy of the ZFP TF transgene in a PCR assay containing the following reagents: 5 µL 10× EX Taq buffer (Takara Bio Inc., Otsu, Siga, Japan), 5 µL 10% polyvinyl pyrrolidone-40, 1.0 µL ubi10 forward primer (SEQ ID NO: 35: 5'-GGTCAACGGATCAGGATATTCTTG-3') from 10 µM stock, 1.0 µL AtuORF23 reverse primer (SEQ ID NO: 36: 5'-CCATGTTGGCAAAGGCAACC-3'), 10 µM stock, 4 uL of dNTPs (2.5 mM each), 0.2 µL TaKaRa EX Taq™ Hot Start, 31.8 µL water and 2 µL DNA at a concentration of 10 ng/µL. PCR cycling conditions were as follows: 94° C. for 2 min, 10 cycles of touch-down PCR with 98° C. for 10 sec, 65° C. for 20 sec with decreasing temperature of 0.5° C. at every cycle to 60° C. followed by 72° C. for 3:00 min. This was followed by 35 cycles of 98° C. for 10 sec, 60° C. for 20 sec and 72° C. for 3:00 min and a final extension of 72° C. for 10 min. 5 µl of each reaction was run on a 1% agarose gel to detect for the presence of the expected size ZFP TF band of 2662 bp.

A quantitative Real Time-PCR assay for the pat gene, which is molecularly linked to the ZFP TF in the pDAB4695 construct, was developed and applied to identify pat positive and null plants to confirm its genetic segregation with the ZFP TF cassette to which it is molecularly linked.

The reaction mix for pat TaqMan RT-PCR assay was comprised of the following: 3 µL Roche LIGHTCYCLER® Cycler 480 II Probes 2× master mix, 0.64 µL 10% PVP-40, 0.2 µL each of pat forward primer (SEQ ID NO: 37: 5'-ACAAGAGTGGATTGATGATCTAGAGAGGT-3') from 10 µM stock, 0.2 µL PAT reverse primer (SEQ ID NO: 38: 5'-CTTTGATGCCTATGTGACACGTAAACAGT-3') from 10 µM stock, 0.2 µL probe (SEQ ID NO: 39: 5'-6FAM-CCAGCGTAAGCAATACCAGCCACAACACC-quencher-3') from 5 µM stock, and it was multiplexed with the following reagents for internal reference standard of HMG (GenBank: AF127919), as follows: 0.2 µL each of HMG forward primer (SEQ ID NO: 40: 5'-CCTCTCTACCAC-CGTCTCACATG-3') from 10 µM stock, 0.2 µL HMG reverse primer (SEQ ID NO: 41: 5'-GATCTGGCCGGACT-GTTTCA-3') from 10 µM stock, 0.2 µL probe (SEQ ID NO: 42: 5'-6FAM-CGCTCCTCAGCTACCACCTCAACCA-quencher-3'), from 5 µM stock, 1 µL DNA and 0.2 µL water. PCR cycling conditions were: 1 cycle of 95° C. for 5 min, 40 cycles of 95° C. for 10 sec, 60° C. for 40 sec and 72° C. for 1 sec. All samples were amplified in triplicate in 384-well plates along with 1-4 copy transgenic genomic DNA standards in a Roche LIGHTCYCLER® 480 PCR machine.

Based on the segregation ratios of the ZFP TF positive and null plants within each event, events 3, 6 and 12 contained approximately 2, 1, and 2 insertions respectively of the ZFP TF transgene in the *B. napus* genome (Table 6, Column 3). This data matched with the pat gene segregation data in all three events.

6.3 β-Ketoacyl-ACP Synthetase II mRNA Up-Regulation in T1 Plants

All T1 ZFP TF positive and sibling null plants shown in Table 6, Column 3 were then subjected to mRNA expression analysis for the endogenous β-ketoacyl-ACP synthetase II gene, ZFP TF transgene, and endogenous tubulin gene. The latter served as a reference gene to normalize for β-ketoacyl-ACP synthetase II and ZFP TF gene expressions. Six leaf punches from each of the 6-leaf plant stage were sampled on ice and total RNA was extracted using the QIAGEN RNAE-ASY® kit. cDNA strand synthesis and dilutions were completed as described in Example 4.1.

qRT-PCR analysis of the synthesized cDNA was completed for all three genes. The β-ketoacyl-ACP synthetase II and tubulin mRNA expression analysis were performed as described in Examples 4.2 and Example 4.3, respectively. The ZFP TF assay was modified. The PCR reaction was set up as follows: The reaction conditions were as follows: 7.5 µL of 2×LC480 Probes Master Buffer (Roche Diagnostic, Indianapolis, Ind.), 0.3 µL, gene specific forward Primer #1 (SEQ ID NO: 43: 5'-TCGATCTTGATATGTTGGGAGA-3') (10 µM stock), 0.3 µL gene specific reverse Primer #2 (SEQ ID NO: 44: 5'-AGGTGCAGAATCATGTGGTG-3') (10 µM stock), 0.15 µL UPL probe #85, 1.5 µL of 10% (w/v) PVP-40, and 3.9 µL water. A 384-well micro-plate was demarcated and 13.5 µL of the mix described above was added per well. A sealing foil was attached to the plate, and the plate was centrifuged for 1 minute at 3000 rpm. The film was removed and 1.5 µL of the thawed, diluted first strands were added per well. In addition, cDNA standards were added to separate control wells. The foil seal was sealed upon the plate and the centrifugation step was repeated. A PCR program was run with the following conditions; i. activate 95° C. for 5 minutes, ii. denature 95° C. for 10 sec (@ 4.8° C./sec), iii. anneal/extend 60° C. for 25 sec (@ 2.5° C./sec), iv. acquire 72° C. for 1 sec (@ 4.8° C./sec), v. repeat steps ii-iv 39-49 more times, vi. cool to 38° C. for 5 sec.

TABLE 6

Identification of ZFP TF positive and sibling null plants in T1 segregating population of the three events

| Events | Total T1 seed planted | T1 ZFP TF/null plants identified | T1 ZFP TF/null plants advanced to T2 seed |
|---|---|---|---|
| 3 | 150 | 115/7 | 12/7 |
| 6 | 100 | 66/27 | 5/5 |
| 12 | 150 | 126/6 | 8/6 |

Figure 4:
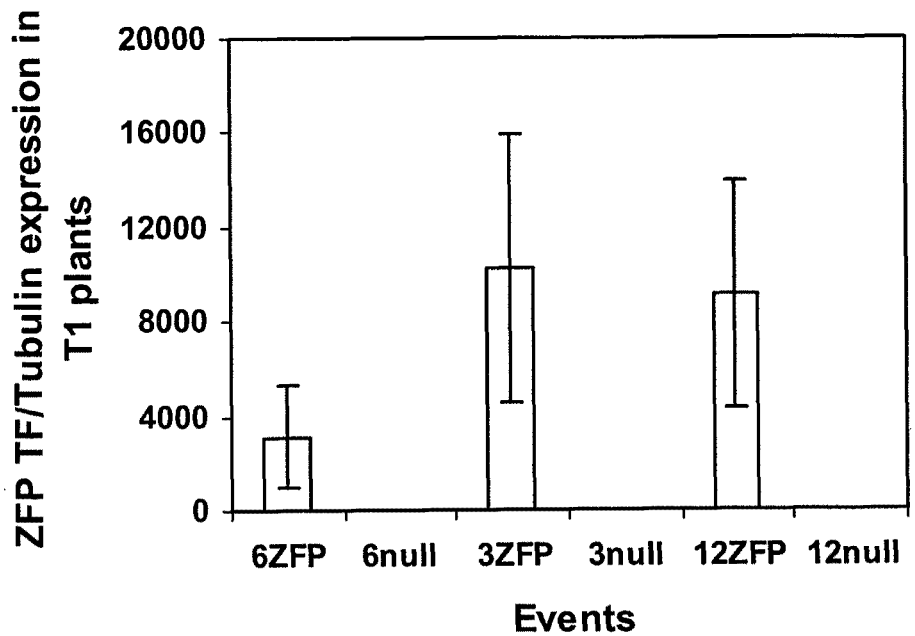
FIG. 4 is a graph depicting KASII-ZFP TF/tubulin expression ratios in T1 plant leaves detected via qRT-PCR. Three events were compared along with corresponding nulls.
Figure 5:
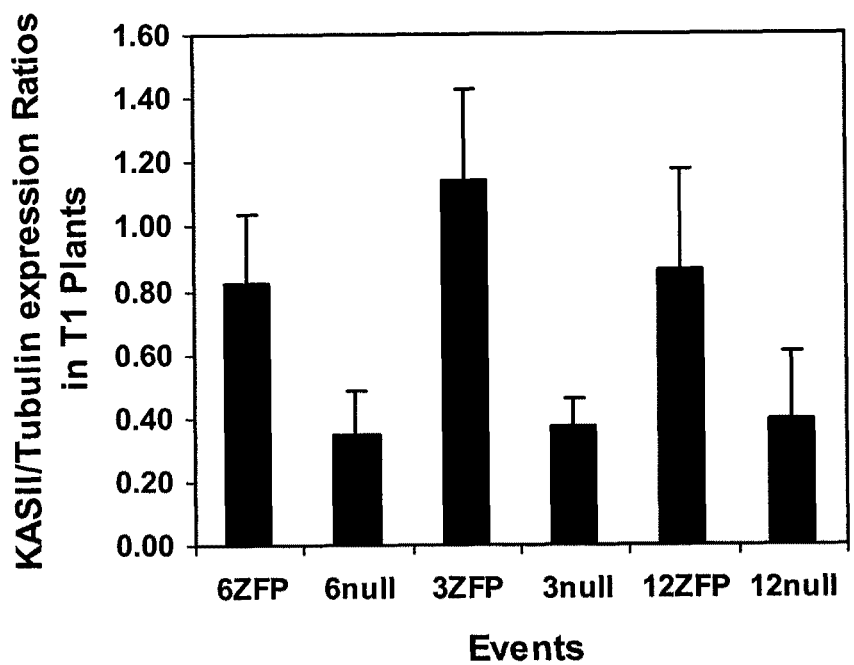
FIG. 5 is a graph depicting the average KASII/tubulin mRNA expression ratios in ZFP TF-containing and segregating null T1 plants of each of three event as determined by qRT-PCR. 2-3 fold KASII mRNA up-regulation was observed in these T1 plant leaves.

ZFP TF mRNA expression was lowest in event 6 and highest in event 3 of the ZFP TF positive samples (FIG. 4). The null plants did not express ZFP TF mRNA indicating that the ZFP TF assay was specific to ZFP TF transgene presence. The mRNA levels of the β-ketoacyl-ACP synthetase II gene, the target for ZFP TF, up-regulated in ZFP TF positive plants of all events (FIG. 5). Up to a 3-4 fold increase in β-ketoacyl-ACP synthetase II mRNA expression was observed by pair-wise comparisons of the ZFP TF positive and corresponding sibling null plants within each event. The up-regulation of β-ketoacyl-ACP synthetase II mRNA levels was relative to the increase in ZFP TF mRNA expression levels within each event (FIG. 4), i.e. lowest in event 6 and highest in event 3.

6.4 Fatty Acid Analysis of T1 Plant Leaves

A second set of T1 leaf samples were collected for fatty acid analysis concurrent to the collection of mRNA analysis samples described in Example 6.3. However, only a subset of the samples were analyzed for fatty acids for only those plants that were advanced to maturity as shown in Table 6, column 4. Fatty acid methyl ester (FAME) analysis of leaf material was completed as follows. Leaf material of 10-100 mg was collected on ice and then freeze dried prior to a transmethylation reaction with 0.25M sodium methoxide in anhydrous methanol at 40° C. for 20 minutes. After the transmethylation reaction the fatty acids were extracted three times with a heptane solution containing heptadecanoin as a surrogate standard. The isolated hexane fractions were dried down and resuspended in a known volume of heptane. The resulting fatty acids methyl ester (FAME) was analyzed via GC-FID using a BPX 70 capillary column from SGE (15 m×0.25 mm×0.25 µm). Each FAME was identified by their retention time and quantified by the injection of a rapeseed oil reference mix from Matreya LLC as the calibration standard. The completeness of the reaction was verified by checking the presence of endogenous FAMES in a fourth extraction/derivation.

All three events showed a decrease in total C16:0 contents and a concomitant increase in total C18 contents in pair-wise comparisons of ZFP TF positive and corresponding sibling null plants within each event (Table 7). For example, event 12 ZFP TF positive plants demonstrated a reduction in C16:0 content by 6.3% and an increase in total C18 content by 1.44% compared to its own sibling null plants.

TABLE 7

T1 leaf fatty acid profile

| Sample name | Plants Analyzed | C16:0 Mean | C16:0 Std Dev | Total C18 Mean | Total C18 Std Dev |
|---|---|---|---|---|---|
| 12null | 6 | 10.98 | 0.31 | 69.93 | 0.91 |
| 12ZFP | 8 | 10.29 | 0.39 | 70.94 | 1.02 |
| 3null | 7 | 10.79 | 0.56 | 69.84 | 1.18 |
| 3ZFP | 12 | 10.34 | 0.29 | 71.25 | 0.74 |
| 6null | 5 | 11.94 | 0.47 | 70.36 | 1.91 |
| 6ZFP | 5 | 10.44 | 0.62 | 72.16 | 2.88 |

Example 7

Analysis of ZFP TF Transgenic T2 Seed

A subset of ZFP TF positive plants demonstrating the highest β-ketoacyl-ACP synthetase II mRNA expressions and sibling null plants within each event were advanced to maturity to obtain T2 seed (Table 6, column 4). The exception was event 3, where a few ZFP TF positive plants with lower expression ranges were also advanced. These could represent the other segregating insertion of the pDAB4695 transgene. Each T1 plant was covered with a meshed bag to facilitate self pollination within a given plant. Seeds were harvested and fatty acid levels were assayed.

Figure 6:
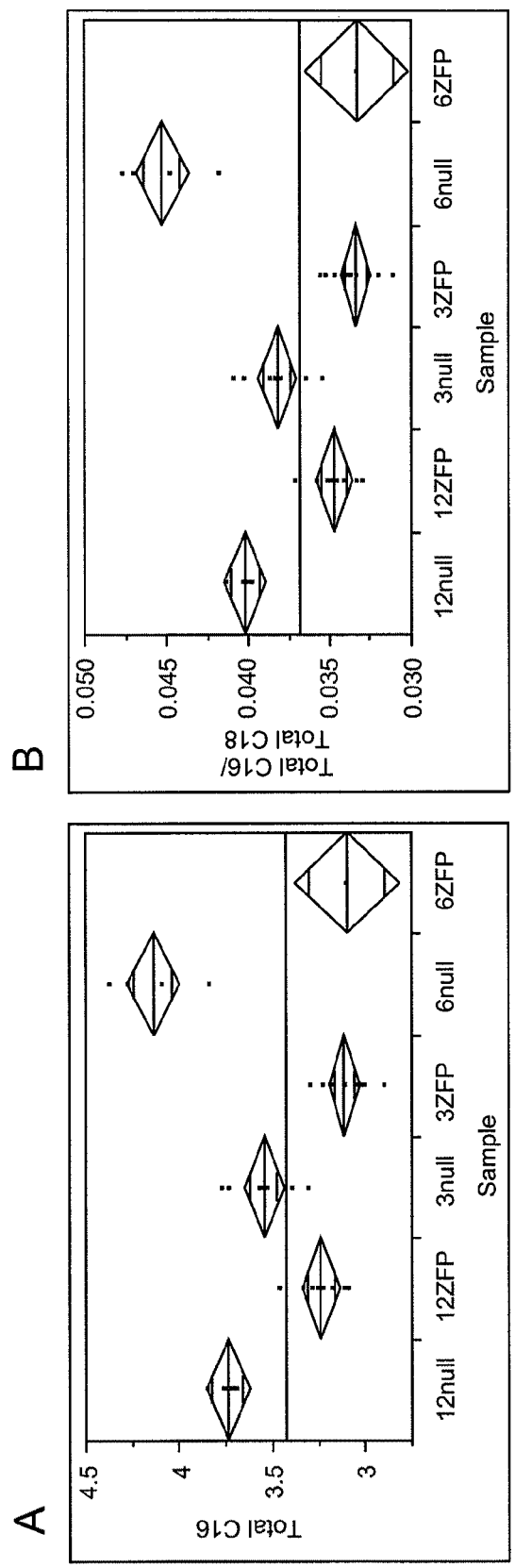
FIGS. 6A and 6B are graphs, drawn with JMP statistical software for one-way analysis of target fatty acid(s), depicting a consistent and significant ($p=<0.001$) decrease in Total C16 (6A) and decrease in Total C16/Total C18 ratios (6B) in ZFP TF positive and sibling null plants within each event. Total C16 was comprised of C16:0 and C16:1 contents and total C18 was comprised of C18:0, 18:1, 18:2 and 18:3 contents.

T2 fatty acid analysis was performed on a pool of 24 seeds per plant as described for T1 seed analysis in Example 6.1. The results showed a decrease in C16:0 content in ZFP TF positive plants of all three events by pair-wise comparison with their corresponding sibling null plants (Tables 8A and 8B). This decrease in C16:0 contents was 12.6%, 11.2% and 22.3% for events 12, 3 and 6, respectively. A consistent decrease was also observed in C16:1 content. Corresponding to the decrease in the C16:0 and C16:1 contents, a concomitant increase in total C18 (C18:0+C18:1+C18:2+C18:3) content was observed in ZFP TF positive plants in a pair-wise comparison with the corresponding sibling null plants. All three pair-wise comparisons of ZFP TF positive and corresponding sibling null plants were statistically significant (p=<0.001) for increases in total C16 (C16:0+C16:1) content, and total C16/total C18 content upon analysis with JMP statistical software (FIGS. 6, A and B). Although the three events were variable in their C16:0 content based on sibling null plant observations (Tables 8A and 8B), ZFP TF was efficacious in decreasing the C16:0 content to approximately similar levels; between ~2.93 to 3.05. While all ZFP TF positive plants of events 3 and 12 set seeds (Tables 8 and 9), only one ZFP TF containing plant of event 6 set seed. This particular plant of event 6 was highest in the C16:0 content based on T1 leaf fatty acid data. Tables 8A and 8B show comparison of T2 fatty acid profile of three *B. napus* transgenic events of pDAB4695 ZFP TF positive and corresponding sibling null plants. This data was obtained with FAME analysis and is described in Section 6.1. C12:0 to C24:1 fatty acids were analyzed and major ones are shown in these tables. All numbers were represented as a percentage of total fatty acids present in *B. napus* seeds.

TABLE 8A

C16:0, C16:1, C18:0, C:18:1, C:18:2 and C:18:3 fatty acid analysis

| Samples | C16:0 | C16:1 | C18:0 | C18:1 | C18:2 | C18:3 |
|---|---|---|---|---|---|---|
| 12Null Mean | 3.49 | 0.26 | 1.29 | 76.59 | 11.45 | 3.73 |
| Std. Dev. (n = 6) | 0.06 | 0.01 | 0.05 | 0.25 | 0.21 | 0.04 |
| 12ZFP Mean | 3.05 | 0.20 | 1.33 | 76.53 | 11.63 | 3.87 |
| STD DEV (n = 8) | 0.11 | 0.02 | 0.04 | 0.39 | 0.33 | 0.06 |
| 3Null Mean | 3.30 | 0.25 | 1.31 | 74.34 | 13.18 | 3.94 |
| Std. Dev. (n = 7) | 0.17 | 0.02 | 0.10 | 1.04 | 0.86 | 0.25 |
| 3ZFP Mean | 2.93 | 0.18 | 1.30 | 74.10 | 13.62 | 4.14 |
| STD DEV (n = 12) | 0.12 | 0.01 | 0.08 | 1.80 | 1.45 | 0.25 |
| 6Null Mean | 3.77 | 0.38 | 2.02 | 73.46 | 12.42 | 3.66 |
| Std. Dev. (n = 4) | 0.15 | 0.08 | 0.14 | 2.80 | 2.44 | 0.66 |
| 6ZFP (n = 1) | 2.93 | 0.17 | 1.07 | 77.89 | 10.65 | 3.24 |

TABLE 8B

C20:0, C20:1, C20:2, C22:0, C22:1, C24:0 and C24:1 fatty acid analysis

| Samples | C20:0 | C20:1 | C20:2 | C22:0 | C22:1 | C24:0 | C24:1 |
|---|---|---|---|---|---|---|---|
| 12Null Mean | 0.53 | 1.26 | 0.05 | 0.33 | 0.02 | 0.14 | 0.14 |
| Std. Dev. (n = 6) | 0.03 | 0.07 | 0.01 | 0.04 | 0.01 | 0.02 | 0.02 |
| 12ZFP Mean | 0.55 | 1.37 | 0.06 | 0.36 | 0.02 | 0.15 | 0.16 |
| STD DEV (n = 8) | 0.02 | 0.05 | 0.01 | 0.02 | 0.01 | 0.01 | 0.02 |
| 3Null Mean | 0.59 | 1.49 | 0.06 | 0.43 | 0.02 | 0.15 | 0.21 |
| Std. Dev. (n = 7) | 0.07 | 0.11 | 0.01 | 0.07 | 0.01 | 0.03 | 0.04 |
| 3ZFP Mean | 0.57 | 1.57 | 0.07 | 0.42 | 0.03 | 0.15 | 0.19 |
| STD DEV (n = 12) | 0.04 | 0.21 | 0.02 | 0.07 | 0.01 | 0.04 | 0.04 |
| 6Null Mean | 0.80 | 1.49 | 0.07 | 0.54 | 0.03 | 0.30 | 0.24 |
| Std. Dev. (n = 4) | 0.08 | 0.13 | 0.01 | 0.08 | 0.01 | 0.07 | 0.02 |
| 6ZFP (n = 1) | 0.52 | 1.86 | 0.07 | 0.42 | 0.04 | 0.20 | 0.22 |

Table 9 displays total fatty acid profiles based on the individual fatty acids shown in Tables 8A and 8B.

TABLE 9

| Samples | Total C18* | Total LC** | Total Sats*** |
|---|---|---|---|
| 12Null Mean | 93.06 | 95.52 | 5.83 |
| STD DEV (n = 6) | 0.13 | 0.05 | 0.09 |
| 12ZFP Mean | 93.36 | 96.01 | 5.48 |
| STD DEV (n = 8) | 0.11 | 0.13 | 0.09 |
| 3Null Mean | 92.78 | 95.74 | 5.82 |
| STD DEV (n = 7) | 0.39 | 0.17 | 0.32 |
| 3ZFP Mean | 93.16 | 96.14 | 5.41 |
| STD DEV (n = 12) | 0.41 | 0.13 | 0.19 |
| 6Null Mean | 91.55 | 95.01 | 7.47 |
| STD DEV (n = 4) | 0.36 | 0.29 | 0.40 |
| 6ZFP (n = 1) | 92.85 | 96.18 | 5.17 |

*Total C18 represents a sum of following carbons: C18:0, C18:1, C18:2 and C18:3.
**Total LC or long chain represents a sum of the following carbons: total C18 + total C20 (C20:0 + C20:1 + C20:2) + total C22 (C22:0 + C22:1) + total C24 (C24:0 + C24:1)
***Total Sats represents all saturated fatty acids shown in Tables 8A and 8B.

Combining all long chain fatty acids (total C18, total C20, total C22 and total C24), an increase of 0.4% to 1.2% was observed in ZFP TF positive plants of different events compared to sibling nulls. Among the longer chain fatty acids, an increase of C20:1 by 25% was noticeable in ZFP TF positive plants for event 6. A decrease in total saturated fatty acid content was also observed in ZFP TF containing plants in all events. It ranged from a 6% reduction in event 12 to 31% reduction in event 6.

In summary, ZFP TF-mediated transcriptional up-regulation of the β-ketoacyl-ACP synthetase II gene in T0 and T1 plants and the concomitant decrease in total C16 and increase in total C18 fatty acid contents in T2 seed was exemplified. These data demonstrate the successful application of novel ZFP TF technologies to target and modify specific genes in the fatty acid biosynthesis pathway resulting in predicted changes in seed oil profiles, which are heritable across generations of progeny.

Examples 8-15

FatB Up-Regulation/Down-Regulation

Plastids are the major site for de novo fatty acid biosynthesis in higher plants (Ohlrogge et al., 1979, Proc Natl Acad Sci USA 76:1194-8; Thelen and Ohlrogge, 2002, Metabolic Engineering 4:12-21). Fatty acids not utilized in the plastids are exported to cytoplasm through the specific activity of acyl-ACP thioesterases (EATs) by hydrolyzing acyl-acyl carrier proteins (acyl-ACP) to release free fatty acids. There are two classes of FAT enzymes in plants, FATA and FATB. The FATA class prefers 18:1-ACP in vitro while the FATB class prefers saturated acyl-ACP substrates, such as 16:0-ACP and 18:0-ACP, but also shows other heterogeneous substrate specificity (Doermann et al, 1995, Arch. Biochem. Biophys. 316:612-618; Voelker et al., 1997, Plant Physiology 114:669-677; Salas and Ohlrogge, 2002, Archives of Biochemistry and Biophysics, 403:25-34). Similar to FATA, FATB is also regarded to be present in all plant tissues, but predominantly expresses in developing seeds (Jha et al., 2006, Plant Physiology and Biochemistry 44:645-655).

The Arabidopsis nuclear genome encodes for two FatA genes and a single FatB gene. Inactivation of the FatB activity can dramatically decrease saturated fatty acid content in glycerolipids. For example, in a FatB mutant created by the insertion of a T-DNA, palmitate (16:0) and stearate (18:0) content were reduced by 42-56% and 30-50% respectively depending on the tissue (Bonaventure et al., The Plant Cell, 2003 15:1020-1033). The plant growth rate was greatly impacted in this mutant resulting in 50% less fresh weight at 4 weeks compared to wild-type. This finding supports the view that FatB serves as a major factor governing the fate of the saturated fatty acids in plants.

The major oilseed crop Brassica napus is an amphidiploid species closely related to the model species Arabidopsis, but has a genome size of approximately eight times larger than that of Arabidopsis. As a result, six FatB genes have been reported in this species (WO 2009/007091) compared to one in Arabidopsis. This complexity makes it difficult to understand the function of individual FatB genes for their manipulation. Conversely, the presence of a higher number of genes makes it easier to manipulate the expression of multiple gene toward the desired fatty acid goal instead of knocking one out completely. Zinc finger transcription factors have been known to bind to essentially any DNA sequence and modulate gene function of the targeted genes (Van Eenennaam et al., Metab. Eng. 2004 6:101-108; Sanchez et al., 2006, Plant Biotechnology Journal 4:103-114). As a result, this tool can be applied to FatB genes for understanding their function in B. napus. This knowledge would assist in manipulating the expression of one to multiple FatB genes towards desired "healthier" canola seed oil that is lower in saturated fatty acids.

Examples 8-15 following demonstrate transcriptional up-regulation of FatB genes in *Brassica napus* L. resulting in fatty acid profile changes in seeds.

Example 8

Target Sequence Identification for FatB Genes in *Brassica napus* L 8.1 Target Sequence Identification A modified Genome Walking protocol was employed to discover and characterize the promoter sequences for the FatB genes of *Brassica napus* variety Nex710. These nucleotide sequences were isolated and identified for the design and production of ZFP TFs, which can be used to modify gene expression of the FatB gene. Nine genome walking libraries were constructed using the Clontech Genome Walking Kit (Palo Alto, Calif.). These libraries were used to obtain ~1 kb of sequence upstream of the transcription start site for the FatB genes. A forward pair of nested FatB gene-specific primers were designed and synthesized based on available FatB EST sequences from public databases. A reverse pair of nested primers were designed and synthesized to hybridize to the adapter sequences. Multiple PCR fragments were amplified from the nine libraries. The resulting PCR fragments were cloned into TOPO vectors (Invitrogen, Carlsbad, Calif., USA) and sequenced to identify the FatB promoter sequences. Two different FatB genes, FatB4 and FatB5, were identified based on this approach. It was observed that although the coding sequences of these FatB genes were highly conserved, the sequences diverged in the 5' UTR and promoter regions.

FatB expression and quantitation of the FatB4 and FatB5 genes via quantitative RT-PCR analysis in developing *B. napus* seed suggested that the genes were highly expressed in *B. napus* seed. Total RNA was isolated, quantified, and the transcription initiation sites were mapped as described above in Example 1. The promoter sequences of these two genes were utilized to design ZFP TFs for transcriptional expression modification.

Example 9

Design of ZFP DNA Binding Domains Specific to FatB Genes

Zinc finger proteins were designed against various targets sites in the FatB gene. The target sites and recognition helices for representative ZFP designs are shown below in Tables 10A and 10B.

TABLE 10A

| | Target binding sites for FatB ZFP TFs | | |
|---|---|---|---|
| ZFP | FatB4 Target Site (5' to 3') | FatB 5 Target site (5' to 3') | FatB specificity |
| 13685* | aaCGAAAGgAGATCG AGAGAGgagagag (SEQ ID NO: 47) | No binding site | FatB4 |
| 13714 | No binding site | cgAAAGGGAGATCGA GAGAGgcaccgca (SEQ ID NO: 48) | FatB5 |
| 13722 | aaGGAGAAcTTTAGG GTTTGGggagact (SEQ ID NO: 49) | aaGGAGAAtTTTAGG GTTTGGggagact (SEQ ID NO: 50) | FatB4 and FatB5 |
| 13743** | ctCCGAAGAGATTGG CGTAAcacttcgt (SEQ ID NO: 51) | ctCCGAAGAGATTGG CGTAAccttcatt (SEQ ID NO: 52) | FatB4 and FatB5 |

TABLE 10B

| | ZFP recognition helix regions | | | | | |
|---|---|---|---|---|---|---|
| ZFP | 1*** | 2 | 3 | 4 | 5 | 6 |
| 13685 | RSDNLSA (SEQ ID NO: 75) | QSAHRKT (SEQ ID NO: 76) | RSDDLSK (SEQ ID NO: 21) | QSSHRKT (SEQ ID NO: 77) | RSDHLSV (SEQ ID NO: 78) | QNAHRIE (SEQ ID NO: 79) |
| 13714 | RSDNLSA (SEQ ID NO: 75) | QSAHRKT (SEQ ID NO: 76) | RSDDLSK (SEQ ID NO: 21) | QSSHRKT (SEQ ID NO: 77) | RSDHLSK (SEQ ID NO: 80) | QNANRIT (SEQ ID NO: 81) |
| 13722 | RSDHLST (SEQ ID NO: 82) | HSNTRKN (SEQ ID NO: 83) | RSDHLSQ (SEQ ID NO: 84) | NSASRKN (SEQ ID NO: 85) | QSGNLAR (SEQ ID NO: 16) | QSGHLSR (SEQ ID NO: 86) |

TABLE 10B-continued

ZFP recognition helix regions

| ZFP | 1*** | 2 | 3 | 4 | 5 | 6 |
|---|---|---|---|---|---|---|
| 13743 | NSDSLTE (SEQ ID NO: 87) | RRADLSR (SEQ ID NO: 88) | RSDSLSA (SEQ ID NO: 89) | QNAHRKT (SEQ ID NO: 90) | RSDHLSQ (SEQ ID NO: 84) | RNADRIT (SEQ ID NO: 91) |

*Capital letters represent the ZFP binding sequence while flanking small letters represent the flanking sequence context for ZFP TF binding site. The small italics letters in between the capital letters represent the skipped bases in the ZFP design.
**ZFP binding sequence is the same between FatB4-and FatB5, but the 3' flanking sequences are different between the two genes.
***numbers represent the zinc finger numbers represent the zinc finger (1 is finger 1, 2 is finger 2, etc.)

Example 10

ZFP TF-Mediated Up-Regulation of Native FatB Genes in B. napus

To exemplify ZFP TF-mediated up-regulation of FatB within *B. napus* cells, constructs were built containing four designs of ZFP TF genes (Tables 10 and 11), these genes were stably delivered into *B. napus* cells through *Agrobacterium*-mediated transformation.

10.1 Construct Design

The ZFP TF binary plasmids designed and constructed are listed in Table 11 below. Expression of the ZFP TF genes was driven by a relatively strong constitutive promoter, such as a promoter derived from the Cassaya Vein Mosaic Virus (CsVMV) promoter. *Agrobacterium*-mediated plant transformation was conducted as described in Example 3.2 to stably incorporate ZFP TFs into the *B. napus* genome.

TABLE 11

Construct description of ZFP TFs targeted to *B. napus* FatB genes

| S.N. | ZFP | Construct No. | Gene Cassette |
|---|---|---|---|
| 1 | 13685 | pDAB4689 | RB7 MAR/CsVMV/Op-2 NLS-ZFP 13685 VP16/AtuORF23 3' UTR/AtUbi10/Pat/AtuORF1 3' UTR |
| 2 | 13714 | pDAB4690 | RB7 MAR/CsVMV/Op-2 NLS-ZFP 13714-VP16/AtuORF23 3' UTR/AtUbi10/Pat/AtuORF1 3' UTR |
| 3 | 13722 | pDAB4691 | RB7 MAR/CsVMV/Op-2 NLS-ZFP 13722-VP16/AtuORF23 3' UTR/AtUbi10/Pat/AtuORF1 3' UTR |
| 4 | 13743 | pDAB4692 | RB7 MAR/CsVMV/Op-2 NLS-ZFP 13743-VP16/AtuORF23 3' UTR/AtUbi10/Pat/AtuORF1 3' UTR | pDAB4689 is a binary plasmid which contains the opaque-2 (Op-2) Nuclear Localization Sequence or NLS/13685/VP 16 and pat gene expression cassettes. This construct includes the following gene elements; RB7 MAR v3 (Matrix Attachment Region (Thompson et al., 1997, WO9727207))::CsVMV Promoter v2 (Cassaya Vein Mosaic Virus Promoter (Verdaguer et al., 1996, *Plant Molecular Biology* 31: 1129-1139))::opaque-2 NLS (Van Eenennaam et al., 2004, *Metabolic Engineering* 6:101-108; Holmes-Davis et al., 2005, *Plant Molecular Biology* 57:411-423)/13685 Zinc FingerNP16 (Jamieson et al., *Biochem. Biophy. Res. Commun.* 2006, 348:873-879) Fusion::AtuORF23 3'UTR v1 (*Agrobacterium tumefaciens* Open Reading Frame 23, 3'UnTranslated Region (Gelvin et al., 1987, EP222493))::AtUbi10 Promoter v2 (*Arabidopsis thaliana* Ubiquitin-10 Promoter (Callis, et al., 1990, *J. Biol. Chem.* 265-12486-12493))::pat v5 (Phosphinothricin Acetyl Transferase (Wohlleben et al., 1988, Gene 70:25-37))::AtuORF 1 3'UTR v4 (*Agrobacterium tumefaciens* Open Reading Frame 1, 3'UnTranslated Region (Huang et al., *J. Bacteriol.* 172:1814-1822)). The binary was constructed by cloning a DNA fragment containing the opaque-2 NLS/13685 Zinc FingerNP16 fusion into pDAB3912 via NcoI-SacI restriction sites. The resulting construct which was labeled as pDAB8215 contained the CsVMV Promoter v2::opaque-2 NLS/13685 Zinc Finger/VP16 Fusion::AtuORF23 3'UTR v1 gene expression cassette. pDAB8215 was cloned into the pDAB4668 binary via an L-R Gateway Reaction (Invitrogen, Carlsbad, Calif.). This reaction produced pDAB4689 and was confirmed via restriction enzyme digestions and sequencing reactions.

pDAB4690 is a binary plasmid which contains the opaque-2 NLS/13714/VP 16 and pat gene expression cassettes. This construct includes the following gene elements; RB7 MAR v3::CsVMV Promoter v2::opaque-2 NLS/13714 Zinc FingerNP16 Fusion::AtuORF23 3'UTR v1::AtUbi10 Promoter v2::pat v5::AtuORF 1 3'UTR v4. The binary was constructed by cloning a DNA fragment containing the opaque-2 NLS/13714 Zinc FingerNP16 fusion into pDAB3912 via NcoI-SacI restriction sites. The resulting construct which was labeled as pDAB8216 contained the CsVMV Promoter v2::opaque-2 NLS/13714 Zinc FingerNP16 Fusion::AtuORF23 3'UTR v1 gene expression cassette. pDAB8216 was cloned into the pDAB4668 binary via an L-R Gateway Reaction (Invitrogen, Carlsbad, Calif.). This reaction produced pDAB4690 and was confirmed via restriction enzyme digestions and sequencing reactions.

pDAB4691 is binary plasmid which contains the opaque-2 NLS/13722/VP 16 and pat gene expression cassettes. This construct includes the following gene elements; RB7 MAR v3::CsVMV Promoter v2::opaque-2 NLS/13722 Zinc FingerNP16 Fusion::AtuORF23 3'UTR v1::AtUbi10 Promoter v2::pat v5 (Phosphinothricin Acetyl Transferase::AtuORF 1 3'UTR v4. The binary was constructed by cloning a DNA fragment containing the opaque-2 NLS/13722 Zinc FingerNP16 fusion into pDAB3912 via NcoI-SacI restriction sites. The resulting construct which was labeled as pDAB8217 contained the CsVMV Promoter v2::opaque-2 NLS/13722 Zinc Finger/VP16 Fusion::AtuORF23 3'UTR v1 gene expression cassette. pDAB8217 was cloned into the pDAB4668 binary via an L-R Gateway Reaction (Invitrogen, Carlsbad, Calif.). This reaction produced pDAB4691 and was confirmed via restriction enzyme digestions and sequencing reactions.

pDAB4692 is a binary plasmid which contains the opaque-2 NLS/13743/VP 16 and pat gene expression cassettes. This construct includes the following gene elements; RB7 MAR v3 (Matrix Attachment Region::CsVMV Promoter v2::opaque-2 NLS/13743 Zinc Finger/VP16 Fusion:: AtuORF23 3'UTR v1::AtUbi10 Promoter v2 (*Arabidopsis thaliana* Ubiquitin-10 Promoter::pat v5::AtuORF 1 3'UTR v4. The binary was constructed by cloning a DNA fragment containing the opaque-2 NLS/13743 Zinc FingerNP16 fusion into pDAB3912 via NcoI-SacI restriction sites. The resulting construct which was labeled as pDAB8218 contained the CsVMV Promoter v2::opaque-2 NLS/13743 Zinc Finger/ VP16 Fusion::AtuORF23 3'UTR v1 gene expression cassette. pDAB8218 was cloned into the pDAB4668 binary via an L-R Gateway Reaction (Invitrogen, Carlsbad, Calif.). This reaction produced pDAB4692 and was confirmed via restriction enzyme digestions and sequencing reactions.

Example 11

Analysis of Transformed Callus Samples

Transgenic *B. napus* callus lines were produced by the transformation of four ZFP TF constructs, pDAB4689-pDAB4692, and a control construct, pDAB8210, via *Agrobacterium*-mediated plant transformation as described in Example 3.2. The control construct, pDAB8210, was comprised of a pat gene expression cassette (AtUbi10 Promoter/pat/AtuORF1 3' UTR) and a non-target ZFN cassette (CsVMV Promoter/ZFN/AtuORF23 3' UTR). Total RNA was extracted and cDNA synthesized from all lines as described in Example 4.1. The only modification to the previously-described protocol was the use of Oligo dT primers for priming the cDNA reactions instead of random hexamers and the corresponding modification of the cDNA reaction, per manufacturer's specifications.

11.1 FatB4 and FatB5 mRNA Expression Analysis
11.1.1 FatB4 Quantitative Real-Time PCR (qRT-PCR) Assay for *B. napus*

A PCR mix was set up as follows for cDNA amplification of FatB4: 1.5 µL 10× Hot Start PCR Buffer (Qiagen, Valencia, USA), 1.2 µL of 10 mM dNTPs, 1 µL 25 mM MgCl$_2$, 0.15 µL Qiagen Hot Start Taq (5 U/µL), 0.5 µL zz143 FW primer of 10 µM stock (SEQ ID NO: 53: CTTTGAACGCTTATCTTC-CTC) (10 µM stock), 0.5 FATB5_R4 REV primer of 10 µM stock (SEQ ID NO: 54: TTCCACAACATCTCCCCAAG), 0.25 µL TaqMan MGB probe (Life Technologies, Carlsbad, Calif.) FatB4_MGB_Probe_4 of 5 µM stock (SEQ ID NO: 55: FAM-CTCAGGCTCCACCC), 1.5 µL of 10% (w/v) PVP-40), and H$_2$O to 13.5 µL per reaction. The appropriate quadrant(s) of a 384-well micro-plate were demarcated and filled with 13.5 µL of master mix per well. A sealing foil was then attached to the plate gently. The plate was centrifuged for 1 minute at 3,000 rpm in a Qiagen micro-plate centrifuge.

Next, 1.5 µL thawed, diluted first strand cDNAs were added to appropriate wells, followed by the addition of 1.5 µL plasmid cDNA standards from lowest to highest concentration of DNA into control wells. Finally, a sealing foil was firmly affixed to the plate and centrifuged. The PCR program was run in a LIGHTCYCLER® 480 Real-Time PCR System (Roche Diagnostics, Indianapolis, Ind., USA), using the following program: 1) activate 95° C. for 15 minutes; 2) denature 95° C. for 20-30 sec (@ 4.8° C./sec); 3) anneal 60° C. for 20-30 sec (@ 2.5° C./sec); 4) acquire 72° C. for 45-60 sec (@ 4.8° C./sec); repeat step 2)-4), 39-49 more times; 5) cool to 38° C. for 5 sec. to stop the reaction.

The FatB4 amplicon was 678 by in size. This sequence spans a 79 by intron based upon the genomic sequence. In addition, the reverse primer was designed to spans an intron thus favoring specific amplification of only FatB4 cDNAs, thereby eliminating amplification of the genomic DNA.

11.1.2 FatB5 qRT-PCR Assay for *B. napus*

A PCR mix was set up as follows for cDNA amplification of FatB5: 1.5 µL 10× Hot Start PCR Buffer (Qiagen, Valencia, USA), 1.2 µL of 10 mM dNTPs, 25 mM MgCl$_2$, 0.15 µL Qiagen Hot Start Taq (5 U/µl), 0.5 µL zz145 FW primer of 10 µM stock (SEQ ID NO: 56: CTTTGAAAGCTCATCTTC-CTC), 0.5 µL FATB5_R4 REV primer of 10 µM stock (SEQ ID NO; 57: TTCCACAACATCTCCCCAAG), 0.25 µL TaqMan MGB probe (Life technologies, Carlsbad, Calif.) FatB5_MGB_Probe_1 of 5 µM stock (SEQ ID NO: 58: FAM-AACCTTCATCCTCCCA), 1.5 µL of 10% (w/v) PVP-40), and H$_2$O to 13.5 µL per reaction. The remaining assay and the PCR cycle specifications were as described for FatB4 qRT-PCR assay in Example 11.1.1.

The amplicon produced was 678 by in size. This cDNA sequence spans a 76 by intron based upon the genomic sequence. In addition, the reverse primer was designed to span an intron thus favoring the cDNA amplification of FatB5, thereby eliminating amplification of the genomic DNA.

11.2 Tubulin mRNA Expression Analysis

This assay was completed as described in Example 4.3.

11.3 ZFP TF mRNA Expression Analysis

T$_0$ callus sample ZFP TF mRNA analysis was completed as per Example 4.4. The amplicon size in this assay was less than 1 Kb depending on the ZFP size in each of the designs. T$_0$ plant ZFP TF expression quantitation was performed with a VP16 activation domain-based assay as follows. A VP16 qRT-PCR mix was set up as follows for cDNA amplification of ZFP TF: 7.5 µL LIGHTCYCLER® 480 Probes Master 2× Buffer (Roche Diagnostics, Indianapolis, Ind., USA), 0.3 µL VP16_UPL_F1 primer of 10 µM stock (SEQ ID NO: 59: TCGATCTTGATATGTTGGGAGA), 0.3 µL VP16_UPL_R1 of 10 µM stock (SEQ ID NO: 60: AGGTG-CAGAATCATGTGGTG), 0.15 µL UPL Probe#85 (Roche Diagnostics, Indianapolis, Ind., USA), 1.5 µL of 10% (w/v) PVP-40), and H$_2$O to 13.65 µL. The appropriate quadrant(s) of a 384-well micro-plate were demarcated and filled with 13.5 µL of master mix per well. A sealing foil was then attached to the plate gently. The plate was centrifuged for 1 minute at 3000 rpm in a Qiagen micro-plate centrifuge. Thawed, diluted first strand cDNAs were added at 1.5 µL, followed by the addition of 1.5 µL plasmid cDNA standards from low to high concentrations into control wells. A sealing foil was firmly affixed to the plate and centrifuged. A PCR program was run in a LIGHTCYCLER® 480 Real-Time PCR System (Roche Diagnostics, Indianapolis, Ind., USA) using the following conditions: 1) activate 95° C. for 5 minutes; 2) denature 95° C. for 10 sec (@ 4.8° C./sec); 3) anneal/Extend 60° C. for 25 sec (@ 2.5° C./sec); 4) acquire 72° C. for 1 sec (@ 4.8° C./sec); 5) repeat step 2-4, 39-49 more times. Finally the reaction was cooled to 38° C. for 5 sec. to stop the reaction.

The VP16 amplicon size was 68 by this fragment size corresponds to the VP16 fragment which was expected to be produced by the PCR amplification.

11.4 Expression Analysis of Callus Samples

Figure 9:
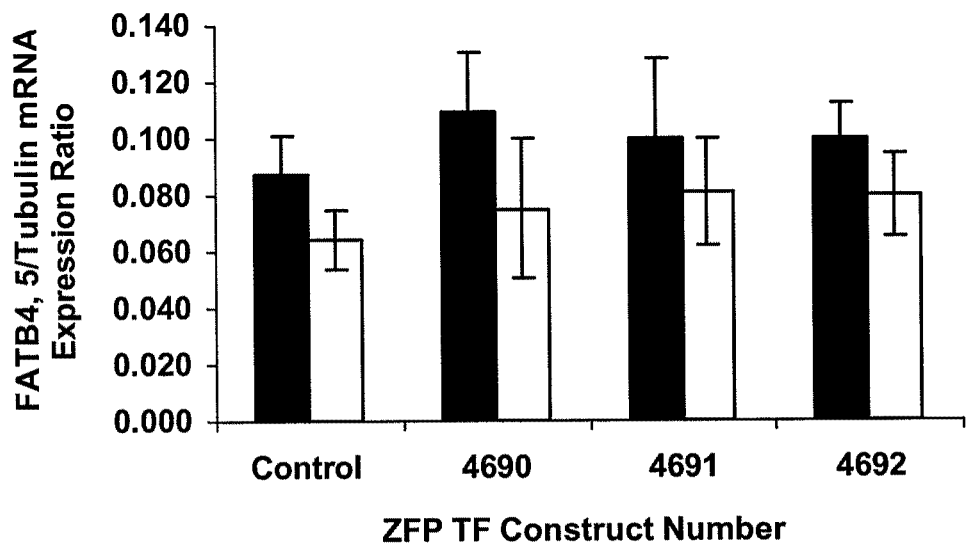
FIG. 9 depicts FatB4 and FatB5 gene expressions in *B. napus* callus lines transgenic for different ZFP TF designs present in constructs pDAB4690-pDAB4692. 17 lines for control and 25 lines for each of the ZFP constructs were analyzed. Black bars=FatB4 mRNA expression; gray bars=FatB5 mRNA expression.

Transgenic callus lines growing on HERBIACE® selection were analyzed for FatB4, FatB5, tubulin and ZFP TF expression levels by qRT-PCR. The tubulin gene served as a reference gene to normalize the expression of FatB4, FatB5 and ZFP TF mRNA levels. The FatB4/tubulin and FatB5/tubulin ratios were calculated to normalize mRNA expressions. Results showed statistically significant FatB4 mRNA and FatB5 mRNA up-regulation for construct designs pDAB4691 (p=0.005; FIG. 9). pDAB4692 callus lines showed an upregulation trend in FatB4 and FatB5 mRNA, but the trend was not statistically significant. pDAB4689 callus lines were also analyzed in a separate experiment, which showed an upregulation trend, but was not statistically significant (data not shown). Control cell lines did not amplify a ZFP TF specific amplicon, confirming that the ZFP TF assay was specific to the ZFP TF expressing lines only.

Example 12

Expression Analysis of Transgenic $T_0$ Plant Samples 12.1 Assay for *B. napus* Actin for Use as an Internal Control for qRT-PCR Total RNA was extracted and cDNA synthesized from all lines as described in Example 11. A PCR mix was set up as follows for cDNA amplification of actin (Bo Yang et al., 2007, Plant Science 173:156-171; actin gene Genbank accession no. AF111812): 7.5 μL LIGHTCYCLER® 480 SYBR Green I Master 2× Buffer, 0.34 BN_Actin_F primer of 10 μM stock (SEQ ID NO: 61: ACGAGCTACCTGACGGACAAG), 0.3 μL BN_Actin_R of 10 μM stock (SEQ ID NO: 62: GAGC-GACGGCTGGAAGAGTA), 1.5 μL of 10% (w/v) PVP-40), and q/s with $H_2O$ to 13.5 μL. The appropriate quadrant(s) of a 384-well micro-plate were demarcated and filled with 13.5 μL of master mix per well. A sealing foil was then attached to the plate gently. The plate was centrifuged for 1 minute at 3000 rpm in a Qiagen micro-plate centrifuge. Thawed, diluted first strand cDNAs were added at 1.5 μL, followed by the addition of 1.5 μL cDNA standards from low to high concentrations in control wells. A sealing foil was firmly affixed to the plate and centrifuged. A PCR program was run in a LIGHTCYCLER® 480 Real-Time PCR System (Roche Diagnostics, Indianapolis, Ind., USA) using the following conditions: 1) activate 95° C. for 10 minutes; 2) denature 95° C. for 10 sec (@ 4.8° C./sec); 3) anneal/Extend 60° C. for 20 sec (@ 2.5° C./sec); 4) acquire 72° C. for 20 sec (@ 4.8° C./sec); 5) repeat step 2-4, 39-49 more times. Finally the reaction was cooled to 38° C. for 5 sec. to stop the reaction. The amplicon produced was 80 by in size.

12.2 FatB4 and FatB5 mRNA Expression Analysis

*B. napus* plants that had been transformed with pDAB4689-pDAB4691 were assayed for increased mRNA expression of FatB4 and FatB5. In addition, two types of controls were used. A non-transgenic control consisting of Nex710 plants served as a negative control. A second transgenic control of *B. napus* Nex710 plants which had been transformed with pDAB8210 was also analyzed. The pDAB8210 construct design consisted of two gene expression cassettes. The pat gene expression cassette (AtUbi10 promoter::pat gene::AtuORF 1 3' UTR) and a non-target Zinc Finger Nuclease (ZFN) gene expression cassette (AtUbi10 promoter::ZFN gene::AtuORF23 3' UTR). The ZFN expressed in pDAB8210 was not expected to bind and cleave the genome of *B. napus* Nex710 plants and should not alter the phenotype of these plants.

Putative transgenic calli growing on HERBIACE® selection were regenerated into plants (Example 3.3). Leaf samples were collected from the 6-leaf stage *B. napus* plants growing in the greenhouse for mRNA expression analysis. Six leaf punches from each plant were isolated and placed on ice prior to RNA extraction. Total RNA was extracted using the QIAGEN RNEASY kit. cDNA synthesis and subsequent dilutions were completed as described in Example 11. The expression analysis protocol for FatB4 and FatB5 via qRT-PCR is described above. ZFP TF expression analysis was plus/minus with the assay. The actin reference gene qRT-PCR assay is described above.

Figure 10:
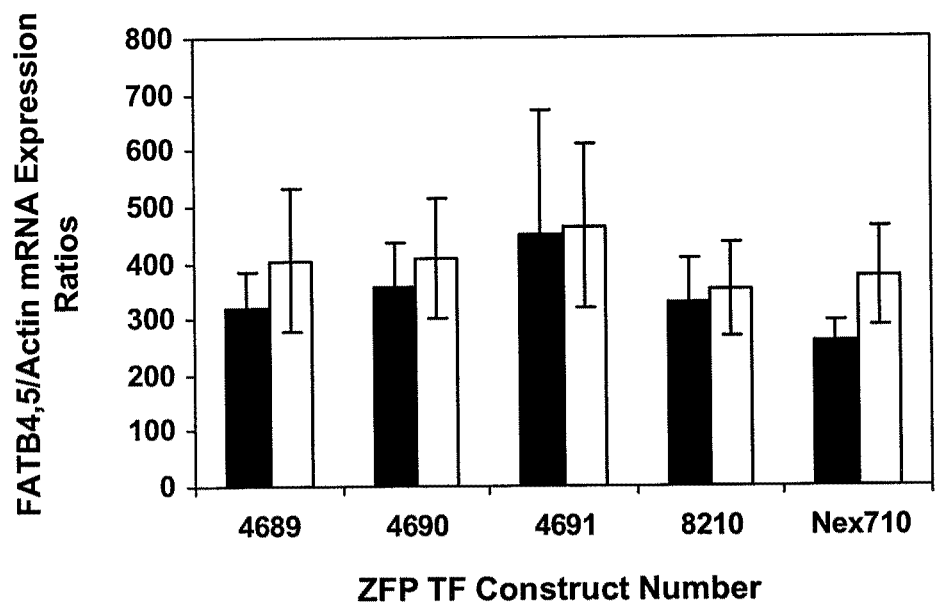
FIG. 10 shows FatB4 and FatB5 expressions in *B. napus* T0 transgenic plant leves analyzed with qRT-PCR. Three constructs comprising ZFP TFs, pDAB4689-pDAB4691 were tested in transgenic plants. Total number of independent T0 transgenic plants analyzed for this experiment was 40, 62, 41, and 22 for pDAB 4689-pDAB4691 and pDAB8210 respectively. Nex710 control was comprised of 10 plants. Ninety-seven percent of the transgenic events for 3 ZFP TF constructs were positive for ZFP TF expression, as determined by the ZFP TF expression assay (Example 8.3). Similar results were obtained when native tubulin mRNA expression was used as a reference to normalize FatB gene expressions. Black bar=FatB4 expression; gray bar=FatB5 expression.

$T_0$ leaf expression for FatB4 and FatB5 genes varied between constructs (FIG. 10). The highest FatB4 and FatB5 mRNA up-regulation was observed in pDAB4691 transgenic plant events which resulted in an overall 2.0-2.5 fold increases in mRNA expressions as compared to Nex710 non-transgenic and pDAB8210 transgenic controls. Expression of both genes was statistically significant (below p=0.05) as compared to controls. Therefore, further characterization of the constructs was continued with pDAB4691.

Example 13

Analysis of Transgenic $T_1$ Plants 13.1 Fatty Acid Analysis of $T_1$ Seed

A significant difference in C18:0 content between "Low" and "High" oil seed of event pDAB4691-003-049.1 ("event 49") was observed (Table 12). The C18:0 content of the "Low" category seed was similar to that of the Nex710 (non-transgenic control) and pDAB8210 (transgenic control) lines. The C18:0 content in the "High" seed correlated with ZFP TF expression which resulted in FatB gene(s) up-regulation. Some increases in C20:0, C22:0 and C24:0 were also observed based on the flow of C18:0 into longer chain fatty acids. C16:0 content in individual seed did not appear to change within either of the "Low" or "High" categories. This result is indicative of the fact that pDAB4691 ZFP TF binds and up-regulates the FatB gene(s) specific for C18:0-ACP to C18:0 enzymatic reactions rather than the C16:0-ACP to C16:0 reactions (see Example 1, FIG. 1).

TABLE 12

Fatty Acid profile of individual $T_1$ seed measured with FAME analysis

| Samples* | Total Sats | C16:0 | C16:1 | C18:0 | C20:0 | C22:0 | C24:0 |
|---|---|---|---|---|---|---|---|
| Event 49 Low | 6.35 | 4.11 | 0.48 | 1.45 | 0.46 | 0.21 | 0.07 |
| Event 49 Low | 6.35 | 3.70 | 0.35 | 1.62 | 0.58 | 0.30 | 0.12 |

TABLE 12-continued

Fatty Acid profile of individual $T_1$ seed measured with FAME analysis

| Samples* | Total Sats | C16:0 | C16:1 | C18:0 | C20:0 | C22:0 | C24:0 |
|---|---|---|---|---|---|---|---|
| Event 49 Low | 6.49 | 3.64 | 0.36 | 1.66 | 0.62 | 0.32 | 0.18 |
| Event 49 High | 7.50 | 3.55 | 0.42 | 2.59 | 0.80 | 0.34 | 0.17 |
| Event 49 High | 7.74 | 3.63 | 0.45 | 2.59 | 0.88 | 0.38 | 0.22 |
| Event 49 High | 7.93 | 3.67 | 0.47 | 2.82 | 0.86 | 0.38 | 0.17 |
| Event 49 Mean (n = 24) | 6.90 | 3.70 | 0.40 | 2.03 | 0.67 | 0.31 | 0.15 |
| Event 49 Std Dev (n = 24) | 0.51 | 0.14 | 0.05 | 0.37 | 0.10 | 0.04 | 0.03 |
| Nex710 Mean (n = 24) | 6.47 | 3.70 | 0.45 | 1.79 | 0.57 | 0.26 | 0.11 |
| Nex710 Std Dev (n = 24) | 0.35 | 0.24 | 0.06 | 0.17 | 0.06 | 0.04 | 0.03 |
| 8210 Mean (n = 150) | 6.27 | 3.51 | 0.34 | 1.63 | 0.61 | 0.33 | 0.14 |
| 8210 Std Dev (n = 150) | 0.40 | 0.24 | 0.07 | 0.25 | 0.08 | 0.05 | 0.04 |

*Fatty acid analysis was performed on 24 individual $T_1$ seed of event 49 and Nex710, and 144 seed of pDAB8210 comprised of 6 events. "Low" and "High" categories represent specific FA content of the individual seed when sorted based on C18:0 content.

13.2 ZFP TF Presence Analysis in $T_1$ Plants

One-hundred $T_1$ seeds of event 49 were planted in the greenhouse. Ninety-seven plants germinated into seedlings. ZFP TF copy number was estimated using a pat qRT-PCR assay as described in Example 6.2 for plant material isolated from the 2-4 leaf stage. Event 49 contained multiple insertions (~3 insertions) and 0-7 pat gene, and hence ZFP TF, copies segregated into the $T_1$ population. Only one null plant was identified from the $T_1$ population.

13.3 FatB4 and FatB5 mRNA Up-Regulation in $T_1$ Plants

Native FatB gene expression analysis was performed on all 97 plants of the segregating $T_1$ population. Non-transgenic Nex710 plants which were planted at the same time were included in the study as controls. Six-leaf punches per plant were harvested and placed on ice until RNA extraction could be completed. Total RNA was extracted using the QIAGEN RNEASY kit. cDNA synthesis and subsequent dilutions were completed as described in Example 11. Expression analysis of FatB4, FatB5, tubulin and VP16 (ZFP TF) was performed as described above.

Figure 11:
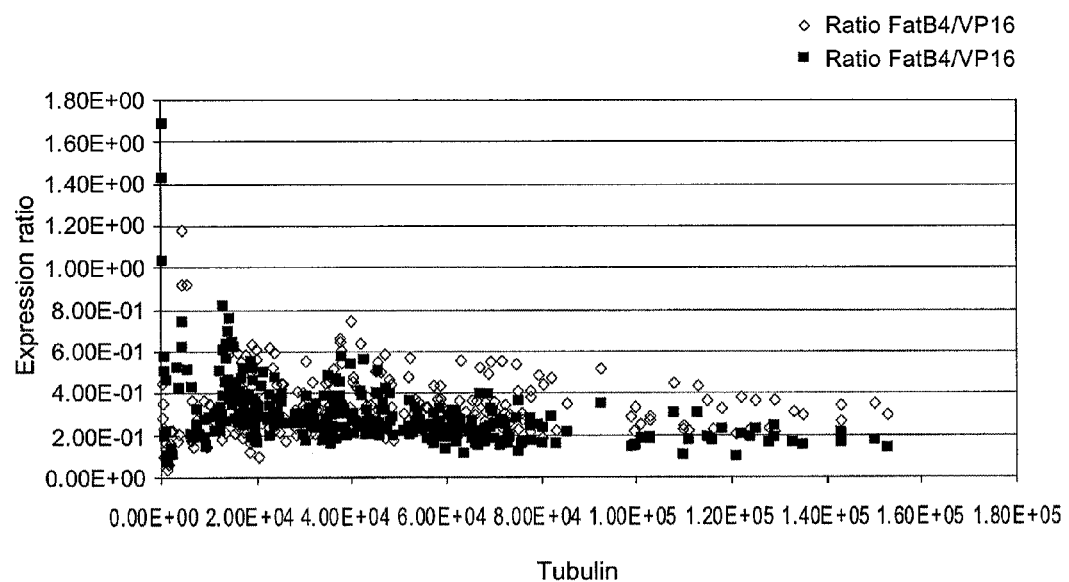
FIG. 11 is a plot displaying a linear relationship between FatB genes and Tubulin expression when analyzed from T1 plants. Black squares=FatB4 expression; gray diamonds=FatB5 expression.

Statistical analysis of the ratios of FatB4/FatB5 and tubulin showed significant linear trends with tubulin expression (FIG. 11) indicating that increases in FatB4/FatB5 did not have a 1:1 relationship with increases in the endogenous control, tubulin. As such, the ratios were not used in this analysis, and tubulin was included as a covariable in models of the expression of FatB4/FatB5. To remove any co-linearity between tubulin and VP16 (ZFP TF), the incidence matrices for the model equations were orthagonalized.

The following model was fit to all datasets in the current study: where status; is the transgenic status of $y_{ijk}$ (transgenic or null/control);

$$y_{ijk} = status_i + transgenic*VP16 + e_{ijk}$$

transgenic*VP16 is a linear regression on VP16 nested within transgenic lines; and $e_{ijk}$ is the random residual. Given that there were three repeated measurements for each sample, a correlated residual structure was used:

$$R = \sigma_e^2 \left( I_n \otimes \begin{bmatrix} 1 & \phi & \phi \\ \phi & 1 & \phi \\ \phi & \phi & 1 \end{bmatrix} \right)$$

where $I_n$ is the identity matrix with rank equal to the number of samples and $\phi$ is the correlation between residuals of repeated measures.

Figure 12:
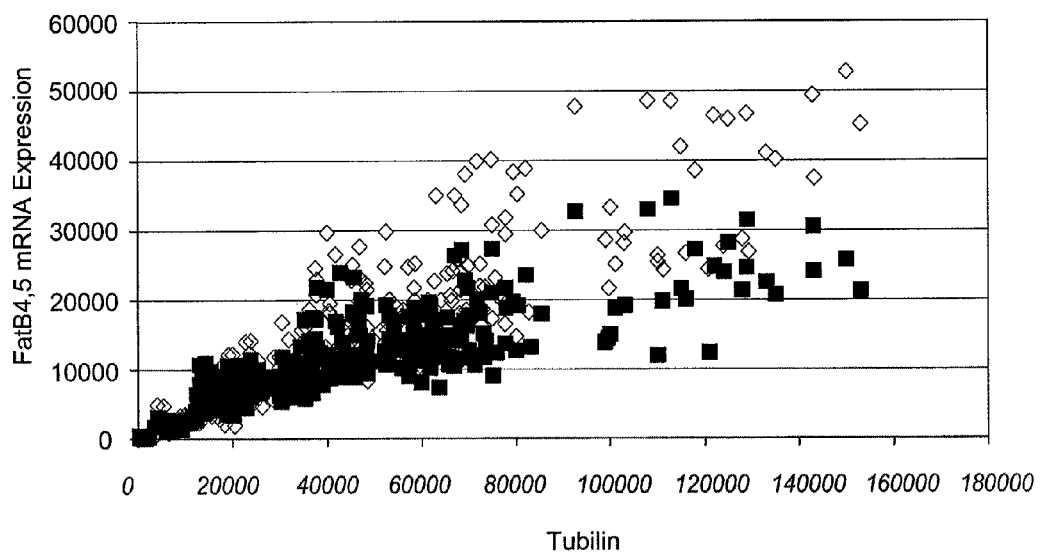
FIG. 12 shows qRT-PCR for FatB4 and FatB5 expression in T1 plant leaves transgenic for ZFP TF construct pDAB4691. Black squares=FatB4 expression; gray diamonds=FatB5 expression.

Results of analysis for event 49 detected significant up-regulation in FatB4 with nested regressions of FatB4 expression on VP16 showing highly significant positive slopes (FIG. 12, Table 13). For FatB5, nested regressions showed positive slopes for up-regulation, and the slope was statistically significant. For the up-regulation events it should be noted that the transformed and control plants were not from the same line so there could be some confounding of the line and transformation effects.

TABLE 13

Results for up-regulation events

| Event | Gene | Effect[A] | Solution | P-Value |
|---|---|---|---|---|
| 4691-3-049.001 | FatB4 | Transformed-control | 10331.11 | <0.00001 |
| | | Transformed*VP16 | 0.764E−05 | <0.00001 |
| | FatB5 | Transformed-control | 5084.09 | <0.00001 |
| | | Transformed*VP16 | 0.308E−05 | <0.00001 |

[A]Transformed-control = the difference in least square mean expression between transformed lines and lines not carrying transgenes. Transformed*VP16 = regression of FatB4/FatB5 expression on VP16 expression nested within transgenic lines.

Event 49 $T_1$ plants were then sorted based on the FatB4/tubulin and then FatB5/tubulin expression ratios to find the highest expressing plants for advancement to $T_2$ generation in the greenhouse. Eight of the highest expressing FatB4 plants were selected for advancement to maturity. Six of these plants were also the highest expressing for FatB5. The ZFP TF copy number in these highest expressing plants varied from 2-4 copies while the copy number that segregated in the entire $T_1$ progeny were 0-7 copies. For control plants, one null plant of event 49 and ten Nex710 control plants were also advanced to maturity for $T_2$ seed collection.

13.4 Fatty Acid Analysis of $T_2$ Seed

Figure 13:
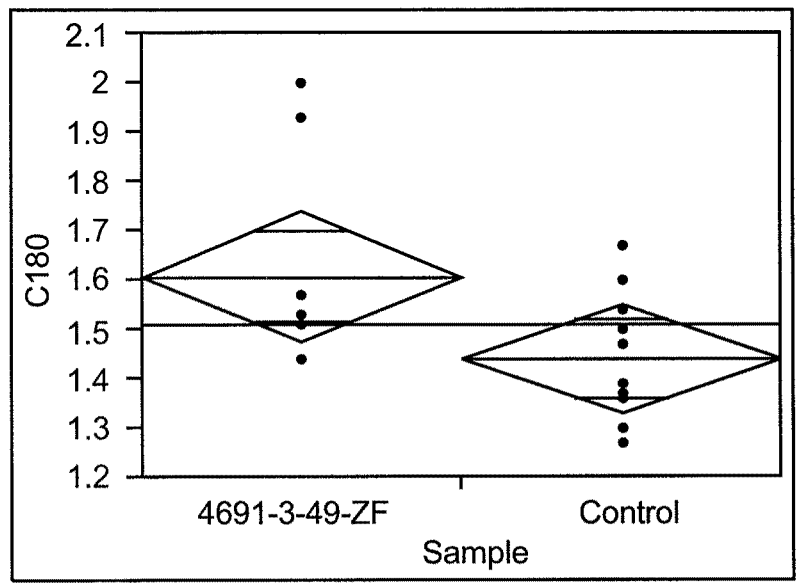
FIG. 13 is a one way analysis of C18:0 content by sample using JMP statistical software.

Fatty acid (FA) analysis was performed on a 24 seed bulk of all plants as described in Example 6.1. The FA profile of one null plant was combined with ten Nex710 control plants for control FA profile calculations. On average, a 12% increase in the C18:0 content was observed for event 49 compared to that of Nex710 (Tables 14A and 14B). This increase was statistically significant at p=0.05 (FIG. 13). The long chain FAs, such as C20:0, C22:0 and C24:0, also showed some increases leading to increase in the total saturated FA content by 5%. Since FatB enzyme catalyzes the conversion of C18:0 ACP into C18:0 free FA, more C18:0 will be accumulated as a result of FatB4 and FatB5 transcriptional up-regulation (FIG. 1). The pDAB4691 (Example 6, Tables 1 and 2), is specific to both FatB4 and FatB5 genes, which resulted in a significant change in the FA profile (Tables 14A and 14B).

TABLE 14A

Fatty acid profile (C16:0, C16:1, C18:0, C18:1, C18:2 and C18:3) of event 49 transgenic and Nex710 control samples

| S.N. | Plant ID | Total Sats | C16:0 | C16:1 | C18:0 | C18:1 | C18:2 | C18:3 |
|---|---|---|---|---|---|---|---|---|
| 1 | 4691-3-049 (8) | 6.42 | 3.47 | 0.24 | 1.61 | 76.32 | 11.20 | 3.52 |
| 2 | Nexera710 (11) | 6.11 | 3.40 | 0.23 | 1.44 | 76.26 | 11.25 | 3.76 |

Numbers in brackets in column 2 represent number of plants analyzed.

TABLE 14B

Fatty acid (C20:0, C20:1, C20:2, C22:0, C22:1, C24:0, C24:1) profile of event 49 transgenic and Nex710 control samples

| S.N. | Plant ID | Total Sats | C20:0 | C20:1 | C20:2 | C22:0 | C22:1 | C24:0 | C24:1 |
|---|---|---|---|---|---|---|---|---|---|
| 1 | 4691-3-049 (8) | 6.42 | 0.66 | 1.39 | 0.05 | 0.43 | 0.02 | 0.21 | 0.18 |
| 2 | Nexera710 (11) | 6.11 | 0.61 | 1.43 | 0.06 | 0.41 | 0.02 | 0.20 | 0.17 |

Numbers in brackets in column 2 represent number of plants analyzed.

No significant changes in total C16 content was observed with native FatB4 and FatB5 gene up-regulation. It is likely that catalysis of C16:0-ACP to C16:0 occurs with other FatB genes but not with FatB4 and FatB5, the exemplified targets for up-regulation using the pDAB4691 ZFP TF design (FIG. 1).

Individual seed C16:0 content did not appear to change in T1 seed "Low" and "High" categories (Table 12), indicative of the fact that pDAB4691 ZFP TF design more specifically binds to the FatB gene(s) for C18:0-ACP to C18:0 enzymatic reaction rather than C16:0-ACP to C16:0 reaction (FIG. 1).

Figure 14:
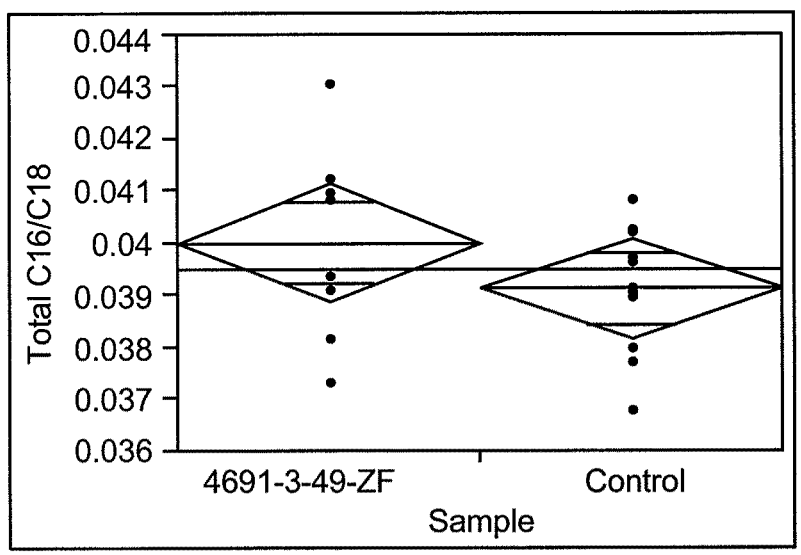
FIG. 14 shows a one way analysis of total C16/C18 content by sample using JMP statistical analysis software.

It should be noted that up-regulation of the native β-ketoacyl-ACP synthetase II genes (Examples 1-6) induced by ZFP TF brought about different changes in the FA profile as compared to the native FatB4 and FatB5 gene up-regulations. For example, β-ketoacyl-ACP synthetase II gene up-regulation caused statistically significant reduction in C16:0 and C16:1 contents and concomitant increase in total C18 content as compared to their null segregants (Example 6, FIG. 6, Tables 5 and 8). Comparatively, ZFP-TF-mediated FatB gene up-regulation caused statistically significant increases in the C18:0 content but no apparent change in the C16:0 content (FIG. 14). Again these changes in the FA profiles through ZFP TF-mediated up-regulation of the β-ketoacyl-ACP synthetase II and FatB genes concur as per the FA biosynthesis pathway (FIG. 1).

Example 14

ZFP TF Constructs Design for Plant Transformation

Four constructs were designed and built for transcriptional down-regulation of the FatB genes in *B. napus* L (Table 15). The best FatB up-regulation ZFP designs, 13722 and 13714, were employed for demonstration of FatB down-regulation (Examples 9-13). These ZFP designs were fused to an opaque-2 nuclear localization signal and a repression domain consisting of either KRAB1 (Hanna-Rose and Hansen, 1996, *Trends in Genetics*, 12:229-234) or NtERF3 (Ohta et al., *The Plant Cell*, 2001, 13:1959-1968), to construct functional ZFP TFs. All of the ZFP TFs were expressed under seed-specific promoters; either the *Arabidopsis thaliana* Lipid Transfer Protein 2 Promoter (AtLTP170 Promoter) (Genbank ID: NC 003076) or the *Phaseolus vulgaris* 13-Phaseolin Promoter (PvPhas Promoter) (U.S. Pat. No. 5,591,605) were used.

TABLE 15

ZFP TF construct details for targeted down-regulation of FatB genes

| S.N. | ZFP design | Construct No. | Gene Cassettes |
|---|---|---|---|
| 1 | 13722 | pDAS5203 | AtLTP170/Op-2* NLS-ZFP-13722-KRAB1/ORF23 3' UTR//AtUbi10/Pat/AtuORF1 3' UTR |
| 2 | 13714 | pDAS5204 | AtLTP170/Op-2 NLS-ZFP-13714-KRAB1/ORF23 3' UTR//AtUbi10/Pat/AtuORF1 3' UTR |
| 3 | 13722 | pDAS5212 | PvPhas/Op-2-NLS-ZFP13722-KRAB1/Phas 3' UTR//AtUbi10/Pat/AtuORF1 3' UTR |
| 4 | 13722 | pDAS5227 | AtLTP170/Op-2 NLS-ZFP-13722-NtERF3/ORF23 3' UTR//AtUbi10/Pat/AtuORF1 3' UTR |

*Op-2 = Opaque-2 Nuclear Localization Signal pDAS5203 is a binary plasmid which contained the opaque-2 NLS/13722/KRAB1 and pat gene expression cassettes. This construct includes the following gene elements; AtLTP Promoter 170::opaque-2 NLS/13722 Zinc Finger/KRAB1 Fusion::AtuORF23 3'UTR v1::AtUbi10 Promoter v2::pat v5::AtuORF1 3'UTR v4. The binary was constructed by cloning a DNA fragment containing the opaque-2 NLS/13722 Zinc Finger/KRAB1 fusion into a Gateway donor vector. The resulting construct contained the AtLTP Promoter 170::opaque-2 NLS/13722 Zinc Finger/KRAB1 Fusion::AtuORF23 3'UTR v1 gene expression cassette. This construct was cloned into a binary via an L-R Gateway Reaction (Invitrogen, Carlsbad, Calif.). This reaction produced pDAS5203 and was, confirmed via restriction enzyme digestions and sequencing reactions.

pDAS5204 is a binary plasmid which contained the opaque-2 NLS/13714/KRAB1 and pat gene expression cassettes. This construct includes the following gene elements; AtLTP Promoter 170::opaque-2 NLS/13714 Zinc Finger/KRAB1 Fusion::AtuORF23 3'UTR v1::AtUbi10 Promoter v2::pat v5::AtuORF1 3'UTR v4. The binary was constructed by cloning a DNA fragment containing the opaque-2 NLS/13714 Zinc Finger/KRAB1 fusion into a Gateway donor vector. The resulting construct contained the AtLTP Promoter 170::opaque-2 NLS/13714 Zinc Finger/KRAB1 Fusion::AtuORF23 3'UTR v1 gene expression cassette. This construct was cloned into a binary via an L-R Gateway Reaction (Invitrogen, Carlsbad, Calif.). This reaction produced pDAS5204 and was confirmed via restriction enzyme digestions and sequencing reactions.

pDAS5212 is a binary plasmid which contains the opaque-2 NLS/13722/KRAB1 and pat gene expression cassettes. This construct includes the following gene elements; PvPhas Promoter::opaque-2 NLS/13722 Zinc Finger/KRAB1 Fusion::AtuORF23 v1::AtUbi10 Promoter v2::pat v5::AtuORF1 3'UTR v4. The binary was constructed by cloning a DNA fragment containing the opaque-2 NLS/13722 Zinc Finger/KRAB1 fusion into a Gateway donor vector. The resulting construct contained the PvPhas Promoter::opaque-2 NLS/13722 Zinc Finger/KRAB1 Fusion::AtuORF23 3'UTR v1 gene expression cassette. This construct was cloned into a binary via an L-R Gateway Reaction (Invitrogen, Carlsbad, Calif.). This reaction produced pDAS5212 and was confirmed via restriction enzyme digestions and sequencing reactions.

pDAS5227 is a binary plasmid which contains the opaque-2 NLS/13722/NtERF3 and pat gene expression cassettes. This construct includes the following gene elements; RB7 MAR v3 AtLTP Promoter 170::opaque-2 NLS/13722 Zinc Finger/NtERF3 Fusion::AtuORF23 3'UTR v1:: AtUbi10 Promoter v2::pat v5::AtuORF1 3'UTR v4. The binary was constructed by cloning a DNA fragment containing the opaque-2 NLS/13722 Zinc Finger/NtERF3 fusion into a Gateway donor vector. The resulting construct contained the AtLTP Promoter 170::opaque-2 NLS/13722 Zinc Finger/NtERF3 Fusion::AtuORF23 3'UTR v1 gene expression cassette. This construct was cloned into a binary via an L-R Gateway Reaction (Invitrogen, Carlsbad, Calif.). This reaction produced pDAS5227 and was confirmed via restriction enzyme digestions and sequencing reactions.

The constructs were stably transformed into *B. napus* variety Nex710 by *Agrobacterium*-mediated transformation of hypocotyl explants (Example 3.2-3.3). $T_0$ plants growing in the greenhouse were self pollinated and $T_1$ seed collected four months after transplanting.

Example 15

Analysis of T1 Seed Transgenic for 4 ZFP TF Constructs $T_1$ seeds were obtained from transgenic events (lines) 8, 20, 37 and 15 of constructs pDAS5203, pDAS5204, pDAS5212 and pDAS5227, respectively. Five Nex710 plant seed were used as controls. FA analysis was performed on 24 individual seeds of each of the $T_1$ transgenic event, as described earlier in Example 6.1, to first identify the ZFP TF construct that most effectively alters the FA profile.

15.1 Fatty Acid (FA) Analysis of T1 Seed

Constructs pDAS5203, pDAS5212 and pDAS5227 produced transgenic events with the lowest total saturated FA profiles in comparison to control Nex710 (Table 16). Pair wise differences between each of the two construct events, pDAS5203 and pDAS5212, and Nex710 control were significant (p=<0.005). However the pair wise difference of pDAS5227 exhibited a strong trend (p=0.06). One of the events from pDAS5203 contained the lowest total saturated FA content of 5.3% (not shown) compared to an average of 6.38% in the Nex710 control. This is a 17% reduction in total saturated FAs.

TABLE 16A

T1 seed FA profile of multiple construct transgenic events

| Construct No. | Type of Analysis | Total Sats | C14:0 | C16:0 | C16:1 | C18:0 | C18:1 | C18:2 | C18:3 |
|---|---|---|---|---|---|---|---|---|---|
| pDAS5212 | Mean (n = 37)* | 6.00 | 0.05 | 3.60 | 0.24 | 1.38 | 75.88 | 12.24 | 3.41 |
| pDAS5212 | Std Dev (n = 37) | 0.21 | 0.01 | 0.20 | 0.02 | 0.14 | 1.36 | 1.03 | 0.41 |
| pDAS5212 | p value** | 0.01 | 0.07 | 0.89 | 0.47 | <0.0001 | 0.39 | 0.37 | 0.94 |
| pDAS5204 | Average (n = 20) | 6.26 | 0.05 | 3.52 | 0.25 | 1.65 | 76.33 | 11.52 | 3.58 |
| pDAS5204 | Std Dev (n = 20) | 0.29 | 0.01 | 0.15 | 0.02 | 0.16 | 0.78 | 0.66 | 0.30 |
| pDAS5204 | p value | 0.43 | 0.72 | 0.52 | 0.69 | 0.32 | 0.16 | 0.04 | 0.34 |
| pDAS5203 | Average (n = 8) | 5.98 | 0.05 | 3.68 | 0.26 | 1.33 | 75.32 | 12.74 | 3.55 |
| pDAS5203 | Std Dev (n = 8) | 0.36 | 0.01 | 0.25 | 0.05 | 0.13 | 1.76 | 1.31 | 0.47 |
| pDAS5203 | p value | 0.02 | 0.06 | 0.45 | 0.96 | 0.0001 | 0.96 | 0.98 | 0.49 |
| pDAS5227 | Average (n = 15) | 6.09 | 0.03 | 3.63 | 0.32 | 1.32 | 75.43 | 12.32 | 3.73 |
| pDAS5227 | Std Dev (n = 15) | 0.35 | 0.00 | 0.29 | 0.09 | 0.12 | 1.69 | 1.36 | 0.37 |
| pDAS5227 | p value | 0.07 | 0.002 | 0.69 | 0.012 | <0.0001 | 0.84 | 0.48 | 0.1 |
| Nex710 | Average (n = 5) | 6.38 | 0.04 | 3.59 | 0.26 | 1.73 | 75.28 | 12.76 | 3.40 |
| Nex710 | Std Dev (n = 5) | 0.61 | 0.01 | 0.15 | 0.03 | 0.49 | 3.00 | 2.76 | 0.43 |

*Numbers in brackets show the number of events included in analysis.
**p value of equal or less than 0.05 was considered statistically significant and was calculated with JMP software.

TABLE 16B

T1 seed FA profile of multiple construct transgenic events

| Construct No. | Type of Analysis | Total Sats | C20:0 | C20:1 | C20:2 | C22:0 | C24:0 | C24:1 |
|---|---|---|---|---|---|---|---|---|
| pDAS5212 | Mean (n = 37)* | 6.00 | 0.54 | 1.33 | 0.06 | 0.30 | 0.13 | 0.08 |
| pDAS5212 | Std Dev (n = 37) | 0.21 | 0.04 | 0.11 | 0.01 | 0.03 | 0.05 | 0.04 |
| pDAS5212 | p value** | 0.01 | 0.03 | 0.003 | 0.14 | 0.76 | 0.26 | 0.23 |
| pDAS5204 | Average (n = 20) | 6.26 | 0.59 | 1.20 | 0.05 | 0.32 | 0.13 | 0.11 |
| pDAS5204 | Std Dev (n = 20) | 0.29 | 0.06 | 0.17 | 0.01 | 0.05 | 0.05 | 0.03 |
| pDAS5204 | p value | 0.43 | 0.79 | 0.20 | 0.87 | 0.68 | 0.29 | 0.63 |
| pDAS5203 | Average (n = 8) | 5.98 | 0.51 | 1.28 | 0.05 | 0.29 | 0.12 | 0.11 |
| pDAS5203 | Std Dev (n = 8) | 0.36 | 0.03 | 0.15 | 0.01 | 0.02 | 0.01 | 0.05 |
| pDAS5203 | p value | 0.02 | 0.006 | 0.048 | 0.42 | 0.56 | 0.55 | 0.84 |
| pDAS5227 | Average (n = 15) | 6.09 | 0.56 | 1.39 | 0.06 | 0.39 | 0.15 | 0.16 |
| pDAS5227 | Std Dev (n = 15) | 0.35 | 0.07 | 0.23 | 0.01 | 0.10 | 0.08 | 0.05 |
| pDAS5227 | p value | 0.07 | 0.21 | 0.0005 | 0.066 | 0.008 | 0.081 | 0.004 |
| Nex710 | Average (n = 5) | 6.38 | 0.60 | 1.10 | 0.05 | 0.31 | 0.11 | 0.10 |
| Nex710 | Std Dev (n = 5) | 0.61 | 0.13 | 0.09 | 0.01 | 0.07 | 0.05 | 0.08 |

*Numbers in brackets show the number of events included in analysis.
**p value of equal or less than 0.05 was considered statistically significant and was calculated with JMP software.

Figure 15:
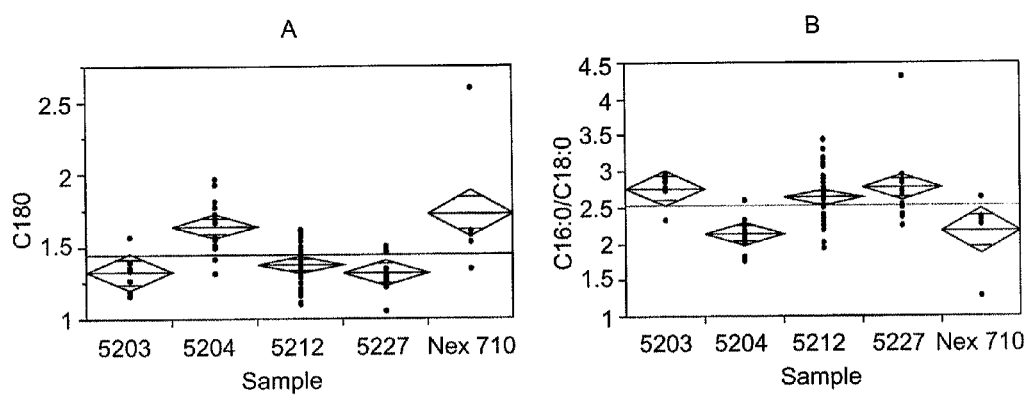
FIG. 15 depicts an analysis of T1 FA profiles of mature seed comprising 4 ZFP TF construct events is shown with JMP statistical software. A and B panels represent one way analysis by sample (construct) of C18:0 content and C16:0/C18:0 content respectively.

The specific FAs profiles of events pDAS5203, pDAS5212 and pDAS5227 resulted in a 21-25% reduction in C18:0 as compared to Nex710 (FIG. 15A). All of these differences were statistically significant at or below p=0.001 (Table 16). Other long chain FAs, C20:0, C22:0 and C24:0 also showed declines in concentration. However, no changes in C16:0 content was observed resulting in a significant increase in C16:0/C18:0 content in all three construct transgenic events (FIG. 165B).

Figure 16:
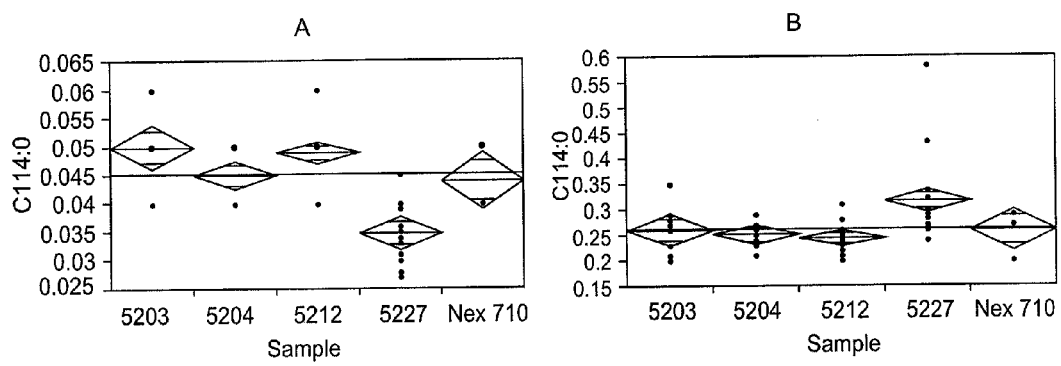
FIG. 16 depicts an analysis of T1 FA profiles of mature seed comprising 4 ZFP TF construct events is shown with JMP statistical software. A and B panels display one way analysis by sample (construct) of C14:0 and C16:1 content respectively, highlighting the differentiating attribute of construct pDAS5227. Analysis of T1 FA profiles of mature seed comprising 4 ZFP TF construct events is shown with JMP statistical software. A and B panels display one way analysis by sample (construct) of C14:0 and C16:1 content respectively, highlighting the differentiating attribute of construct pDAS5227.

FA profile of pDAS5227 transgenic seed showed a distinct difference as compared to pDAS5203 and pDAS5212. A 23% reduction in C14:0 (p=0.002) and a 19% increase in C16:1 (p=0.01) contents were observed in pDAS5227 seed as compared to Nex710 (FIGS. 16A & B, Table 16). The pDAS5227 ZFP TF design is identical to that of pDAS5203 and pDAS5212 except for the presence of an ERF3 down-regulation domain fused to ZFP instead of a KRAB 1 domain (Table 15).

A different ZFP design, 13714, present in pDAS5204 was not as effective in C18:0 reduction compared to the 13722 design (Table 16). Unlike the 13722 design which binds to both the FatB4 and FatB5 genes, the 13714 design binds only to the FatB5 gene (Example 9, Table 10B).

15.2 Identification of Plants for mRNA Analysis

Two transgenic events, 5212[1]-004 and 5227[4]-012, which were produced by transformation with constructs pDAS5212 and pDAS5227, respectively, were selected for FatB5 transcriptional down-regulation analysis. Fifty to one-hundred $T_1$ seed were planted in the greenhouse and plants were grown. Four leaf punches were collected from plants at the 2-3 leaf stage. This plant material was analyzed for ZFP TF copy number using a pat qRT-PCR assay (Example 6.2). Random ZFP null and ZFP positive plants were then selected for advancement to maturity to collect $T_2$ seed (Table 17). Immature pods from the same plants were collected 25 days after flowering (DAF) for FatB mRNA analysis. Both events segregated as a single copy. These events were labeled as 5212-4 and 5227-12.

TABLE 17

Transgenic event screening for identification of ZFP positive and null plants

| Event Name | T1 Seed/plant | Plant No. | Copy No. | #Plants to T2 |
|---|---|---|---|---|
| 5212-004 | Seed planted | 50 | | |
| | Seed germinated | 49 | | |
| | Screening for pat copy number | 17 | Null | 5 |
| | | 26 | 1 copy | 3 |
| | | 5 | 2 copy | 4 |
| | | 1 | NT* | |
| | ChiTest | 0.04 | | |
| 5227-12 | Seed planted | 100 | | |
| | Seed germinated | 96 | | |
| | Screening for pat copy number | 19 | Null | 4 |
| | | 32 | 1 copy | 3 |
| | | 27 | 2 copy | 4 |
| | | 18 | NT* | |
| | ChiTest | 0.034 | | |

*NT = Not tested.

15.3 RNA Extraction and qRT-PCR Assay Development

RNA was isolated from immature *Brassica* seed with the plant RNAEASY® kit obtained from Qiagen (Valencia, Calif.). Seeds were placed in cluster tubes containing RLT buffer (Qiagen)/β-mercaptoethanol (BME) and a stainless steel bead. Samples were put into a cluster tube rack and homogenized at 500 strokes per min for 5 minutes in a bead mill (Kleco, Visalia, Calif.). The tube rack was turned 180 degrees and homogenized for an additional 5 minutes. Samples were then transferred to 1.5 ml Eppendorf tubes and centrifuged for 5 minutes at 20,000×g and the supernatant was transferred to a fresh tube. RNA was isolated as describe by the manufacturers protocol (Qiagen; Valencia, Calif.). RNA was eluted from the columns with 50 uL of RNase free water and the RNA samples were quantified with a Nanoprop 8000 by Thermo Scientific (Wilmington, Del.).

Ten to twenty micrograms of the RNA was treated with TURBO DNA-free (catalog number AM1907; Applied Biosystems, Foster City, Calif.) DNase in 1.5 ml RNase/DNase free tubes to remove genomic DNA. For each RNA sample a fifty microliter reaction was prepared containing RNA, 1× DNase buffer, and 2 units of TURBO DNase. Reactions were incubated at 37° C. for 30 minutes. Five microliters (5 µl) of DNase inactivation reagent was added to each tube and mixed. Samples were incubated at room temperature for three minutes, mixed again, and incubated at room temperature for an additional two minutes. Samples were centrifuged at 20,000×g for five minutes. Forty microliters (40 µl) of the supernatant was removed while leaving behind the DNase inactivation slurry. Each DNase treated sample was quantified with the Nanodrop so that equivalent amounts of RNA could be used for cDNA synthesis.

Complementary DNA (cDNA) was prepared for each RNA sample by using the cDNA High Capacity kit (Applied Biosystems, Foster City, Calif.). Briefly, 1.5 µg of RNA was used as template in a fifty microliter reaction containing 1× reverse transcription buffer, 1× dNTPs, 1× random oligomers, and 125 units of Multiscribe reverse transcriptase. Additionally, noRT control reactions were prepared for each using 1.5 µg of DNase treated RNA under the same conditions as above without the Multiscribe reverse transcriptase. All samples were incubated at 25° C. for 10 minutes, 37° C. for 2 hours, 85° C. for 5 minutes, and overnight at 4° C.

Primers and probes were designed with the Primer Express 3 software from Applied Biosystems (Foster City, Calif.) for FATB, KASII, ERF3, KRAB1, and Tubulin. Primers were synthesized by Integrated DNA Technologies (Coralville, Iowa). The following are the sequences for the primers:

```
SEQ ID NO: 63:
FATB5 fwd-5' TCGCTGCCATAACAACCATTT 3';

SEQ ID NO: 64:
FATB5 rev-5' CGCCTGGGTTTCCAGTCA 3';

SEQ ID NO: 65:
KRAB1 fwd-5' AAGGATGTGTTCGTGGATTTCA 3';

SEQ ID NO: 66:
KRAB1 rev-5' CACAATCTGCTGTGCAGTATCAAG 3';

SEQ ID NO: 67:
ERF3 fwd-5' GCGGGCGGGAGTTGTTA 3';

SEQ ID NO: 68:
ERF3 rev-5' CCCCATCGGCGTTACATG 3';

SEQ ID NO: 69:
TUBULIN fwd-5' GAAGCTGAGAACAGCGATTGC 3';

SEQ ID NO: 70:
TUBULIN rev-5' GTTCCTCCTCCCAACGAATG 3'.
```

Probes were 6FAM/MGB synthesized by Applied Biosystems (Foster City, Calif.):

```
SEQ ID NO: 71:
FATB5 probe 6FAM TTTCTCAGCCGCCA;

SEQ ID NO: 72:
KRAB1 probe 6FAM TAGGGAAGAGTGGAAGCT;

SEQ ID NO: 73:
ERF3 probe 6FAM CAGGCCTCAGCCTT;
and

SEQ ID NO: 74:
TUBULIN probe 6FAM TACAAGGTTTCCAAGTTT.
```

The gene expression of FatB, ERF3, KRAB1 and tubulin were evaluated by real-time PCR with an Applied Biosystem 7900HT (Foster City, Calif.). A standard curve was prepared using aliquots of several cDNA samples within the different groups to establish the dynamic range and efficiency of the assay. Subsequent 1:5 and 1:4 serial dilutions of the initial dilution were made. Each cDNA sample was diluted 1:50 with 10 mM Tris, pH7.5. PCR reactions were prepared in a twenty microliter volume containing 1× Gene Expression Master Mix (Applied Biosystems; Foster City, Calif.), 0.8 µM of forward and reverse primers, 0.2 µM of gene specific 6FAM/MGB probe and 4 microliter of diluted cDNA. All reactions were run under the following conditions in the Applied Biosystem 7900HT with SDS version 2.4 software: Step 1) 50° C. for 2 minutes; Step 2) 95° C. for 10 minutes; Step 3) at 95° C. for 15 seconds, and; Step 4) at 60° C. for 1 minute. Steps 3 and 4 were repeated for 39 additional cycles. Tubulin gene expression was evaluated on each plate whereas FatB, ERF3, and KRAB I were run separately. All reactions were carried out in triplicate.

Standard curves were evaluated for regression and slope and threshold values adjusted as necessary. The noRT samples (minus reverse transcriptase controls that contained RNA with all cDNA reaction components except the reverse transcriptase) were compared with corresponding samples to ensure that a Ct difference of 5 to 7 was present. The data was imported into Excel for analysis. The average quantity value of FatB, ERF3, and KRAB1 was normalized to the quantity average of tubulin and reported as FatB and tubulin expression ratios.

15.4 Analysis of Seed-Specific FatB5 mRNA Down-Regulation in Immature Seeds

Figure 17:
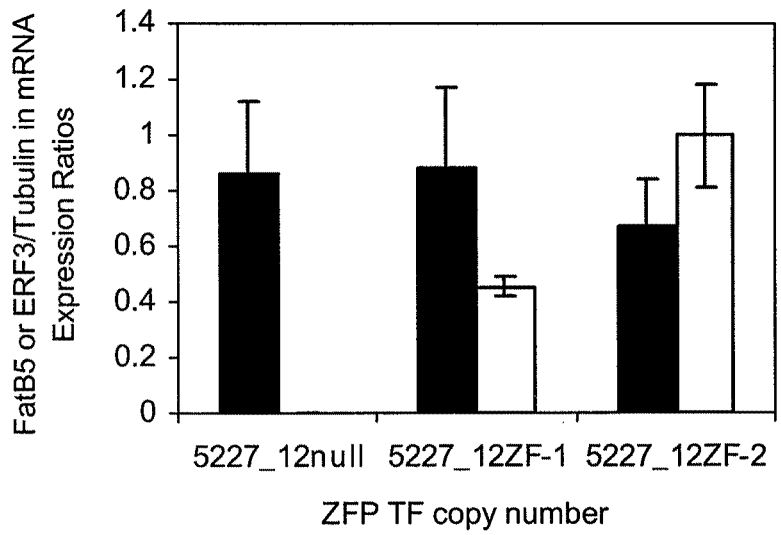
FIG. 17 displays FatB5 mRNA down-regulation (black bars) in T2 immature seed transformed with pDAS5227 ZFP TF construct. ZFP TF expression is represented by ERF3 expression (gray bars). 25 DAF immature seeds were analyzed from four—null, three heterozygous (5227_12ZF-1) and four homozygous (5227_12ZF-2) T1 plants of the event 5227-12.
Figure 18:
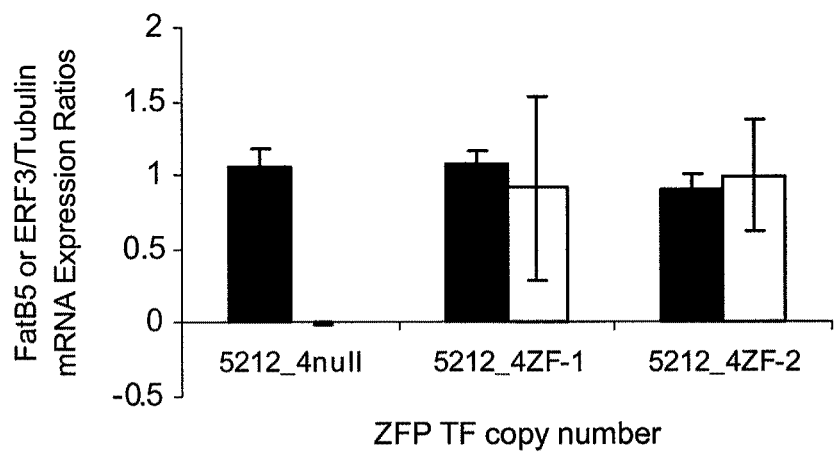
FIG. 18 shows FatB5 mRNA down-regulation (black bars) in T2 immature seed transformed with pDAS5212 ZFP TF construct. ZFP TF mRNA expression is represented by KRAB1 expression (gray bars). 25 DAF immature seeds were analyzed from five null, three heterozygous and four homozygous plants of the event 5212-4.

Results showed that FatB mRNA down-regulation 25 days after flowering (DAF) in immature seed was dependent on the state of zygosity of the $T_i$ plants. For example, no apparent FatB5 mRNA down-regulation was observed in the heterozygous plants (1 copy) of 5227-12 immature seed (FIG. 17). However, when the ZFP TF expression increased to 2-fold in the homozygous plants (2 copy), a 21% reduction in FatB5 mRNA expression was observed (p=0.025). Similar results were obtained in another event, 5212-4, of a different construct, pDAS5212. In this event, again, no apparent FatB5 down-regulation was observed in the heterozygous plants (FIG. 18). However, a 15% reduction in the FatB5 transcripts was observed in the homozygous plants when ZFP TF expression increased.

The null, heterozygous and homozygous plants of both events were advanced to maturity and FA profile was determined in a pool of 24 seed of each plant. This process of segregating out null lineages from the ZFP TF-containing lineages permitted FA profile differences which more closely reflected the presence of the ZFP TF.

Figure 19:
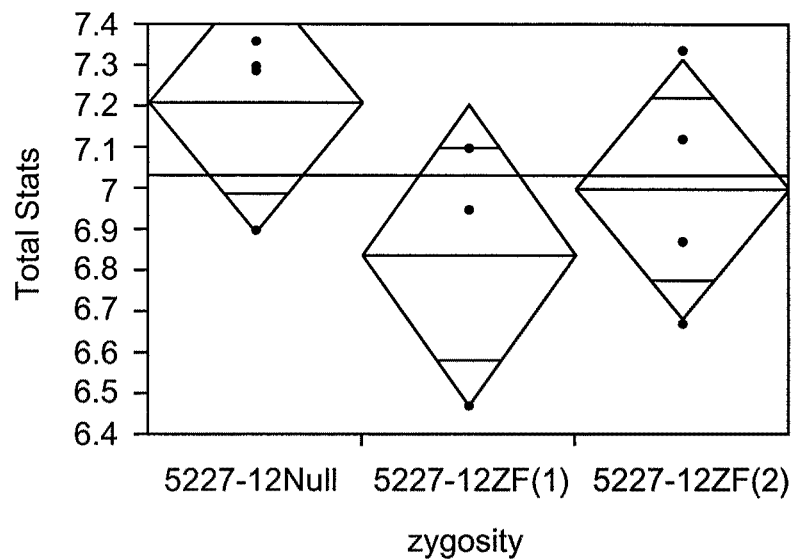
FIG. 19 shows a one way analysis of total saturated fatty acids (sats.) by zygosity in T2 seed of ZFP TF event 5227-12. T2 seed obtained from T1 null, heterozygous and homozygous parent plants are labeled as 5227-12ZF null, 5227-12ZF (1) and 5227-12ZF(2), respectively.

15.4 Analysis of FA Profile in $T_2$ Mature Seed $T_2$ mature seed FA profiles varied depending upon the ZFP TF zygosity of the $T_1$ parent plant for event 5227-12 (Tables 18A and 18B). Although the heterozygous $T_1$ plants did not exhibit any apparent FatB mRNA down-regulation in 25 DAF immature seed, their seed FA profile exhibited an 8% reduction in C18:0 content. No significant decrease in C16:0 content was observed. In addition, minor increases in C18:1 (oleic) and subsequent down-stream FAs were observed resulting in an overall 5.5% reduction in total saturated FA (Tables 18A and 18B, FIG. 19). When 5227-12 $T_1$ plants were homozygous for ZFP TF, the FatB mRNA was down-regulated significantly. The FA profile of these $T_2$ seed was different. An 11% increase in C16:1 content was observed resulting in a 2.7% reduction in total saturated FA (Tables 18A and 18B). However, no further reduction in C18:0 as compared to the heterozygous plants was observed. These changes concurred with the $T_1$ mature seed FA profile (Example 15.1).

in C18:0 in T2 homozygous seed was not more than that of T2 segregating seed. These results indicate that the homozygous ZFP TF copies may be triggering a feedback mechanism to adjust the FA profile since the FatB genes are indispensible

TABLE 18A

Indicated FA profile of T2 mature seed of event 5227-12

| Plant ID | Copy # | Total Sats | C14:0 | C16:0 | C16:1 | C18:0 | C18:1 (Oleic) | C18:1 (vaccenic) | Total C18:1 | C18:2 | C18:3 |
|---|---|---|---|---|---|---|---|---|---|---|---|
| 5227-12 Mean (n = 4) | 0 | 7.21 | 0.05 | 4.00 | 0.28 | 2.06 | 71.47 | 5.27 | 76.74 | 10.92 | 3.22 |
| 5227-12 Std Dev (n = 4) | 0 | 0.21 | 0.01 | 0.09 | 0.02 | 0.10 | 0.56 | 0.29 | 0.62 | 0.29 | 0.34 |
| 5227-12 Mean (n = 3) | 1 | 6.84 | 0.05 | 3.82 | 0.25 | 1.88 | 71.99 | 4.88 | 76.87 | 11.03 | 3.33 |
| 5227-12 Std Dev (n = 3) | 1 | 0.33 | 0.01 | 0.33 | 0.03 | 0.04 | 0.50 | 0.19 | 0.32 | 0.05 | 0.31 |
| 5227-12 Mean (n = 4) | 2 | 7.00 | 0.05 | 3.96 | 0.30 | 1.91 | 70.99 | 5.09 | 76.08 | 11.62 | 3.30 |
| 5227-12 Std Dev (n = 4) | 2 | 0.29 | 0.00 | 0.47 | 0.03 | 0.40 | 1.50 | 0.25 | 1.44 | 1.21 | 0.26 |

TABLE 18B

FA profile of T2 mature seed of event 5227-12

| Plant ID | Copy Number | Total Sats | C20:0 | C20:1 | C20:2 | C22:0 | C24:0 | C24:1 |
|---|---|---|---|---|---|---|---|---|
| 5227-12 Mean (n = 4) | 0 | 7.21 | 0.64 | 1.01 | 0.04 | 0.27 | 0.13 | 0.09 |
| 5227-12 Std Dev (n = 4) | 0 | 0.21 | 0.03 | 0.02 | 0.01 | 0.01 | 0.03 | 0.01 |
| 5227-12 Mean (n = 3) | 1 | 6.84 | 0.62 | 1.07 | 0.04 | 0.28 | 0.12 | 0.09 |
| 5227-12 Std Dev (n = 3) | 1 | 0.33 | 0.02 | 0.11 | 0.00 | 0.03 | 0.02 | 0.01 |
| 5227-12 Mean (n = 4) | 2 | 7.00 | 0.62 | 1.06 | 0.04 | 0.27 | 0.12 | 0.08 |
| 5227-12 Std Dev (n = 4) | 2 | 0.29 | 0.09 | 0.03 | 0.01 | 0.03 | 0.03 | 0.01 |

Figure 20:
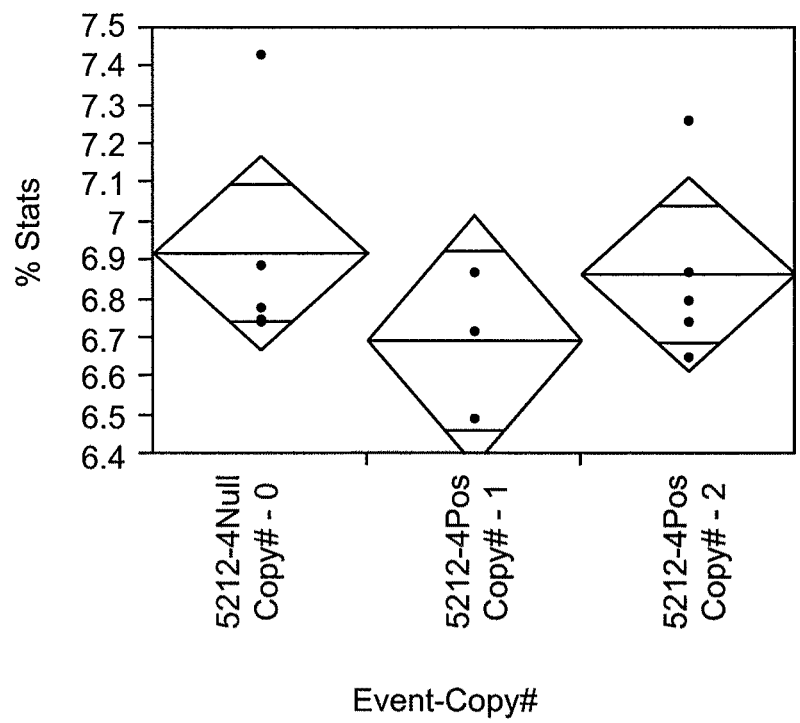
FIG. 20 shows a one way analysis of total saturated fatty acids (sats.) by zygosity in T2 seed of ZFP TF event 5212-4. T2 seed obtained from T1 null, heterozygous and homozygous parent plants are labeled as 5212-4ZF null, 5212-4ZF(1) and 5212-4(2) respectively.

Similar results were obtained in $T_2$ mature seed FA profiles of event 5212-4. In heterozygous plant seed, a 5.5% reduction in C18:0 content was observed resulting in a total saturated FA reduction of 3.2% (Table 18, FIG. 20). A minor increase in C18:1 was also observed; otherwise the concentrations of the remaining FAs exhibited minor decreases. Homozygous plants did not show a higher reduction in C18:0 content as compared to that of hemizygous plants despite significant down-regulation of FatB mRNA.

In summary, transcriptional down-regulation of the FatB5 gene with seed-specific expression of ZFP TFs has been demonstrated in these examples. The ZFP TFs were effective in conferring transcriptional down-regulation of the target FatB5 gene in T2 homozygous seed. However, the reduction for plant growth and development (Bonaventure et al., *The Plant Cell*, 2003 15:1020-1033). It is noteworthy that FatB mRNA down-regulation mediated by ZFP TF in the immature seed is inversely related to that of FatB up-regulation for changes in the C18:0 content.

These examples show that ZFP TF targeted effects on the native FatB genes specifically altered FatB mRNA quantity, thus resulting in specific and heritable FA profile changes in *B. napus*.

TABLE 19A

FA profile of event 5212-4 T2 seed at different zygosity levels

| Plant No. | Copy No. | % Total Sats | C14:0 | C16:0 | C16:1 | C18:0 | C18:1 | C18:2 | C18:3 |
|---|---|---|---|---|---|---|---|---|---|
| 5212-4 Mean (n = 5) | 0 | 7.02 | 0.05 | 3.94 | 0.32 | 1.88 | 76.03 | 11.17 | 3.50 |
| 5212-4 Std Dev (n = 5) | 0 | 0.29 | 0.01 | 0.18 | 0.02 | 0.12 | 1.44 | 1.06 | 0.56 |
| 5212-4 Mean (n = 5) | 1 | 6.79 | 0.04 | 3.83 | 0.32 | 1.81 | 76.86 | 10.74 | 3.36 |
| 5212-4 Std Dev (n = 5) | 1 | 0.19 | 0.00 | 0.07 | 0.01 | 0.17 | 0.26 | 0.31 | 0.11 |
| 5212-4 Mean (n = 5) | 2 | 6.96 | 0.04 | 3.89 | 0.32 | 1.89 | 76.38 | 11.00 | 3.38 |
| 5212-4 Std Dev (n = 5) | 2 | 0.24 | 0.00 | 0.08 | 0.01 | 0.16 | 0.81 | 0.78 | 0.30 |

TABLE 19B

FA profile of event 5212-4 T2 seed at different zygosity levels

| Plant No. | Copy No. | % Total Sats | C20:0 | C20:1 | C20:2 | C22:0 | C24:0 | C24:1 |
|---|---|---|---|---|---|---|---|---|
| 5212-4 Mean (n = 5) | 0 | 7.02 | 0.64 | 1.16 | 0.04 | 0.33 | 0.20 | 0.11 |
| 5212-4 Std Dev (n = 5) | 0 | 0.29 | 0.07 | 0.06 | 0.01 | 0.04 | 0.05 | 0.01 |
| 5212-4 Mean (n = 5) | 1 | 6.79 | 0.62 | 1.11 | 0.04 | 0.31 | 0.18 | 0.10 |
| 5212-4 Std Dev (n = 5) | 1 | 0.19 | 0.05 | 0.03 | 0.00 | 0.03 | 0.02 | 0.00 |
| 5212-4 Mean (n = 5) | 2 | 6.96 | 0.63 | 1.12 | 0.05 | 0.31 | 0.21 | 0.10 |
| 5212-4 Std Dev (n = 5) | 2 | 0.24 | 0.07 | 0.05 | 0.01 | 0.03 | 0.05 | 0.01 |

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A non-naturally occurring zinc finger protein that modulates expression of a β-ketoacyl-ACP synthetase (KAS) gene, wherein the zinc finger protein comprises five or six zinc finger recognition regions designated and ordered F1 to F5 for five finger protein or F1 to F6 for six finger protein as shown in a single row of Table 1, wherein the zinc finger proteins binds to a target site in the KAS gene.

2. A fusion protein comprising a zinc finger protein of claim 1 and a functional domain.

3. The fusion protein of claim 2, wherein the functional domain is a transcriptional regulatory domain 4. The zinc finger protein of claim 1, wherein the plant gene is contained within a *Brassica* plant.

5. The fusion protein of claim 2, wherein the plant gene is contained within a *Brassica* plant.

6. A polynucleotide encoding one or more zinc finger proteins of claim 1.

7. A method of modifying expression of a KAS gene in a plant cell, the method comprising:

introducing, into the plant cell, one or more expression vectors comprising at least one polynucleotide according to claim 6, under conditions such that the one or more zinc finger proteins are expressed and expression of the KAS gene is modified.

8. The method of claim 7, wherein expression of at least one gene is activated.

9. The method of claim 7, wherein expression of at least one gene is repressed.

10. A plant cell comprising a KAS gene whose expression has been modified by the method of claim 7.

11. The plant cell of claim 10, wherein the cell is within a seed and fatty acid content in the seed is modified.

12. A plant comprising at least one cell according to claim 10.

13. A plant comprising at least one cell according to claim 11.

14. The seed or progeny of a plant according to claim 10.

15. The seed or progeny of a plant according to claim 11.

16. A plant comprising at least one cell comprising at least one zinc finger protein according to claim 1.

17. The seed or progeny of a plant according to claim 16.

18. A plant comprising at least one cell comprising at least one polynucleotide according to claim 6.

19. The seed or progeny of a plant according to claim 18.

* * * * *

```
                        SEQUENCE LISTING

<160> NUMBER OF SEQ ID NOS: 96

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcggatccg aacactgcgt ttgctggctt tgatgaaa                            38

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 2
ctcgagctgc tactgctagt tccggtggag gagcc                              35

<210> SEQ ID NO 3
<211> LENGTH: 736
<212> TYPE: DNA
<213> ORGANISM: Brassica napus

<400> SEQUENCE: 3
gaattcgccc ttcgcggatc cgaacactgc gtttgctggc tttgatgaaa atcttttgac      60
gtctccacgc acgagtttac gcatcccaga cgcctcctta gagagaagag agagatcgag     120
atcgatttcc tccctcttaa acctctctct ctctcgtgaa tctcatttcc ctttgccgct     180
agattctctc ttcaccctttt tctcgcccctt ccttcctctc ctcattactt ttttgtcgtc     240
ttctgctctc tctctctctc agcactcttc gccatggtgg gtgctgctgc gtcttcctgt     300
tacgcatctc cgctatgcac ctggttcgtc gccgcctgca tgtccgtctc ccacggcggc     360
ggagattccc gacaagccgt cgctctcaaa tctaccgggc ggagtcgtcg aagcagacaa     420
cagctcacca aatgctctgg atccggtagc agcactactt cctttgggcc ttgcaatcac     480
tacaatgcct tgtcttctct cttcggatcg aactctgttt ctctcaatcg aaaccagagg     540
aggttgactc gagctgctac tgctagttcc ggtggaggag ccatggctgt tgcgatggat     600
atggaaaagg aagccaaggt tgacaacaaa cctcctacgg agcagcgccg ggttgttgtg     660
acaggcatgg gagttgaaac atcactaggt catgaccctg acaccttta tgagaatctc     720 ctacaagggc gaattc                                                     736

<210> SEQ ID NO 4
<211> LENGTH: 732
<212> TYPE: DNA
<213> ORGANISM: Brassica napus

<400> SEQUENCE: 4
gaattcgccc ttcgcggatc cgaacactgc gtttgctggc tttgatgaaa atgtatgtat      60
cttttgacgt ctccacgtac gagtttacgc atccagacgc ctcgttagag agaagagaga     120
gatcgagatc gagatcgaga tcgatttcct ccctctctct ctcgtgaatc tcatttcccc     180
ttaccgctag attctctctt caccctttc tcgcccttcc ttctcctcat tatttttttg     240
tcgtcttctg ctctctcaca gcactcttct ctttagctat ggtgggtggt gctgcgtctt     300
cttcctgtta cgcatctccg ctatgcacct ggttcgtcgc tgcttgcatg tccgtctccc     360
acggcggcgg agattcccga caagccgtct ccctcaaatc taccgggcgg agtcgtcgaa     420
gcagacgaca gctcaccaaa tgcttggctc tttctggatc cggtagcgtt caggaggctc     480
tcgtcactac ttccttttggg ccttgcaatc actacaatgc cttgtcttct ctcttcggat     540
cgaactctgt ttctctcaat cgaaaccaga ggaggttgaa tctggctgct gctagttccg     600
gtggaggagc catggctgtt gcgatggata tgcaaaagga agccaaggtt gacaacaaac     660
cccctacgga gcagcgccgt gttgtggtga caggcatggg agttgaaaca tcactaggtc     720
aagggcgaat tc                                                         732

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 5

Arg Ser Asp Asn Leu Ser Val
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Lys Ile Asn Leu Gln Val
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Thr Leu Ser Glu
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Arg Ser Ser Arg Ile Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Ala Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp His Leu Ser Ala
1               5

<210> SEQ ID NO 11
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Thr Ser Ser Ser Arg Ile Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asp Asn Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Ser His Leu Ala Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Asp Asn Leu Ser Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Asn Ala His Arg Thr Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Gly Asn Leu Ala Arg
1               5
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp His Leu Ser Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Lys Ala Asn Arg Thr Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Asp Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ser Ala Asn Leu Ser Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Asp Leu Ser Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ala Asn Leu Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Lys Ser Asn Arg Lys Lys
1               5

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgtggagacg tcaaaaga                                                 18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaggaagggc gagaaaaggg                                               20

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agatgcgtaa caggaag                                                  17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctaccgggcg gagtcgt                                                  17

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
ttgactcgag ctgctactgc                                                  20
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
tttccatatc catcgcaaca                                                  20
```

<210> SEQ ID NO 30
<211> LENGTH: 447
<212> TYPE: DNA
<213> ORGANISM: Brassica napus

<400> SEQUENCE: 30

```
actcagcact cttcgccatg gtgggtgctg ctgcgtcttc ctgttacgca tctccgctat      60
gcacctggtt cgtcgccgcc tgcatgtccg tctcccacgg cggcggagat tcccgacaag     120
ccgtcgctct caaatctacc gggcggagtc gtcgaagcag acaacagctc accaaatgct    180
ctggatccgg tagcagcact acttcctttg ggccttgcaa tcactacaat gccttgtctt    240
ctctcttcgg atcgaactct gtttctctca atcgaaacca gaggaggttg actcgagctg    300
ctactgctag ttccggtgga ggagccatgg ctgttgcgat ggatatggaa aaggaagcca    360
aggttgacaa caaacctcct acggagcagc gccgggttgt tgtgacaggc atgggagttg    420
aaacatcact aggtcaaggg cgaattc                                        447
```

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
acagcgattg cctacaagg                                                   19
```

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
agatggttaa gatcaccaaa gg                                               22
```

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
aaggaagagg aaggagtcta acag                                             24
```

```
<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttctgctct ccaccgta                                                   18

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggtcaacgga tcaggatatt cttg                                            24

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccatgttggc aaaggcaacc                                                 20

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acaagagtgg attgatgatc tagagaggt                                       29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctttgatgcc tatgtgacac gtaaacagt                                       29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
ccagcgtaag caataccagc cacaacacc                                       29

<210> SEQ ID NO 40
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctctctacc accgtctcac atg                                              23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gatctggccg gactgtttca                                                  20

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
cgctcctcag ctaccacctc aacca                                            25

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcgatcttga tatgttggga ga                                               22

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggtgcagaa tcatgtggtg                                                  20

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
ttgatggtga agatgt                                                      16

<210> SEQ ID NO 46
<211> LENGTH: 718
<212> TYPE: DNA
<213> ORGANISM: Brassica napus
```

```
<400> SEQUENCE: 46
gaattcgccc ttcgcggatc cgaacactgc gtttgctggc tttgatgaaa gcttgtatgt    60
atgtatcttt tgacgtctcc acgtacgagt ttacgcatcc agacgcctcg ttagagagaa   120
gagrgagatc gagatcgaga tcgagatcga tttcctcccct ctctctctcg tgaatctcat   180
ttccccttac cgctagattc tctcttcacc cttttctcgc ccttccttct cctcattatt   240
tttttgtcgt cttctgctct ctcwcakcwc tcwkcwctct tmgcyatggt gggtgstgct   300
gcgtcttctt cctgttacgc atctccgcta tgcacctggt tcgtcgcygc ytgcatgtcc   360
gtctcccacg gcggcggaga ttcccgacaa gccgtckcyc tcaaatctac cgggcggagt   420
cgtcgaagca gacaacagct caccaaatgc tctggatccg gtagcagcac tacttccttt   480
gggccttgca atcactacaa tgccttgtct tctctcttcg gatcgaactc tgtttctctc   540
aatcgaaacc agaggaggtt gamtcgwgct gctrctgcta gttccggtgg aggagccatg   600
gctgttgcga tggatatgca aaaggaagcc aaggttgaca caaaccccc tacgagcar    660 cgccgtgttg tggtgacagg catgggagtt gaaacatcac taggtcaagg gcgaattc    718

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aacgaaagga gatcgagaga ggagagag                                       28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cgaaagggag atcgagagag gcaccgca                                       28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaggagaact ttagggtttg gggagact                                       28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaggagaatt tagggtttg gggagact                                        28
```

-continued

```
<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctccgaagag attggcgtaa cacttcgt                                        28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctccgaagag attggcgtaa ccttcatt                                        28

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctttgaacgc ttatcttcct c                                               21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttccacaaca tctccccaag                                                 20

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
ctcaggctcc accc                                                       14

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctttgaaagc tcatcttcct c                                               21

<210> SEQ ID NO 57
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttccacaaca tctccccaag                                                    20

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
aaccttcatc ctccca                                                        16

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcgatcttga tatgttggga ga                                                 22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggtgcagaa tcatgtggtg                                                    20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acgagctacc tgacggacaa g                                                  21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gagcgacggc tggaagagta                                                    20

<210> SEQ ID NO 63
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 63
tcgctgccat aacaaccatt t                                              21

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgcctgggtt tccagtca                                                  18

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aaggatgtgt tcgtggattt ca                                             22

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cacaatctgc tgtgcagtat caag                                           24

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gcgggcggga gttgtta                                                   17

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccccatcggc gttacatg                                                  18

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                                     primer

<400> SEQUENCE: 69
gaagctgaga acagcgattg c                                                 21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gttcctcctc ccaacgaatg                                                   20

<210> SEQ ID NO 71
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
tttctcagcc gcca                                                         14

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
tagggaagag tggaagct                                                     18

<210> SEQ ID NO 73
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
caggcctcag cctt                                                         14

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
tacaaggttt ccaagttt                                                     18

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

Arg Ser Asp Asn Leu Ser Ala
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Ala His Arg Lys Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Ser His Arg Lys Thr
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ser Asp His Leu Ser Val
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Asn Ala His Arg Ile Glu
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ser Asp His Leu Ser Lys
1               5

<210> SEQ ID NO 81
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 81

Gln Asn Ala Asn Arg Ile Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ser Asp His Leu Ser Thr
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Ser Asn Thr Arg Lys Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Asp His Leu Ser Gln
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Ser Ala Ser Arg Lys Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ser Gly His Leu Ser Arg
1               5
```

```
<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asn Ser Asp Ser Leu Thr Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Arg Ala Asp Leu Ser Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Asp Ser Leu Ser Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Asn Ala His Arg Lys Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Asn Ala Asp Arg Ile Thr
1               5

<210> SEQ ID NO 92
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(200)
```

<223> OTHER INFORMATION: This region may encompass 5 to 200 "Gly" residues

<400> SEQUENCE: 92

```
Gly Gly Gly Gly Gly Gly Gly Gly Gly Gly Gly Gly Gly Gly Gly
1               5                   10                  15
Gly Gly Gly Gly Gly Gly Gly Gly Gly Gly Gly Gly Gly Gly Gly
            20                  25                  30
Gly Gly Gly Gly Gly Gly Gly Gly Gly Gly Gly Gly Gly Gly Gly
        35                  40                  45
Gly Gly Gly Gly Gly Gly Gly Gly Gly Gly Gly Gly Gly Gly Gly
    50                  55                  60
Gly Gly Gly Gly Gly Gly Gly Gly Gly Gly Gly Gly Gly Gly Gly
65                  70                  75                  80
Gly Gly Gly Gly Gly Gly Gly Gly Gly Gly Gly Gly Gly Gly Gly
                85                  90                  95
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly
        195                 200
```

<210> SEQ ID NO 93
<211> LENGTH: 1693
<212> TYPE: DNA
<213> ORGANISM: Brassica napus

<400> SEQUENCE: 93

```
ctcgagctgc tactgctagt tccggtggag gagccatggc tgttgcgatg gatatggaaa    60
aggaagccaa ggttgacaac aaacctccta cggagcagcg ccgggttgtt gtgacaggca   120
tgggagttga acatcacta ggtcatgacc ctgacacctt ttatgagaat ctcctacaag    180
gcaacagtgg tattagccag attgagaatt ttgattgttc tgcttttcct acgagaattg   240
ctggagagat caagtcattc tcgactgaag gtgggttgc tccaaaactc tcaaagagga    300
tggacaagtt catgctctat cttctcactg ctggcaagaa ggctttggtt gatggtgggg   360
taaccgaaga agtcatggca gagtttgaca aagccaaatg cggagtcttg attggctctg   420
caatgggagg catgaaggtc tttcaagatg ctattgaagc tatgaagatc tcttacaaga   480
agatgaatcc tttctgtgtg cctttcgcga caacgaacat gggttctgct atgcttgctt   540
tggatctggg atggatgggg ccaaactatt ctatctcaac tgcttgtgca caagcaact    600
tttgcattct caattcagca aaccacatta tcaaaggaga agctgatgta atgctctgtg   660
gtggctcgga ttcagttatt attccaatag ggttgggagg ttttgttgca tgccgtgctc   720
tttctcaaag gaataatgat cccacaaaag cttcacgccc ttgggatagc aaccgagatg   780
gtttcgtgat gggagaggga gctggagttt gcttttgga agagcttgaa catgctaaga   840
```

```
aaagaggagc aacaatctat gcagagttcc ttggtgggag tttcacatgt gatgcctatc      900
acatgaccga gcctcgccct gatggtgctg gtgtgattct gtgtattgag agagcattgg      960
ctgatgctgg gatttccaaa gaacagataa actatataaa tgcacatgca acctctacac     1020
cagctggaga ccttaaggag taccaagccc ttgctcactg ctttggccaa atcctgaga      1080 taaaagttaa ttccacaaaa tctatgattg dacacttgct gggagctgct ggggccgttg     1140
aagctgtcgc aactgtgcag gccataagga ccggatgggt catccaaat atcaaccttg      1200 agagtccaga caatggagtg gatacaaatt tgctggtggg tcctgagaag gagagattgg     1260
acattaaagc agccttgtca aattcattcg ggttggtgg ccacaactcc agcatcattt      1320
ttgctcctta caagtgaaag cactcattgc ctgtactcca aacctggttg tgtaacttgc     1380
tgtaagtgtt tacaagaact ccccatgtta tgttgttgcg ggaatcaaca cagtttgtta     1440
aactaccaag agctaagcta agtttcctta ggatcaagat ccgtttgtgc cagagaactt     1500
ggacaaagag caaacgtagc agagtttgga tttagcttcc gtgtgatacc ttttgagtgg     1560
aatctttgta gccttttctt ttttgtagtg tttcatttct atttgttaat cattacaatc     1620
tgaaaattgc caaccaatt ctccgttaaa tttagtaact ctacacaaaa aaaaaaaaaa      1680
aaaaaaaaaa aaa                                                       1693

<210> SEQ ID NO 94
<211> LENGTH: 1767
<212> TYPE: DNA
<213> ORGANISM: Arabidopsis thaliana

<400> SEQUENCE: 94
attctctctt cttctcttca cccatttctc gctttctcct ttgttctctc atctgggttc       60
ttctcaaagc ctcttccttt ttttgccatg gtgggtgcgt cttcctctta cgcatctccg      120
ttatgtacct ggtttgttgc tgcttgcatg tccgtctctc acggtggagg agatagccgt      180
caggctgttg ctcttcaatc tggtgggcgg agtcggcgaa ggaggcagct tagcaaatgc      240
tctgtcgctt ctggatccgc tagcattcag gctctcgtca cttccttgttt ggattttggt      300 ccttgtactc actacaacaa caacaatgca ttgtcttctc tctttggatc gaatagtgtt      360
tctttgaatc gaaaccagag gagattgaat cgtgctgcta gctccggtgg agccatggca      420
gtgatggaga tggaaaagga agctgcggtt aacaagaaac cacctacgga gcagcgtcga      480
gttgtagtga caggcatggg agttgaaaca tcattgggtc atgacccaca taccttctat      540
gagaatttgc tacaaggcaa cagtggtatt agccagattg aaaattttga ttgttctgaa      600
tttcctacgc gaattgcggg agagatcaaa gcttctcga ctgaaggatg ggttgctcca       660
aaactttcta aaggatgga caaattcatg ctctatcttc tcacagctgg taagaaagct      720
ttggctgatg gtggggttac tgatgaagta atggcagagt tgacaaaac caaatgtgga      780 gttttgattg gctcggcaat gggaggaatg aaggtcttt acgatgctat tgaagctctg      840
agaatctctt acaagaagat gaatcctttt tgtgtacctt ttgcgacaac aaacatgggt      900
tctgctatgc ttgccatgga tctgggatgg atgggccaa actattctat ttcaactgct      960
tgtgccacaa gcaactttg cattctgaat tcagcaaacc acattattaa aggtgaagct     1020
gatgtaatgc tctgtggtgg ctcagatgca gttattattc aatagggtt gggaggtttt     1080 gttgcatgcc gggctctttc acaaaggaat aatgatccca caaaagcttc acgtccttgg     1140
gataccaatc gagatggttt cgtgatggga gaggagctg gagttctact tttggaagaa     1200
ctcgagcatg ctaagaaaag aggtgcaact atctacgcag agttcctcgg tgggagtttc     1260
```

| acatgtgatg cctatcacat gaccgagcct caccctgatg gggctggtgt tattctctgt | 1320 |
| attgagagag cgttagctag tgctgggatt tccaaggaac aaataaatta cataaatgca | 1380 |
| catgcaacct caacgcatgc tggagatatt aaggaatacc aagcccttgc tcactgtttt | 1440 |
| ggccaaaatc ctgagcttaa ggtaaattcc acaaaatcta tgattggaca cttgctggga | 1500 |
| gctgctgggg ccgtggaggc tgttgcaact gtgcaggcga tacggaccgg atgggttcat | 1560 |
| ccaaatatca acctcgagaa tccagacagt ggagtggata caaagctgct ggtgggtcct | 1620 |
| aagaaggaga gactggacat taaagcagcc ttgtcaaatt cattcgggtt tggtggtcat | 1680 |
| aactccagca tcattttgc tccttacaag tgaaagcgaa agcagttgct tgtactccaa | 1740 |
| acctgattgt ataacttgct gtaaggt | 1767 |

<210> SEQ ID NO 95
<211> LENGTH: 893
<212> TYPE: DNA
<213> ORGANISM: Brassica rapa

<400> SEQUENCE: 95

| gacatggata ttttctgaga tttggaagtg tggatttgat ataagcaaag caaagcaagt | 60 |
| gctcgcttgt atgtatcttt tgacgtctcc acgcacgagt ttacgcatcc agacgcctcg | 120 |
| ttagagagaa gagagagatc gagatcgatt cctcccctt aaacctctct ctctctcgtg | 180 |
| aatctcattt ccccttaccg ctagattctc tcttcaccct tttctcgccc ttccttcctt | 240 |
| ctcctcatta cttttttgtc gtcttctgct ctctctctct ctcagcactc ttcgctttag | 300 |
| ctatggtggg tgctgctgcg tcttcctgct acgcatctcc gctatgcacc tggttcgtcg | 360 |
| ctgcctgcat gtccgtctcc cacggcggcg gagattcccg acaagccgtc gctctcaaat | 420 |
| ctagcgggcg gagtcgtcga agcagacaac aactcaccaa atgctctgga tccggtagca | 480 |
| gcgttcagca ggctctcgtc actacttcct ttgggccttg caatcactac aatgccttgt | 540 |
| cttctctctt cggatcgaac tctgtttctc tcaatcgaaa ccagaggagg ttgactcgag | 600 |
| ctgctactgc tagttccggt aatttaacat ttcaccaatc tgggttttg atttgtgggt | 660 |
| attgtttgca gagttgacaa gctttgtttt tgttagtaaa gttctctttt ttatgtgttt | 720 |
| atgttatttg gtcaaatgat tcaacttgga gatcaagttt aacgggaaag tatgctgatt | 780 |
| tggaatctca gcttaattgt caagtttcat tctttattgt gtgtgtaata tgcaaagcac | 840 |
| atttctgtga gtttgattca atattggact ctagataagg agtatgatga tac | 893 |

<210> SEQ ID NO 96
<211> LENGTH: 812
<212> TYPE: DNA
<213> ORGANISM: Brassica oleracea

<400> SEQUENCE: 96

| acggcacttt acgcaccaat atataccata tggtagccag ttaagggtac gaagtgattt | 60 |
| tccccttttc ttatgtatac agactccaat tccccaaatt tactctggtc atcgaacatc | 120 |
| gatacgtttg tatgtatgta cgtcttatct ctctctctgg ctatctctgt gtgttttgtt | 180 |
| gttaataaca ggaggttttg ttttgttttc tttgacgtct ccacgcacga ttttaagcct | 240 |
| ccgttacgct ctgcacgcct cctgaaagag agagagagag agatcgaatc atcttaatta | 300 |
| aacctctctc gtgaatccgc tagattctct cttcaccgtt ttctcgcctc tcctctcctc | 360 |
| tccattttgt tttcttcttc ttcgtcttct tcttcttgcc attgccatgg tgggtgctgc | 420 |
| tgcgtcttcc tgttacgcat ctcccttatg caccttcttc gttgctgctt gcatgtccct | 480 |

```
ctctcacggc ggcggtgata cccgtcaagc ctttgggcgg agccgtcgaa ggagacaaca      540
gctcggcaaa tgctctggat ccggtagcat tctcgtgtct tcttgtttgg agtttaagcc      600
ttgcagtcac tacaacaaga acaacaaagg caatgccttt cctctcctcg gatcgaatag      660
cctttctctg aatcgaaagc agaggaaact gaatcgagca acttcttctt cttccggtat      720
aaacattctt ctcccaaaat ctcaagtctt ggtttctggg tatcgtttgc aagctgacaa      780
gctttgtttt ttgtgtataa agtttctcct tt                                    812
```